US 10,077,290 B2

(12) United States Patent
Walensky et al.

(10) Patent No.: US 10,077,290 B2
(45) Date of Patent: Sep. 18, 2018

(54) STABILIZED ANTIVIRAL FUSION HELICES

(71) Applicant: Dana-Farber Cancer Institute, Inc., Boston, MA (US)

(72) Inventors: Loren D. Walensky, Newton, MA (US); Gregory H. Bird, Pelham, NH (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 14/367,973

(22) PCT Filed: Dec. 31, 2012

(86) PCT No.: PCT/US2012/072315
§ 371 (c)(1),
(2) Date: Jun. 23, 2014

(87) PCT Pub. No.: WO2013/102211
PCT Pub. Date: Jul. 4, 2013

(65) Prior Publication Data
US 2014/0370042 A1 Dec. 18, 2014

Related U.S. Application Data

(60) Provisional application No. 61/581,436, filed on Dec. 29, 2011.

(51) Int. Cl.
| A61K 39/155 | (2006.01) |
| C07K 14/005 | (2006.01) |
| A61K 47/48 | (2006.01) |
| C12N 7/00 | (2006.01) |
| G01N 33/68 | (2006.01) |
| A61K 39/12 | (2006.01) |
| A61K 38/00 | (2006.01) |

(52) U.S. Cl.
CPC ............ *C07K 14/005* (2013.01); *A61K 39/12* (2013.01); *A61K 39/155* (2013.01); *A61K 47/48215* (2013.01); *C12N 7/00* (2013.01); *G01N 33/68* (2013.01); *A61K 38/00* (2013.01); *C12N 2760/18522* (2013.01); *C12N 2760/18533* (2013.01); *C12N 2760/18534* (2013.01); *C12N 2760/18571* (2013.01); *G01N 2333/135* (2013.01); *G01N 2500/02* (2013.01)

(58) Field of Classification Search
None
See application file for complete search history.

(56) References Cited

U.S. PATENT DOCUMENTS

| 5,446,090 A | 8/1995 | Harris |
| 6,348,558 B1 | 2/2002 | Harris et al. |
| 7,723,468 B2 | 5/2010 | Daffre et al. |
| 7,858,098 B2 | 12/2010 | Dubin et al. |
| 8,889,632 B2 | 11/2014 | Bernal et al. |
| 2003/0104581 A1* | 6/2003 | Hoess ................ C07K 14/005 435/69.7 |
| 2004/0067503 A1 | 4/2004 | Tan et al. |
| 2005/0250680 A1 | 11/2005 | Walensky et al. |
| 2006/0008848 A1 | 1/2006 | Verdine et al. |
| 2010/0093086 A1 | 4/2010 | Lin et al. |

FOREIGN PATENT DOCUMENTS

| WO | WO 1999/14259 | 3/1999 |
| WO | WO 1999/34833 | 7/1999 |
| WO | WO 2008/121767 | 10/2008 |
| WO | 2009/108261 | 9/2009 |
| WO | WO 2009/108261 A2 * | 9/2009 |
| WO | WO 2010/060112 | 5/2010 |
| WO | WO 2010/068684 | 6/2010 |
| WO | WO 2010/148335 | 12/2010 |

OTHER PUBLICATIONS

Johnson et al., J Infect Dis. 1999 vol. 180(1):35-40.*
Murphy et al. Virus Research 1994 vol. 32, pp. 13-26.*
Weisshaar et al. DNA and Cell Biology 2015, vol. 34, pp. 505-510.*
Sun et al. Viruses, 2013 vol. 5, pp. 211-225.*
Ogra, P., Paediatric Respiratory Reviews (2004) 5(Suppl A), S119-S126.*
Adams et al., *Palivizumab-resistant human respiratory syncytial virus infection in infancy*, Clin. Infect. Disease, 51(2):185-188, 2010.
Altschul et al. *Gapped BLAST and PSI-BLAST: a new generation of protein database search programs*, Nucleic Acids Res. 25(17):3389-3402, 1997.
Aristoteli et al., *Evaluation of Endogenous Plasma Peptide Extraction Methods for Mass Spectrometric Biomarker Discovery*, Journal of Proteome Res., 6:571-581, 2007.
Bang, et al., *Total Chemical Synthesis of Crambin*, J. Am. Chem. Soc. 126:1377-1383, 2004.
Bird et al., *Synthesis and Biophysical Characterization of Stabilized α-Helices of BCL-2 Domains*, Methods Enzymol., 446:369-386, 2008.
Bird et al., *Hydrocarbon double-stapling remedies the proteolytic instability of a lengthy peptide therapeutic*, PNAS USA, 107(32):14093-14098, 2010.
Bird et al, *Chemical Synthesis of Hydrocarbon-Stapled Peptides for Protein Interaction Research and Therapeutic Targeting*, Current Protocols in Chemical Biology, 3:99-117, 2011.

(Continued)

Primary Examiner — Shanon A Foley
Assistant Examiner — Myron G Hill
(74) Attorney, Agent, or Firm — Fish & Richardson P.C.

(57) ABSTRACT

Internally cross-linked peptides useful for interfering with Respiratory Syncytial Virus (RSV) infection is based on RSV-F protein. These peptides are capable of reducing infection in cellular and animal models.

37 Claims, 25 Drawing Sheets
Specification includes a Sequence Listing.

(56) References Cited

OTHER PUBLICATIONS

Blackwell et al., *Highly Efficient Synthesis of Covalently Cross-Linked Peptide Helices by Ring-Closing Metathesis*, Angewandte Chemie 37(23):3281-3284 (1998).

Blackwell et al., *Ring-Closing Metathesis of Olefinic Peptides: Design, Synthesis, and Structural Characterization of Macrocyclic Helical Peptides*, J. Org. Chem., 66: 5291-5302, 2001.

Broglia et al., *Design of HIV-1-PR inhibitors that do not create resistance: Blocking the folding of single monomers*, Protein Science, 14(10):2668-2681, 2005.

Cianci et al., *Targeting a binding pocket within the trimer-of-hairpins: small-molecule inhibition of viral fusion*, Proc. Natl. Acad. Sci., USA, 101(42):15046-15051, 2004.

Devi et al., *Antibodies to poly[(2~8)-a-N-acetylneuraminic acid] and poly[(2~9)a-N-acetylneuraminic acid] are elicited by immunization of mice with Escherichia coli K92 conjugates: Potential vaccines for groups B and C meningococci and E. coli K1*, Proc. Natl. Acad. Sci. USA 88:7175-7179, 1991.

Douglas et al., *Small molecules VP-14637 and JNJ-2408068 inhibit respiratory syncytial virus fusion by similar mechanisms*, J. Virol., 49(6):2460-2466, 2005.

Fattom et al., *Serum Antibody Response in Adult Volunteers Elicited by Injection of Streptococcus pneumoniae Type 12F Polysaccharide Alone or Conjugated to Diphtheria Toxoid*, Infect. Immun., 58:2309-2312, 1990.

Gavathiotis et al, *BAX Activation is Initiated at a Novel Interaction Site*, Nature, 455(7216):1076-1081, 2008.

Gavathiotis et al, *BH3-Triggered Structural Reorganization Drives the Activation of Pro-apoptotic BAX*, Molecular Cell, 40(3):481-492, 2010.

Gonzalez-Reyes et al., *Cleavage of the human respiratory syncytial virus fusion protein at two distinct sites is required for activation of membrane fusion*, Proc. Natl. Acad. Sci., USA, 98(17):9859-9864, 2003.

Hammond et al., *An Examination of Binding Motifs Associated With Inter-Particle Interactions between Facetted Nano-Crystals of Acetylsalicylic Acid and Ascorbic Acid through the Application of Molecular Grid-Based Search Methods*, J. Pharm. Sci., 98(1):4589-603, 2009.

Kawamoto et al. *Design of Triazole-stapled BCL9 α-Helical Peptides to Target the β-Catenin/B-cell CLL/lymphoma 9 (BCL9) Protein-Protein Interaction*, J. Med. Chem. 55(3):1137-1146, 2012.

Li et al., *Comparative immunogenicities of Vi polysaccharide protein conjugates composed of cholera toxin or its B subunit as a carrier bound to high- or lower-molecular-weight Vi*, Infect. Immun 57(12):3823-3827, 1989.

Maggon and Barik,, *New drugs and treatment for respiratory syncytial virus*, Rev. Med. Virol., 14(3):149-168, 2004.

Matthews et al., *The core of the respiratory syncytial virus fusion protein is a trimeric coiled coil*, J. Virol., 74(13):5911-5920, 2000.

Melikyan et al., *Imaging individual retroviral fusion events: from hemifusion to pore formation and growth*, Proc. Natl. Acad. Sci., USA, 102(24):8728-8733, 2005.

Melikyan, *Common principles and intermediates of viral protein-mediated fusion: the HIV-1 paradigm*, Retrovirology, 5:111, 2008 (13 pages).

Ng and Yang, *Revealing the Way of Self-Complementary Dimerization for a Shape-Persistent Macrocycle Using Density Functional Theory Calculations*, J. Phys. Chem. B., 111(50):13886-93, 2007.

Root et al., *Protein design of an HIV-1 entry inhibitor*, Science, 291(5505):884-888, 2001.

Schafmiester et al., *An All-Hydrocarbon Cross-Linking System for Enhancing the Helicity and Metabolic Stability of Peptides*, J. Am. Chem. Soc., 122:5891-5892, 2000.

Smith et al., *Modelling the structure of the fusion protein from human respiratory syncytial virus*, Protein Eng., 15(5):365-371, 2002.

Stewart et al, *The MCL-1 BH3 Helix is an Exclusive MCL-1 inhibitor and Apoptosis Sensitizer*, Nat. Chem. Biol., 6(8):595-601, 2010.

Sugrue et al., *Furin cleavage of the respiratory syncytial virus fusion protein is not a requirement for its transport to the surface of virus-infected cells*, J. Gen. Virol., 82(Pt 6):1375-1386, 2001.

Szu et al., *Vi Capsular Polysaccharide-Protein Conjugates for Prevention of Typhoid Fever Preparation, Characterization, and Immunogenicity in Laboratory Animals*, J. Exp. Med. 166:1510-1524, 1987.

Szu et al., *Relation between Structure and Immunologic Properties of the Vi Capsular Polysaccharide*, Infect. Immun. 59(12):4555-4561,1991.

Szu et al., *Laboratory and Preliminary Clinical Characterization of Vi Capsular Polysaccharide-Protein Conjugate Vaccines*, Infect. Immun. 62(10):4440-4444, 1994.

Walden et al., *Analytical procedures for quantification of peptides in pharmaceutical research by liquid chromatography—mass spectrometry*, Analytical and Bioanalytical Chem., 378:883-897, 2004.

Walensky et al., *Activation of Apoptosis in Vivo by a Hydrocarbon-Stapled BH3 Helix*, Science, 305(5689):1466-1470, 2004.

Walensky et al. *A Stapled BID BH3 Helix Directly Binds and Activates BAX*, Molecular Cell, 34:199-210, 2006.

Wilen, S. H., et al., *Strategies in Optical Resolutions*, Tetrahedron 33:2725-2736, 1977.

Williams et al. *Asymmetric Synthesis of Monosubstituted and a,a-Disubstituted a-Amino Acids via Diastereoselective Glycine Enolate Alkylations*, J. Am. Chem. Soc., 113:9276-9286, 1991.

Williams et al., *Efficient Asymmetric Synthesis of N-tert-butoxycarbonyl α-Aminoacids Using 4-tert-butoxycarbonyl- 5,6-diphenylmorpholin-2-One: (R)-(N-tert-butoxycarbonyl)allylglycine [(4-Pentenoic acid, 2-[[(1,1-dimethylethoxy)carbonyl]amino]-, (2R)-)]*, Org. Synth., 80:31-37, 2003.

EPO Extended European Search Report for EP App No. 12861273.6, dated Jun. 29, 2016 (8 pages).

Bird et al., *Mucosal delivery of a double-stapled RSV peptide prevents nasopulmonary infection*, J. Clin. Invest. 124(5):2113-2124 (May 2014).

International Search Report for PCT/US2012/072315 dated Apr. 16, 2013. 6 pages.

\* cited by examiner

FIG. 1A
```
HR1: IASGIAVSKVLHEGEVNKIKNALLSTNKAVVSLSNGVSVLTSKVLDLKNYINNRL
HR2:     SDEFDASISQVNEKINQSLAFIRRSDELLHNVNTGKSTTN
```
FIG. 1B
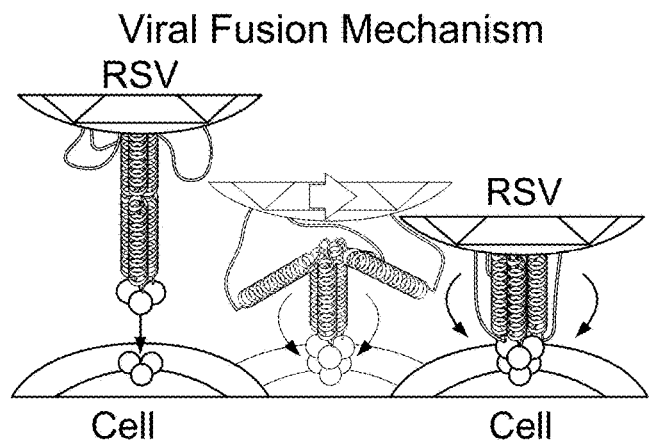
Viral Fusion Mechanism
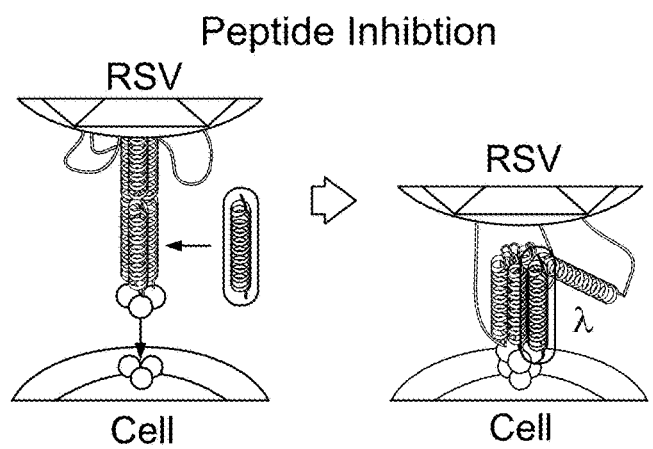
Peptide Inhibtion
FIG. 1C Hydrophobic Interaction Face

FDASISQVNEKINQSLAFIRKSDELLHNVNAGKST 35

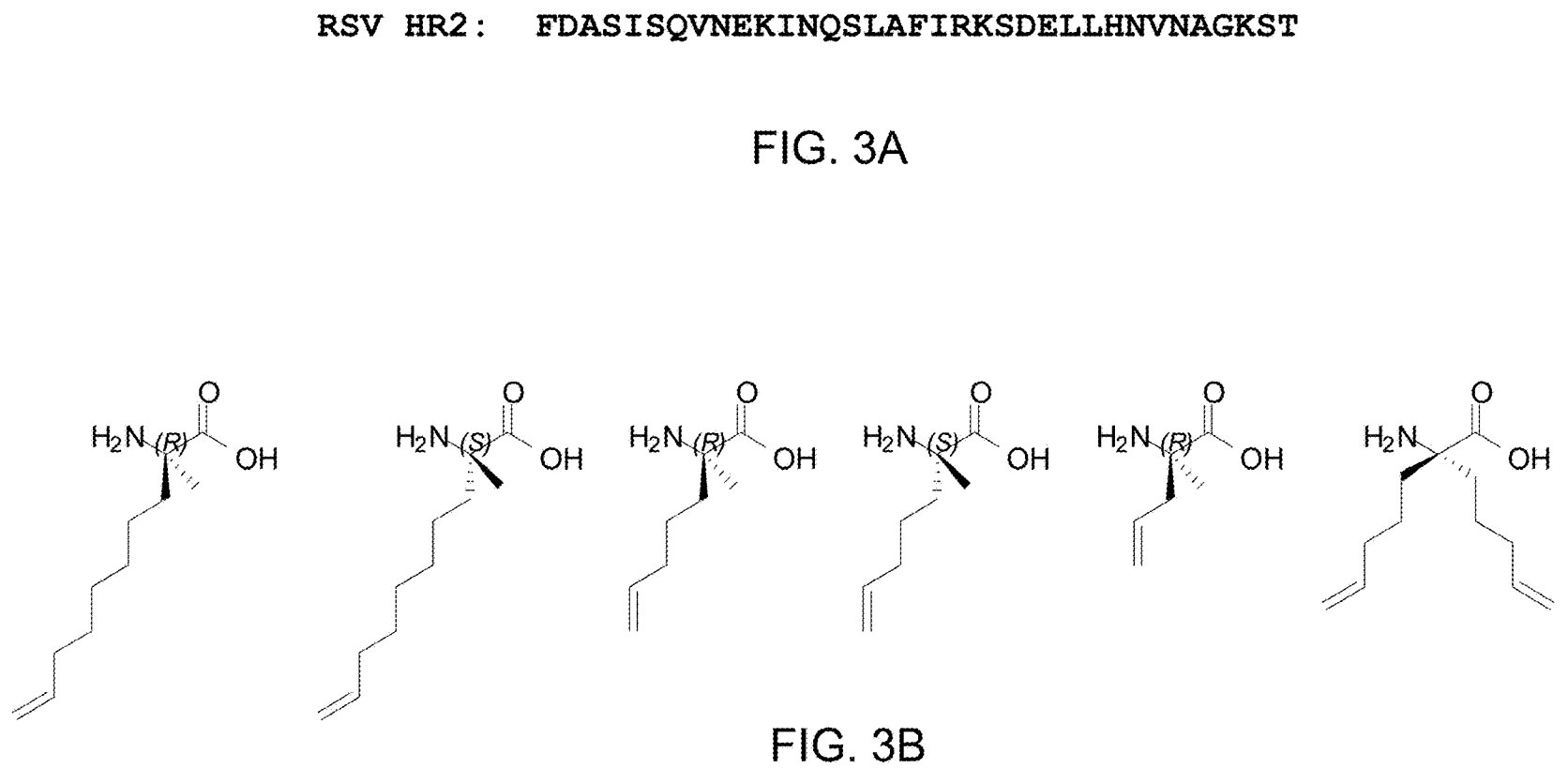

RSV HR2: FDASISQVNEKINQSLAFIRKSDELLHNV

```
RSV HR2    FDASISQVNEKINQSLAFIRKSDELLHNVNAGKST
SAHF-A     FXASIXQVNEKINQSLAFIRKSDELLHNVNAGKST
SAHF-B     FDXSISXVNEKINQSLAFIRKSDELLHNVNAGKST
SAHF-C     FDAXISQXNEKINQSLAFIRKSDELLHNVNAGKST
SAHF-D     FDASISQVNEKINQSLAFIRKSXELLXNVNAGKST
SAHF-E     FDASISQVNEKINQSLAFIRKSDXLLHXVNAGKST
SAHF-F     FDASISQVNEKINQSLAFIRKSDEXLHNXNAGKST
SAHF-G     F8ASISQVXEKINQSLAFIRKSDELLHNVNAGKST
SAHF-H     FD8SISQVNXKINQSLAFIRKSDELLHNVNAGKST
SAHF-I     FDA8ISQVNEXINQSLAFIRKSDELLHNVNAGKST
SAHF-J     FDASISQVNEKINQSLAFI8KSDELLXNVNAGKST
SAHF-K     FDASISQVNEKINQSLAFIR8SDELLHXVNAGKST
SAHF-L     FDASISQVNEKINQSLAFIRK8DELLHNXNAGKST
SAHF-M     FDASISQVNEKINQSLAFIRKS8ELLHNVXAGKST
SAHF-N     FDASISQVNEKINQSLAFIRKSD8LLHNVNXGKST
SAHF-O     FDASISQVNEKINQSLAFIRKSDE8LHNVNAXKST
```

| | Peptide | IC50 | 95% CI |
|---|---|---|---|
| —○— | RSV HR2 | 123 | 95-160 |
| —⊙— | SAHF-A | 144 | 104-199 |
| —□— | SAHF-B | 198 | 144-240 |
| —■— | SAHF-C | 250 | 189-328 |
| —◇— | SAHF-D | 1310 | 1012-1684 |
| —◆— | SAHF-E | 312 | 243-400 |
| —☆— | SAHF-F | 742 | 534-1032 |
| —★— | SAHF-G | 40 | 25-64 |
| —△— | SAHF-H | 34 | 27-43 |
| —▲— | SAHF-I | 24 | 18-33 |
| —▽— | SAHF-J | 48 | 35-65 |
| —▼— | SAHF-K | 52 | 44-60 |
| —○— | SAHF-L | 494000 | N/A |
| —⊙— | SAHF-M | 2120 | 1597-2813 |
| —×— | SAHF-N | 75 | 60-93 |
| —✳— | SAHF-O | 569 | 447-723 |

FIG. 5

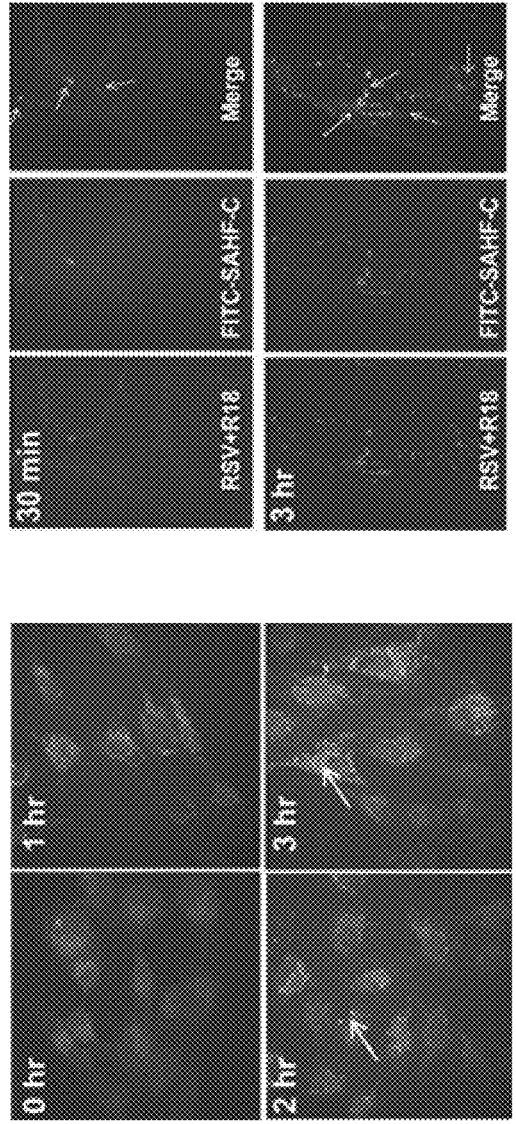
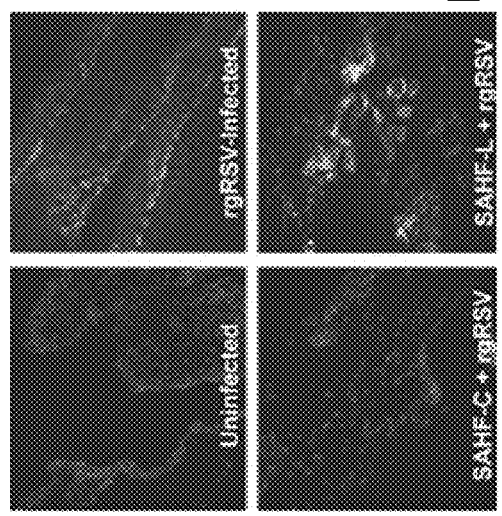
FIG. 6A
FIG. 6B
FIG. 6C

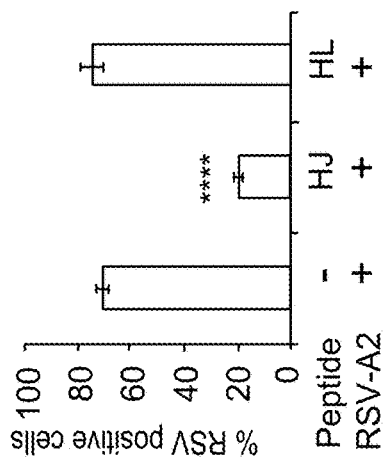
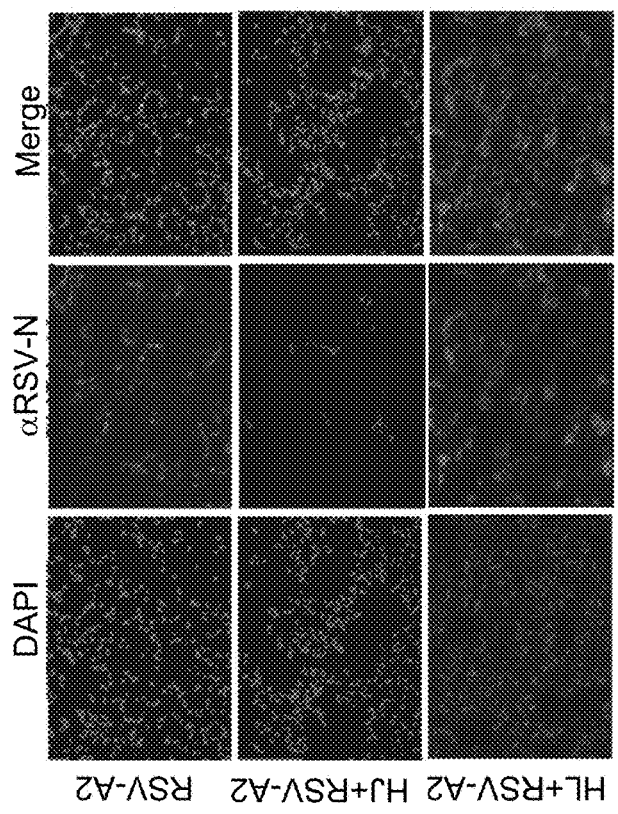
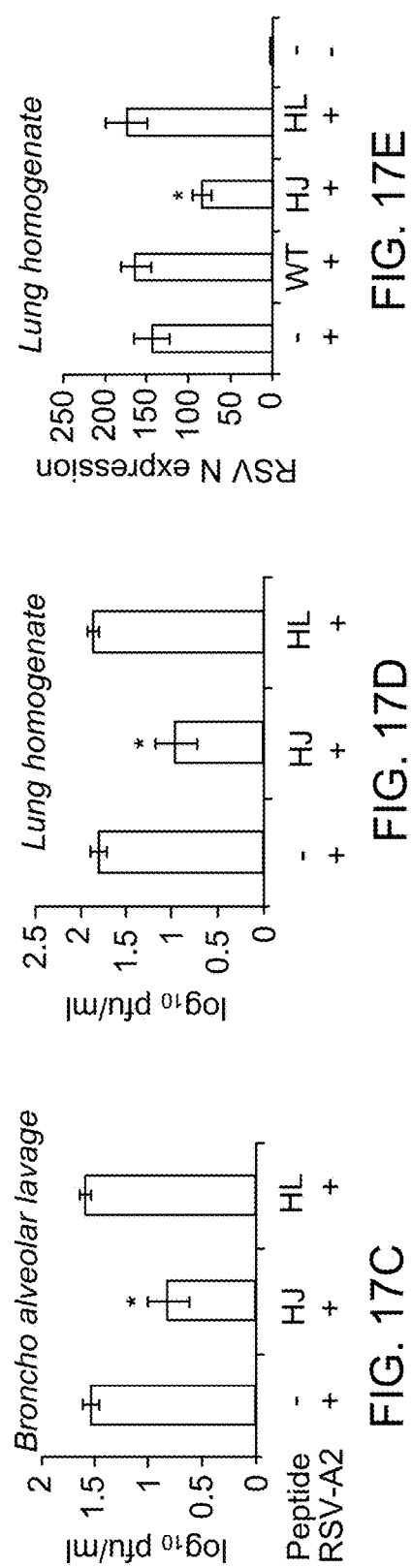
FIG. 17A
FIG. 17B
FIG. 17C
FIG. 17D
FIG. 17E

FD(R₈)SISQVN(S₅)KINQSLAFI(R₈)KSDELL(S₅)NVNAGKST

SEQUENCE LISTING

<160> NUMBER OF SEQ ID NOS: 31

<210> SEQ ID NO 1
<211> LENGTH: 35
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (1)..(1)
<223> OTHER INFORMATION: Phe or a conservative amino acid substitution
<220> FEATURE:
<221> NAME/KEY: MOD_RES
<222> LOCATION: (2)..(2)
<223> OTHER INFORMATION: Asp or any amino acid
<220> FEATURE:
<221> NAME/KEY: MOD_RES
<222> LOCATION: (3)..(3)
<223> OTHER INFORMATION: Ala or Ser or any amino acid
<220> FEATURE:
<221> NAME/KEY: MOD_RES
<222> LOCATION: (4)..(4)
<223> OTHER INFORMATION: Ser or a conservative amino acid substitution
<220> FEATURE:
<221> NAME/KEY: MOD_RES
<222> LOCATION: (5)..(5)
<223> OTHER INFORMATION: Ile or a conservative amino acid substitution
<220> FEATURE:
<221> NAME/KEY: MOD_RES
<222> LOCATION: (6)..(6)
<223> OTHER INFORMATION: Ser or any amino acid
<220> FEATURE:
<221> NAME/KEY: MOD_RES
<222> LOCATION: (7)..(7)
<223> OTHER INFORMATION: Gln or any amino acid
<220> FEATURE:
<221> NAME/KEY: MOD_RES
<222> LOCATION: (8)..(8)
<223> OTHER INFORMATION: Val or Ile or a conservative amino acid substitution
<220> FEATURE:
<221> NAME/KEY: MOD_RES
<222> LOCATION: (9)..(9)
<223> OTHER INFORMATION: Asn or any amino acid
<220> FEATURE:
<221> NAME/KEY: MOD_RES
<222> LOCATION: (10)..(10)
<223> OTHER INFORMATION: Glu or any amino acid
<220> FEATURE:

```
<221> NAME/KEY: MOD_RES
<222> LOCATION: (11)..(11)
<223> OTHER INFORMATION: Lys or a conservative amino acid substitution
<220> FEATURE:
<221> NAME/KEY: MOD_RES
<222> LOCATION: (12)..(12)
<223> OTHER INFORMATION: Ile or a conservative amino acid substitution
<220> FEATURE:
<221> NAME/KEY: MOD_RES
<222> LOCATION: (13)..(13)
<223> OTHER INFORMATION: Asn or any amino acid
<220> FEATURE:
<221> NAME/KEY: MOD_RES
<222> LOCATION: (14)..(14)
<223> OTHER INFORMATION: Gln or any amino acid
<220> FEATURE:
<221> NAME/KEY: MOD_RES
<222> LOCATION: (15)..(15)
<223> OTHER INFORMATION: Ser or a conservative amino acid substitution
<220> FEATURE:
<221> NAME/KEY: MOD_RES
<222> LOCATION: (16)..(16)
<223> OTHER INFORMATION: Leu or a conservative amino acid substitution
<220> FEATURE:
<221> NAME/KEY: MOD_RES
<222> LOCATION: (17)..(17)
<223> OTHER INFORMATION: Ala or any amino acid
<220> FEATURE:
<221> NAME/KEY: MOD_RES
<222> LOCATION: (18)..(18)
<223> OTHER INFORMATION: Phe or a conservative amino acid substitution
<220> FEATURE:
<221> NAME/KEY: MOD_RES
<222> LOCATION: (19)..(19)
<223> OTHER INFORMATION: Ile or a conservative amino acid substitution
<220> FEATURE:
<221> NAME/KEY: MOD_RES
<222> LOCATION: (20)..(20)
<223> OTHER INFORMATION: Arg or any amino acid
<220> FEATURE:
<221> NAME/KEY: MOD_RES
<222> LOCATION: (21)..(21)
<223> OTHER INFORMATION: Lys or Arg or any amino acid
<220> FEATURE:
<221> NAME/KEY: MOD_RES
<222> LOCATION: (22)..(22)
<223> OTHER INFORMATION: Ser or a conservative amino acid substitution
<220> FEATURE:
<221> NAME/KEY: MOD_RES
<222> LOCATION: (23)..(23)
<223> OTHER INFORMATION: Asp or Asn or a conservative amino acid
      substitution
<220> FEATURE:
<221> NAME/KEY: MOD_RES
<222> LOCATION: (24)..(24)
<223> OTHER INFORMATION: Glu or any amino acid
<220> FEATURE:
<221> NAME/KEY: MOD_RES
<222> LOCATION: (25)..(26)
<223> OTHER INFORMATION: Leu or a conservative amino acid substitution
<220> FEATURE:
<221> NAME/KEY: MOD_RES
<222> LOCATION: (27)..(27)
<223> OTHER INFORMATION: His or any amino acid
<220> FEATURE:
<221> NAME/KEY: MOD_RES
<222> LOCATION: (28)..(28)
<223> OTHER INFORMATION: Asn or His or any amino acid
<220> FEATURE:
<221> NAME/KEY: MOD_RES
<222> LOCATION: (29)..(29)
<223> OTHER INFORMATION: Val or Ile or a conservative amino acid
      substitution
<220> FEATURE:
<221> NAME/KEY: MOD_RES
<222> LOCATION: (30)..(30)
<223> OTHER INFORMATION: Asn or a conservative amino acid substitution
<220> FEATURE:
<221> NAME/KEY: MOD_RES
```

```
<222> LOCATION: (31)..(31)
<223> OTHER INFORMATION: Ala, Val or Thr or any amino acid
<220> FEATURE:
<221> NAME/KEY: MOD_RES
<222> LOCATION: (32)..(32)
<223> OTHER INFORMATION: Gly or a conservative amino acid substitution
<220> FEATURE:
<221> NAME/KEY: MOD_RES
<222> LOCATION: (33)..(33)
<223> OTHER INFORMATION: Lys or a conservative amino acid substitution
<220> FEATURE:
<221> NAME/KEY: MOD_RES
<222> LOCATION: (34)..(34)
<223> OTHER INFORMATION: Ser or any amino acid
<220> FEATURE:
<221> NAME/KEY: MOD_RES
<222> LOCATION: (35)..(35)
<223> OTHER INFORMATION: Thr or any amino acid
<220> FEATURE:
<223> OTHER INFORMATION: see specification as filed for detailed
      description of
      substitutions and preferred embodiments

<400> SEQUENCE: 1

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa
        35

<210> SEQ ID NO 2
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Phe Asp Ala Ser Ile Ser Gln Val Asn Glu Lys Ile Asn Gln Ser Leu
1               5                   10                  15

Ala Phe Ile Arg Lys Ser Asp Glu Leu Leu His Asn Val Asn Ala Gly
            20                  25                  30

Lys Ser Thr
        35

<210> SEQ ID NO 3
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: misc_feature
<222> LOCATION: (2)..(6)
<223> OTHER INFORMATION: Crosslink between residues
<220> FEATURE:
<221> NAME/KEY: MOD_RES
<222> LOCATION: (6)..(6)
<223> OTHER INFORMATION: Any amino acid

<400> SEQUENCE: 3

Phe Xaa Ala Ser Ile Xaa Gln Val Asn Glu Lys Ile Asn Gln Ser Leu
1               5                   10                  15
```

```
Ala Phe Ile Arg Lys Ser Asp Glu Leu Leu His Asn Val Asn Ala Gly
            20                  25                  30

Lys Ser Thr
        35

<210> SEQ ID NO 4
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Any amino acid
<220> FEATURE:
<221> NAME/KEY: misc_feature
<222> LOCATION: (3)..(7)
<223> OTHER INFORMATION: Crosslink between residues
<220> FEATURE:
<221> NAME/KEY: MOD_RES
<222> LOCATION: (7)..(7)
<223> OTHER INFORMATION: Any amino acid

<400> SEQUENCE: 4

Phe Asp Xaa Ser Ile Ser Xaa Val Asn Glu Lys Ile Asn Gln Ser Leu
1               5                   10                  15

Ala Phe Ile Arg Lys Ser Asp Glu Leu Leu His Asn Val Asn Ala Gly
            20                  25                  30

Lys Ser Thr
        35

<210> SEQ ID NO 5
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Any amino acid
<220> FEATURE:
<221> NAME/KEY: misc_feature
<222> LOCATION: (4)..(8)
<223> OTHER INFORMATION: Crosslink between residues
<220> FEATURE:
<221> NAME/KEY: MOD_RES
<222> LOCATION: (8)..(8)
<223> OTHER INFORMATION: Any amino acid

<400> SEQUENCE: 5

Phe Asp Ala Xaa Ile Ser Gln Xaa Asn Glu Lys Ile Asn Gln Ser Leu
1               5                   10                  15

Ala Phe Ile Arg Lys Ser Asp Glu Leu Leu His Asn Val Asn Ala Gly
            20                  25                  30

Lys Ser Thr
        35

<210> SEQ ID NO 6
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
```

```
<220> FEATURE:
<221> NAME/KEY: MOD_RES
<222> LOCATION: (23)..(23)
<223> OTHER INFORMATION: Any amino acid
<220> FEATURE:
<221> NAME/KEY: misc_feature
<222> LOCATION: (23)..(27)
<223> OTHER INFORMATION: Crosslink between residues
<220> FEATURE:
<221> NAME/KEY: MOD_RES
<222> LOCATION: (27)..(27)
<223> OTHER INFORMATION: Any amino acid

<400> SEQUENCE: 6

Phe Asp Ala Ser Ile Ser Gln Val Asn Glu Lys Ile Asn Gln Ser Leu
1               5                   10                  15

Ala Phe Ile Arg Lys Ser Xaa Glu Leu Leu Xaa Asn Val Asn Ala Gly
            20                  25                  30

Lys Ser Thr
        35

<210> SEQ ID NO 7
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Any amino acid
<220> FEATURE:
<221> NAME/KEY: misc_feature
<222> LOCATION: (4)..(8)
<223> OTHER INFORMATION: Crosslink between residues
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (23)..(23)
<223> OTHER INFORMATION: Any amino acid
<220> FEATURE:
<221> NAME/KEY: misc_feature
<222> LOCATION: (23)..(27)
<223> OTHER INFORMATION: Crosslink between residues
<220> FEATURE:
<221> NAME/KEY: MOD_RES
<222> LOCATION: (27)..(27)
<223> OTHER INFORMATION: Any amino acid

<400> SEQUENCE: 7

Phe Asp Ala Xaa Ile Ser Gln Xaa Asn Glu Lys Ile Asn Gln Ser Leu
1               5                   10                  15

Ala Phe Ile Arg Lys Ser Xaa Glu Leu Leu Xaa Asn Val Asn Ala Gly
            20                  25                  30

Lys Ser Thr
        35

<210> SEQ ID NO 8
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (24)..(24)
```

```
<223> OTHER INFORMATION: Any amino acid
<220> FEATURE:
<221> NAME/KEY: misc_feature
<222> LOCATION: (24)..(28)
<223> OTHER INFORMATION: Crosslink between residues
<220> FEATURE:
<221> NAME/KEY: MOD_RES
<222> LOCATION: (28)..(28)
<223> OTHER INFORMATION: Any amino acid

<400> SEQUENCE: 8

Phe Asp Ala Ser Ile Ser Gln Val Asn Glu Lys Ile Asn Gln Ser Leu
1               5                   10                  15

Ala Phe Ile Arg Lys Ser Asp Xaa Leu Leu His Xaa Val Asn Ala Gly
            20                  25                  30

Lys Ser Thr
        35

<210> SEQ ID NO 9
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (25)..(25)
<223> OTHER INFORMATION: Any amino acid
<220> FEATURE:
<221> NAME/KEY: misc_feature
<222> LOCATION: (25)..(29)
<223> OTHER INFORMATION: Crosslink between residues
<220> FEATURE:
<221> NAME/KEY: MOD_RES
<222> LOCATION: (29)..(29)
<223> OTHER INFORMATION: Any amino acid

<400> SEQUENCE: 9

Phe Asp Ala Ser Ile Ser Gln Val Asn Glu Lys Ile Asn Gln Ser Leu
1               5                   10                  15

Ala Phe Ile Arg Lys Ser Asp Glu Xaa Leu His Asn Xaa Asn Ala Gly
            20                  25                  30

Lys Ser Thr
        35

<210> SEQ ID NO 10
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: misc_feature
<222> LOCATION: (2)..(9)
<223> OTHER INFORMATION: Crosslink between residues
<220> FEATURE:
<221> NAME/KEY: MOD_RES
<222> LOCATION: (9)..(9)
<223> OTHER INFORMATION: Any amino acid

<400> SEQUENCE: 10

Phe Xaa Ala Ser Ile Ser Gln Val Xaa Glu Lys Ile Asn Gln Ser Leu
1               5                   10                  15
```

Ala Phe Ile Arg Lys Ser Asp Glu Leu Leu His Asn Val Asn Ala Gly
            20                  25                  30

Lys Ser Thr
        35

<210> SEQ ID NO 11
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Any amino acid
<220> FEATURE:
<221> NAME/KEY: misc_feature
<222> LOCATION: (3)..(10)
<223> OTHER INFORMATION: Crosslink between residues
<220> FEATURE:
<221> NAME/KEY: MOD_RES
<222> LOCATION: (10)..(10)
<223> OTHER INFORMATION: Any amino acid

<400> SEQUENCE: 11

Phe Asp Xaa Ser Ile Ser Gln Val Asn Xaa Lys Ile Asn Gln Ser Leu
1               5                   10                  15

Ala Phe Ile Arg Lys Ser Asp Glu Leu Leu His Asn Val Asn Ala Gly
            20                  25                  30

Lys Ser Thr
        35

<210> SEQ ID NO 12
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Any amino acid
<220> FEATURE:
<221> NAME/KEY: misc_feature
<222> LOCATION: (4)..(11)
<223> OTHER INFORMATION: Crosslink between residues
<220> FEATURE:
<221> NAME/KEY: MOD_RES
<222> LOCATION: (11)..(11)
<223> OTHER INFORMATION: Any amino acid

<400> SEQUENCE: 12

Phe Asp Ala Xaa Ile Ser Gln Val Asn Glu Xaa Ile Asn Gln Ser Leu
1               5                   10                  15

Ala Phe Ile Arg Lys Ser Asp Glu Leu Leu His Asn Val Asn Ala Gly
            20                  25                  30

Lys Ser Thr
        35

<210> SEQ ID NO 13
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:

-continued

```
<221> NAME/KEY: MOD_RES
<222> LOCATION: (20)..(20)
<223> OTHER INFORMATION: Any amino acid
<220> FEATURE:
<221> NAME/KEY: misc_feature
<222> LOCATION: (20)..(27)
<223> OTHER INFORMATION: Crosslink between residues
<220> FEATURE:
<221> NAME/KEY: MOD_RES
<222> LOCATION: (27)..(27)
<223> OTHER INFORMATION: Any amino acid

<400> SEQUENCE: 13

Phe Asp Ala Ser Ile Ser Gln Val Asn Glu Lys Ile Asn Gln Ser Leu
1               5                   10                  15

Ala Phe Ile Xaa Lys Ser Asp Glu Leu Leu Xaa Asn Val Asn Ala Gly
            20                  25                  30

Lys Ser Thr
        35

<210> SEQ ID NO 14
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (21)..(21)
<223> OTHER INFORMATION: Any amino acid
<220> FEATURE:
<221> NAME/KEY: misc_feature
<222> LOCATION: (21)..(28)
<223> OTHER INFORMATION: Crosslink between residues
<220> FEATURE:
<221> NAME/KEY: MOD_RES
<222> LOCATION: (28)..(28)
<223> OTHER INFORMATION: Any amino acid

<400> SEQUENCE: 14

Phe Asp Ala Ser Ile Ser Gln Val Asn Glu Lys Ile Asn Gln Ser Leu
1               5                   10                  15

Ala Phe Ile Arg Xaa Ser Asp Glu Leu Leu His Xaa Val Asn Ala Gly
            20                  25                  30

Lys Ser Thr
        35

<210> SEQ ID NO 15
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (22)..(22)
<223> OTHER INFORMATION: Any amino acid
<220> FEATURE:
<221> NAME/KEY: misc_feature
<222> LOCATION: (22)..(29)
<223> OTHER INFORMATION: Crosslink between residues
<220> FEATURE:
<221> NAME/KEY: MOD_RES
<222> LOCATION: (29)..(29)
<223> OTHER INFORMATION: Any amino acid

<400> SEQUENCE: 15

Phe Asp Ala Ser Ile Ser Gln Val Asn Glu Lys Ile Asn Gln Ser Leu
```

```
                1               5                  10                  15
Ala Phe Ile Arg Lys Xaa Asp Glu Leu Leu His Asn Xaa Asn Ala Gly
            20                  25                  30

Lys Ser Thr
        35

<210> SEQ ID NO 16
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (23)..(23)
<223> OTHER INFORMATION: Any amino acid
<220> FEATURE:
<221> NAME/KEY: misc_feature
<222> LOCATION: (23)..(30)
<223> OTHER INFORMATION: Crosslink between residues
<220> FEATURE:
<221> NAME/KEY: MOD_RES
<222> LOCATION: (30)..(30)
<223> OTHER INFORMATION: Any amino acid

<400> SEQUENCE: 16

Phe Asp Ala Ser Ile Ser Gln Val Asn Glu Lys Ile Asn Gln Ser Leu
1               5                   10                  15

Ala Phe Ile Arg Lys Ser Xaa Glu Leu Leu His Asn Val Xaa Ala Gly
            20                  25                  30

Lys Ser Thr
        35

<210> SEQ ID NO 17
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (24)..(24)
<223> OTHER INFORMATION: Any amino acid
<220> FEATURE:
<221> NAME/KEY: misc_feature
<222> LOCATION: (24)..(31)
<223> OTHER INFORMATION: Crosslink between residues
<220> FEATURE:
<221> NAME/KEY: MOD_RES
<222> LOCATION: (31)..(31)
<223> OTHER INFORMATION: Any amino acid

<400> SEQUENCE: 17

Phe Asp Ala Ser Ile Ser Gln Val Asn Glu Lys Ile Asn Gln Ser Leu
1               5                   10                  15

Ala Phe Ile Arg Lys Ser Asp Xaa Leu Leu His Asn Val Asn Xaa Gly
            20                  25                  30

Lys Ser Thr
        35

<210> SEQ ID NO 18
<211> LENGTH: 35
<212> TYPE: PRT
<213> ORGANISM: Artificial Sequence
<220> FEATURE:
<223> OTHER INFORMATION: Description of Artificial Sequence: Synthetic
```

```
      polypeptide
<220> FEATURE:
<221> NAME/KEY: MOD_RES
<222> LOCATION: (25)..(25)
<223> OTHER INFORMATION: Any amino acid
<220> FEATURE:
<221> NAME/KEY: misc_feature
<222> LOCATION: (25)..(32)
<223> OTHER INFORMATION: Crosslink between residues
<220> FEATURE:
<221> NAME/KEY: MOD_RES
<222> LOCATION: (32)..(32)
<223> OTHER INFORMATION: Any amino acid

<400> SEQUENCE: 18

Phe Asp Ala Ser Ile Ser Gln Val Asn Glu Lys Ile Asn Gln Ser Leu
1               5                   10                  15

Ala Phe Ile Arg Lys Ser Asp Glu Xaa Leu His Asn Val Asn Ala Xaa
            20                  25                  30

Lys Ser Thr
        35

<210> SEQ ID NO 19
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: misc_feature
<222> LOCATION: (2)..(9)
<223> OTHER INFORMATION: Crosslink between residues
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (20)..(20)
<223> OTHER INFORMATION: Any amino acid
<220> FEATURE:
<221> NAME/KEY: misc_feature
<222> LOCATION: (20)..(27)
<223> OTHER INFORMATION: Crosslink between residues
<220> FEATURE:
<221> NAME/KEY: MOD_RES
<222> LOCATION: (27)..(27)
<223> OTHER INFORMATION: Any amino acid

<400> SEQUENCE: 19

Phe Xaa Ala Ser Ile Ser Gln Val Xaa Glu Lys Ile Asn Gln Ser Leu
1               5                   10                  15

Ala Phe Ile Xaa Lys Ser Asp Glu Leu Leu Xaa Asn Val Asn Ala Gly
            20                  25                  30

Lys Ser Thr
        35

<210> SEQ ID NO 20
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
```

```
<222> LOCATION: (3)..(3)
<223> OTHER INFORMATION: Any amino acid
<220> FEATURE:
<221> NAME/KEY: misc_feature
<222> LOCATION: (3)..(10)
<223> OTHER INFORMATION: Crosslink between residues
<220> FEATURE:
<221> NAME/KEY: MOD_RES
<222> LOCATION: (10)..(10)
<223> OTHER INFORMATION: Any amino acid
<220> FEATURE:
<221> NAME/KEY: MOD_RES
<222> LOCATION: (20)..(20)
<223> OTHER INFORMATION: Any amino acid
<220> FEATURE:
<221> NAME/KEY: misc_feature
<222> LOCATION: (20)..(27)
<223> OTHER INFORMATION: Crosslink between residues
<220> FEATURE:
<221> NAME/KEY: MOD_RES
<222> LOCATION: (27)..(27)
<223> OTHER INFORMATION: Any amino acid

<400> SEQUENCE: 20

Phe Asp Xaa Ser Ile Ser Gln Val Asn Xaa Lys Ile Asn Gln Ser Leu
1               5                   10                  15

Ala Phe Ile Xaa Lys Ser Asp Glu Leu Leu Xaa Asn Val Asn Ala Gly
            20                  25                  30

Lys Ser Thr
        35

<210> SEQ ID NO 21
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Any amino acid
<220> FEATURE:
<221> NAME/KEY: misc_feature
<222> LOCATION: (4)..(11)
<223> OTHER INFORMATION: Crosslink between residues
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (20)..(20)
<223> OTHER INFORMATION: Any amino acid
<220> FEATURE:
<221> NAME/KEY: misc_feature
<222> LOCATION: (20)..(27)
<223> OTHER INFORMATION: Crosslink between residues
<220> FEATURE:
<221> NAME/KEY: MOD_RES
<222> LOCATION: (27)..(27)
<223> OTHER INFORMATION: Any amino acid

<400> SEQUENCE: 21

Phe Asp Ala Xaa Ile Ser Gln Val Asn Glu Xaa Ile Asn Gln Ser Leu
1               5                   10                  15

Ala Phe Ile Xaa Lys Ser Asp Glu Leu Leu Xaa Asn Val Asn Ala Gly
            20                  25                  30

Lys Ser Thr
        35
```

<210> SEQ ID NO 22
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: misc_feature
<222> LOCATION: (2)..(9)
<223> OTHER INFORMATION: Crosslink between residues
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (21)..(21)
<223> OTHER INFORMATION: Any amino acid
<220> FEATURE:
<221> NAME/KEY: misc_feature
<222> LOCATION: (21)..(28)
<223> OTHER INFORMATION: Crosslink between residues
<220> FEATURE:
<221> NAME/KEY: MOD_RES
<222> LOCATION: (28)..(28)
<223> OTHER INFORMATION: Any amino acid

<400> SEQUENCE: 22

Phe Xaa Ala Ser Ile Ser Gln Val Xaa Glu Lys Ile Asn Gln Ser Leu
1               5                   10                  15

Ala Phe Ile Arg Xaa Ser Asp Glu Leu Leu His Xaa Val Asn Ala Gly
            20                  25                  30

Lys Ser Thr
        35

<210> SEQ ID NO 23
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Any amino acid
<220> FEATURE:
<221> NAME/KEY: misc_feature
<222> LOCATION: (3)..(10)
<223> OTHER INFORMATION: Crosslink between residues
<220> FEATURE:
<221> NAME/KEY: MOD_RES
<222> LOCATION: (10)..(10)
<223> OTHER INFORMATION: Any amino acid
<220> FEATURE:
<221> NAME/KEY: MOD_RES
<222> LOCATION: (21)..(21)
<223> OTHER INFORMATION: Any amino acid
<220> FEATURE:
<221> NAME/KEY: misc_feature
<222> LOCATION: (21)..(28)
<223> OTHER INFORMATION: Crosslink between residues
<220> FEATURE:
<221> NAME/KEY: MOD_RES
<222> LOCATION: (28)..(28)
<223> OTHER INFORMATION: Any amino acid

<400> SEQUENCE: 23

Phe Asp Xaa Ser Ile Ser Gln Val Asn Xaa Lys Ile Asn Gln Ser Leu

```
1               5                  10                 15
Ala Phe Ile Arg Xaa Ser Asp Glu Leu Leu His Xaa Val Asn Ala Gly
            20                  25                 30

Lys Ser Thr
        35

<210> SEQ ID NO 24
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Any amino acid
<220> FEATURE:
<221> NAME/KEY: misc_feature
<222> LOCATION: (4)..(11)
<223> OTHER INFORMATION: Crosslink between residues
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (21)..(21)
<223> OTHER INFORMATION: Any amino acid
<220> FEATURE:
<221> NAME/KEY: misc_feature
<222> LOCATION: (21)..(28)
<223> OTHER INFORMATION: Crosslink between residues
<220> FEATURE:
<221> NAME/KEY: MOD_RES
<222> LOCATION: (28)..(28)
<223> OTHER INFORMATION: Any amino acid

<400> SEQUENCE: 24

Phe Asp Ala Xaa Ile Ser Gln Val Asn Glu Xaa Ile Asn Gln Ser Leu
1               5                  10                 15

Ala Phe Ile Arg Xaa Ser Asp Glu Leu Leu His Xaa Val Asn Ala Gly
            20                  25                 30

Lys Ser Thr
        35

<210> SEQ ID NO 25
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Any amino acid
<220> FEATURE:
<221> NAME/KEY: misc_feature
<222> LOCATION: (3)..(10)
<223> OTHER INFORMATION: Crosslink between residues
<220> FEATURE:
<221> NAME/KEY: MOD_RES
<222> LOCATION: (10)..(10)
<223> OTHER INFORMATION: Any amino acid
<220> FEATURE:
<221> NAME/KEY: MOD_RES
<222> LOCATION: (22)..(22)
<223> OTHER INFORMATION: Any amino acid
<220> FEATURE:
<221> NAME/KEY: misc_feature
<222> LOCATION: (22)..(29)
```

<223> OTHER INFORMATION: Crosslink between residues
<220> FEATURE:
<221> NAME/KEY: MOD_RES
<222> LOCATION: (29)..(29)
<223> OTHER INFORMATION: Any amino acid

<400> SEQUENCE: 25

Phe Asp Xaa Ser Ile Ser Gln Val Asn Xaa Lys Ile Asn Gln Ser Leu
1               5                   10                  15

Ala Phe Ile Arg Lys Xaa Asp Glu Leu Leu His Asn Xaa Asn Ala Gly
            20                  25                  30

Lys Ser Thr
        35

<210> SEQ ID NO 26
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Any amino acid
<220> FEATURE:
<221> NAME/KEY: misc_feature
<222> LOCATION: (4)..(11)
<223> OTHER INFORMATION: Crosslink between residues
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (22)..(22)
<223> OTHER INFORMATION: Any amino acid
<220> FEATURE:
<221> NAME/KEY: misc_feature
<222> LOCATION: (22)..(28)
<223> OTHER INFORMATION: Crosslink between residues
<220> FEATURE:
<221> NAME/KEY: MOD_RES
<222> LOCATION: (28)..(28)
<223> OTHER INFORMATION: Any amino acid

<400> SEQUENCE: 26

Phe Asp Ala Xaa Ile Ser Gln Val Asn Glu Xaa Ile Asn Gln Ser Leu
1               5                   10                  15

Ala Phe Ile Arg Lys Xaa Asp Glu Leu Leu His Xaa Val Asn Ala Gly
            20                  25                  30

Lys Ser Thr
        35

<210> SEQ ID NO 27
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Ile Ala Ser Gly Ile Ala Val Ser Lys Val Leu His Glu Gly Glu Val
1               5                   10                  15

Asn Lys Ile Lys Asn Ala Leu Leu Ser Thr Asn Lys Ala Val Val Ser
            20                  25                  30

Leu Ser Asn Gly Val Ser Val Leu Thr Ser Lys Val Leu Asp Leu Lys

-continued

```
                35                  40                  45
Asn Tyr Ile Asn Asn Arg Leu
        50                  55

<210> SEQ ID NO 28
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Ser Asp Glu Phe Asp Ala Ser Ile Ser Gln Val Asn Glu Lys Ile Asn
1               5                   10                  15

Gln Ser Leu Ala Phe Ile Arg Arg Ser Asp Glu Leu Leu His Asn Val
            20                  25                  30

Asn Thr Gly Lys Ser Thr Thr Asn
        35                  40

<210> SEQ ID NO 29
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Ala or Ser
<220> FEATURE:
<221> NAME/KEY: MOD_RES
<222> LOCATION: (8)..(8)
<223> OTHER INFORMATION: Val or Ile
<220> FEATURE:
<221> NAME/KEY: MOD_RES
<222> LOCATION: (21)..(21)
<223> OTHER INFORMATION: Lys or Arg
<220> FEATURE:
<221> NAME/KEY: MOD_RES
<222> LOCATION: (23)..(23)
<223> OTHER INFORMATION: Asp or Asn
<220> FEATURE:
<221> NAME/KEY: MOD_RES
<222> LOCATION: (28)..(28)
<223> OTHER INFORMATION: Asn or His
<220> FEATURE:
<221> NAME/KEY: MOD_RES
<222> LOCATION: (29)..(29)
<223> OTHER INFORMATION: Val or Ile
<220> FEATURE:
<221> NAME/KEY: MOD_RES
<222> LOCATION: (31)..(31)
<223> OTHER INFORMATION: Ala, Val or Thr
<220> FEATURE:
<223> OTHER INFORMATION: see specification as filed for detailed
      description of
      substitutions and preferred embodiments

<400> SEQUENCE: 29

Phe Asp Xaa Ser Ile Ser Gln Xaa Asn Glu Lys Ile Asn Gln Ser Leu
1               5                   10                  15

Ala Phe Ile Arg Xaa Ser Xaa Glu Leu Leu His Xaa Xaa Asn Xaa Gly
            20                  25                  30

Lys Ser Thr
        35

<210> SEQ ID NO 30
```

```
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Any amino acid
<220> FEATURE:
<221> NAME/KEY: misc_feature
<222> LOCATION: (4)..(11)
<223> OTHER INFORMATION: Crosslink between residues
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (22)..(22)
<223> OTHER INFORMATION: Any amino acid
<220> FEATURE:
<221> NAME/KEY: misc_feature
<222> LOCATION: (22)..(29)
<223> OTHER INFORMATION: Crosslink between residues
<220> FEATURE:
<221> NAME/KEY: MOD_RES
<222> LOCATION: (29)..(29)
<223> OTHER INFORMATION: Any amino acid

<400> SEQUENCE: 30

Phe Asp Ala Xaa Ile Ser Gln Val Asn Glu Xaa Ile Asn Gln Ser Leu
1               5                   10                  15

Ala Phe Ile Arg Lys Xaa Asp Glu Leu Leu His Asn Xaa Asn Ala Gly
            20                  25                  30

Lys Ser Thr
        35

<210> SEQ ID NO 31
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: R8 non-natural olefinic amino acid
<220> FEATURE:
<221> NAME/KEY: misc_feature
<222> LOCATION: (3)..(10)
<223> OTHER INFORMATION: Crosslink between residues
<220> FEATURE:
<221> NAME/KEY: MOD_RES
<222> LOCATION: (10)..(10)
<223> OTHER INFORMATION: S5 non-natural olefinic amino acid
<220> FEATURE:
<221> NAME/KEY: MOD_RES
<222> LOCATION: (20)..(20)
<223> OTHER INFORMATION: R8 non-natural olefinic amino acid
<220> FEATURE:
<221> NAME/KEY: misc_feature
<222> LOCATION: (20)..(27)
<223> OTHER INFORMATION: Crosslink between residues
<220> FEATURE:
<221> NAME/KEY: MOD_RES
<222> LOCATION: (27)..(27)
<223> OTHER INFORMATION: S5 non-natural olefinic amino acid
<220> FEATURE:
<223> OTHER INFORMATION: see specification as filed for detailed
      description of
      substitutions and preferred embodiments
```

```
<400> SEQUENCE: 31

Phe Asp Xaa Ser Ile Ser Gln Val Asn Xaa Lys Ile Asn Gln Ser Leu
1               5                   10                  15

Ala Phe Ile Xaa Lys Ser Asp Glu Leu Leu Xaa Asn Val Asn Ala Gly
            20                  25              30

Lys Ser Thr
        35
```

STABILIZED ANTIVIRAL FUSION HELICES

TECHNICAL FIELD

This disclosure relates to structurally stabilized therapeutic peptides related to Respiratory Syncytial Virus (RSV) and methods of using such peptides in the prophylaxis and/or treatment of Respiratory Syncytial Virus (RSV) infection.

BACKGROUND

Respiratory Syncytial Virus (RSV) infection causes 64 million cases of respiratory disease and 166,000 deaths annually worldwide. Drug resistant RSV strains have been reported (Adams et al., Clin. Infect. Disease, 51:185-188, 2010; Douglas et al., J. Virol., 49:2560-2466, 2005).

New and improved strategies for the prophylaxis and/or treatment of RSV infection are required.

SUMMARY

The present disclosure provides structurally stabilized peptides related to (e.g., sharing sequence homology with) portions or fragments of Respiratory Syncytial Virus (RSV) fusion protein (RSV-F), and methods for using such stabilized peptides as therapeutic and/or prophylactic agents.

In some aspects, the present disclosure provides internally cross-linked polypeptides comprising the amino acid sequence $A_0B_0C_0D_0E_0F_0G_0$ $A_1B_1C_1D_1E_1F_1G_1$ $A_2B_2C_2D_2E_2F_2G_2$ $A_3B_3C_3D_3E_3F_3G_3$ $A_4B_4C_4D_4E_4F_4G_4$ (SEQ ID NO:1) wherein: $A_0$ is Phe, or a conservative amino acid substitution; $B_0$ is Asp, or any amino acid (e.g., any of the naturally occurring amino acids); $C_0$ is Ala, or Ser, or any amino acid; $D_0$ is Ser, or a conservative amino acid substitution; $E_0$ is Ile, or a conservative amino acid substitution; $F_0$ is Ser, or any amino acid; $G_0$ is Gln, or any amino acid; $A_1$ is Val or Ile, or a conservative amino acid substitution; $B_1$ is Asn, or any amino acid; $C_1$ is Glu, or any amino acid; $D_1$ is Lys, or a conservative amino acid substitution; $E_1$ is Ile, or a conservative amino acid substitution; $F_1$ is Asn, or any amino acid; $G_1$ is Gln, or any amino acid; $A_2$ is Ser, or a conservative amino acid substitution; $B_2$ is Leu, or a conservative amino acid substitution; $C_2$ is Ala, or any amino acid; $D_2$ is Phe, or a conservative amino acid substitution; $E_2$ is Ile, or a conservative amino acid substitution; $F_2$ is Arg, or any amino acid; $G_2$ is Lys, or Arg, or any amino acid; $A_3$ is Ser, or a conservative amino acid substitution; $B_3$ is Asp or Asn, or a conservative amino acid substitution; $C_3$ is Glu, or any amino acid; $D_3$ is Leu, or a conservative amino acid substitution; $E_3$ is Leu, or a conservative amino acid substitution; $F_3$ is His, or any amino acid; $G_3$ is Asn or His, or any amino acid; $A_4$ is Val or Ile, or a conservative amino acid substitution; $B_4$ is Asn, or a conservative amino acid substitution; $C_4$ is Ala, Val, or Thr, or any amino acid; $D_4$ is Gly, or a conservative amino acid substitution; $E_4$ is Lys, or a conservative amino acid substitution; $F_4$ is Ser, or any amino acid; and $G_4$ is Thr, or any amino acid; wherein the side chains of two amino acids separated by two or six amino acids are replaced by an internal staple; the side chains of three amino acids are replaced by internal staples and/or an internal stitch; the side chains of four amino acids are replaced by internal staples, internal stitches, or a combination of internal staples and stitches; or the side chains of at least four amino acids are replaced by internal staples, internal stitches, or a combination of internal staples and stitches.

In some embodiments, internally cross-linked polypeptides of the disclosure include the sequence $A_0B_0C_0D_0E_0F_0G_0$ $A_1B_1C_1D_1E_1F_1G_1$ $A_2B_2C_2D_2E_2F_2G_2$ $A_3B_3C_3D_3E_3F_3G_3$ $A_4B_4C_4D_4E_4F_4G_4$ (SEQ ID NO:1), wherein: $A_0$ is Phe, $B_0$ is Asp, $C_0$ is Ala, or Ser, $D_0$ is Ser, $E_0$ is Ile, $F_0$ is Ser, $G_0$ is Gln, $A_1$ is Val or Ile, $B_1$ is Asn, $C_1$ is Glu, $D_1$ is Lys, $E_1$ is Ile, $F_1$ is Asn, $G_1$ is Gln, $A_2$ is Ser, $B_2$ is Leu, $C_2$ is Ala, $D_2$ is Phe, $E_2$ is Ile, $F_2$ is Arg, $G_2$ is Lys, or Arg, $A_3$ is Ser, $B_3$ is Asp or Asn, $C_3$ is Glu, $D_3$ is Leu, $E_3$ is Leu, $F_3$ is His, $G_3$ is Asn or His, $A_4$ is Val or Ile, $B_4$ is Asn, $C_4$ is Ala, Val, or Thr, $D_4$ is Gly, $E_4$ is Lys, $F_4$ is Ser, $G_4$ is Thr, wherein: one or more (e.g., 1, 2, 3, 4, 5, 6, 7, 8, 9, 10, 11, 12, 13, 14, 15, 16, 17, 18) of $A_0$, $D_0$, $E_0$, $A_1$, $D_1$, $E_1$, $A_2$, $B_2$, $D_2$, $E_2$, $A_3$, $B_3$, $D_3$, $E_3$, $A_4$, $B_4$, $D_4$, $E_4$, or $A_0$, $D_0$, $E_0$, $A_1$, $D_1$, $E_1$, $A_2$, $D_2$, $E_2$, $A_3$, $D_3$, $E_3$, $A_4$, $D_4$, $E_4$ are replaced by a conservative amino acid substitution that does not alter the binding face of the peptide; and/or amino acids outside residues corresponding to $A_0$, $D_0$, $E_0$, $A_1$, $D_1$, $E_1$, $A_2$, $B_2$, $D_2$, $E_2$, $A_3$, $B_3$, $D_3$, $E_3$, $A_4$, $B_4$, $D_4$, $E_4$, or $A_0$, $D_0$, $E_0$, $A_1$, $D_1$, $E_1$, $A_2$, $D_2$, $E_2$, $A_3$, $D_3$, $E_3$, $A_4$, $D_4$, $E_4$ are at least 80% (e.g., 80%, 85%, 90%, 95%, 98%, 99%, 99.5%, or 100%) identical to the sequence of SEQ ID NO:1. In some embodiments, internally cross-linked polypeptides of the disclosure include the sequence FDASISQVNEKINQSLAFIRKS-DELLHNVNAGKST (SEQ ID NO:2).

In some embodiments, internally cross-linked polypeptides of the disclosure include an internal staple replacing the side chains of two amino acids separated by two or six amino acids comprises an internal staple selected from Table 1 (FIG. 22). In some embodiments, internally cross-linked peptides are selected from the group consisting of SEQ ID NOs: 10, 11, 12, 13, 14, 15, 16, 17, and 18. In some embodiments, the internal staples and/or the internal stitch replacing the side chains of the three amino acids includes an internal stitch selected from Table 1 (FIG. 22). In some embodiments, the internal staples and/or the internal stitch replacing the side chains of the three amino acids comprises at least two internal staples. In some embodiments, the internal staples and/or the internal stitch replacing the side chains of the three amino acids comprises a combination of at least one internal staple and an internal stitch. In some embodiments, the internal stitch replaces the side chain of a first amino acid and a second and a third amino acid thereby cross-linking the first amino acid to the second and third amino acid via an internal cross-link, wherein the first and second amino acid are separated by two, three, or six amino acids, the first and the third amino acids are separated by two, three, or six amino acids, and the second and third amino acids are distinct amino acids. In some embodiments, the internal stitch replacing the side chains of the three amino acids cross-links a pair of amino acids separated by two, three, or six amino acids. In some embodiments, the side chains of the four amino acids of the internally cross-linked polypeptides of the disclosure are replaced by two distinct internal staples. In some embodiments, a first of the two distinct internal staples cross-links a first pair of amino acids separated by two, three, or six amino acids, and a second of the at least two distinct internal staples cross-links a second pair of amino acids separated by two, three, or six amino acids. In some embodiments, internally cross-linked polypeptides of the disclosure are selected from the group consisting of SEQ ID NOs: 6, 19, 20, 21, 22, 23, 24, 25, and 26. In some embodiments, internally cross-linked polypeptides of the disclosure include internal staples, internal stitches, or a combination of internal staples and internal stitches replacing the side chains of at least four amino acids, such as at least one staple and at least one stitch. In some embodiments, the at least one staple cross-links a pair of amino acids separated by two, three, or six amino acids and the at least one stitch cross-links a first amino acid to a second amino acid and a third amino acid, wherein the first and second amino acid are separated by two, three, or six amino acids, the first and the third amino acids are separated by two, three, or six amino acids, and the second and third amino acids are distinct amino acids. In some embodiments, such staples are selected from Table 1 (FIG. 22).

In some aspects, the disclosure provides pharmaceutical compositions that include one or more internally cross-linked polypeptides of the disclosure. In some embodiments, such pharmaceutical compositions can also include one or more medicaments for the treatment of RSV infection and/or the alleviation of one or more symptoms associated with RSV infection.

In some aspects, the disclosure provides immunostimulatory compositions that include at least one or more of the internally cross-linked polypeptides of the disclosure.

In some aspects, the disclosure provides kits for identifying agents that interact with RSV fusion protein. Such kits can include one or more internally cross-linked polypeptides of the disclosure and RSV fusion protein. In some embodiments, the RSV fusion protein is RSV 5-helical bundle.

In some aspects, the disclosure provides methods for treating RSV in a subject. These methods can include selecting a subject at risk of or with RSV infection; and administering to the subject an effective amount of the peptides of claims 1-16. In some embodiments, methods include assessing a level of RSV or a symptom associated with RSV in the subject before and after treatment; and continuing treatment until a decrease in the level of RSV after treatment.

In some aspects, the disclosure provides methods of immunizing a subject against RSV. Such methods can include selecting a subject at risk for RSV infection; and administering to the subject an effective amount of the peptides.

In some aspects, the disclosure provides methods for identifying agents that interact with RSV fusion protein (RSV-F). These methods can include determining a level of binding between the peptide and RSV-F (e.g., to RSV 5-helix bundle); and detecting the level of binding between the peptide and RSV-F in the presence of an agent, wherein a change in the level of binding between the one or more peptides and RSV-F (e.g., RSV 5-helix bundle) indicates that the agent is a candidate agent that binds to RSV-F. In some embodiments, these methods can include selecting the candidate agent, and optionally, administering the candidate agent to an animal model infected with RSV, e.g., to determine if the agent reduces a level of RSV infection in the animal.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 1|A depiction of the domain organization of the RSV-F protein (A), the sequence composition of the HR1 (SEQ ID NO: 27) and HR2 (SEQ ID NO: 28) fusion domains (B), and the mechanism of action of RSV-F fusion inhibitor peptides (C).

FIG. 3A|An exemplary RSV-F HR2 domain peptide sequence (SEQ ID NO: 2) that serves as the template for hydrocarbon stapling.

FIG. 3B|A variety of non-natural amino acids containing olefinic tethers that can be used to generated hydrocarbon stapled RSV-F peptides.

FIG. 4A|Sequence compositions of an exemplary panel of singly stapled Stabilized Alpha-Helices of RSV-F (SAHF) peptides (SEQ ID NOs: 2-18-see Table 2).

FIG. 4B|A circular dichroism (CD) plot showing that hydrocarbon stapling enhances the alpha-helical structure of SAHF peptides compared to the unmodified template peptide.

FIG. 5.|A bar graph showing the differential capacity of SAHF peptides to block cellular infection by GFP-labeled RSV virus with potency of anti-viral activity correlating with binding potency in RSV 5-helix bundle binding assay (FIG. 3C).

FIG. 6A-B|Images showing that an exemplary SAHF peptide is taken up by intact cells through the pinosomal pathway and colocalizes with RSV virus during cellular contact and uptake. Specifically, A) FITC-labeled SAHF-C engages the plasma membrane and is taken up by Vero cells (labeled by cytotracker red) via the pinosomal pathway, as evidenced by the gradual accumulation of FITC-SAHF-C in intracellular vesicles. (B) Colocalization of FITC SAHF-C peptide and Rhodamine (R18)-labelled RSV during cellular contact and uptake. White arrows highlight the yellow-colored sites of colocalization.

FIG. 6C|A bar graph showing that SAHF peptides inhibit RSV infection of Vero cells and are not cytotoxic.

FIG. 6D|Images demonstrating that, when administered by intranasal drop, an exemplary SAHF peptide (SAHF-C), but not the negative control peptide SAHF-L, blocks transnasal RSV infection in mice.

FIG. 7|An Illustration of an exemplary approach to designing, synthesizing, and identifying optimal SAHF constructs to target the RSV fusion apparatus, including the generation of ala scan, staple scan, and variable N- and C-terminal deletion, addition, and derivatization libraries. Singly and doubly stapled constructs, including alanine and staple scans, are used to identify optimal SAHFs for in vitro and in vivo analyses.

FIGS. 12A-12B|Photographs (A) and a bar graph (B) showing that stapled SAHF peptides can inhibit RgRSV infection of A549 cells in a sequence-dependent manner.

FIGS. 17A-17E|Photographs (A) and bar graphs (B) showing that prophylactic intranasal treatment with stapled SAHF-H, J peptide inhibits RSV-A2 lung infection in mice.

DETAILED DESCRIPTION

Figures 2A, 2B:
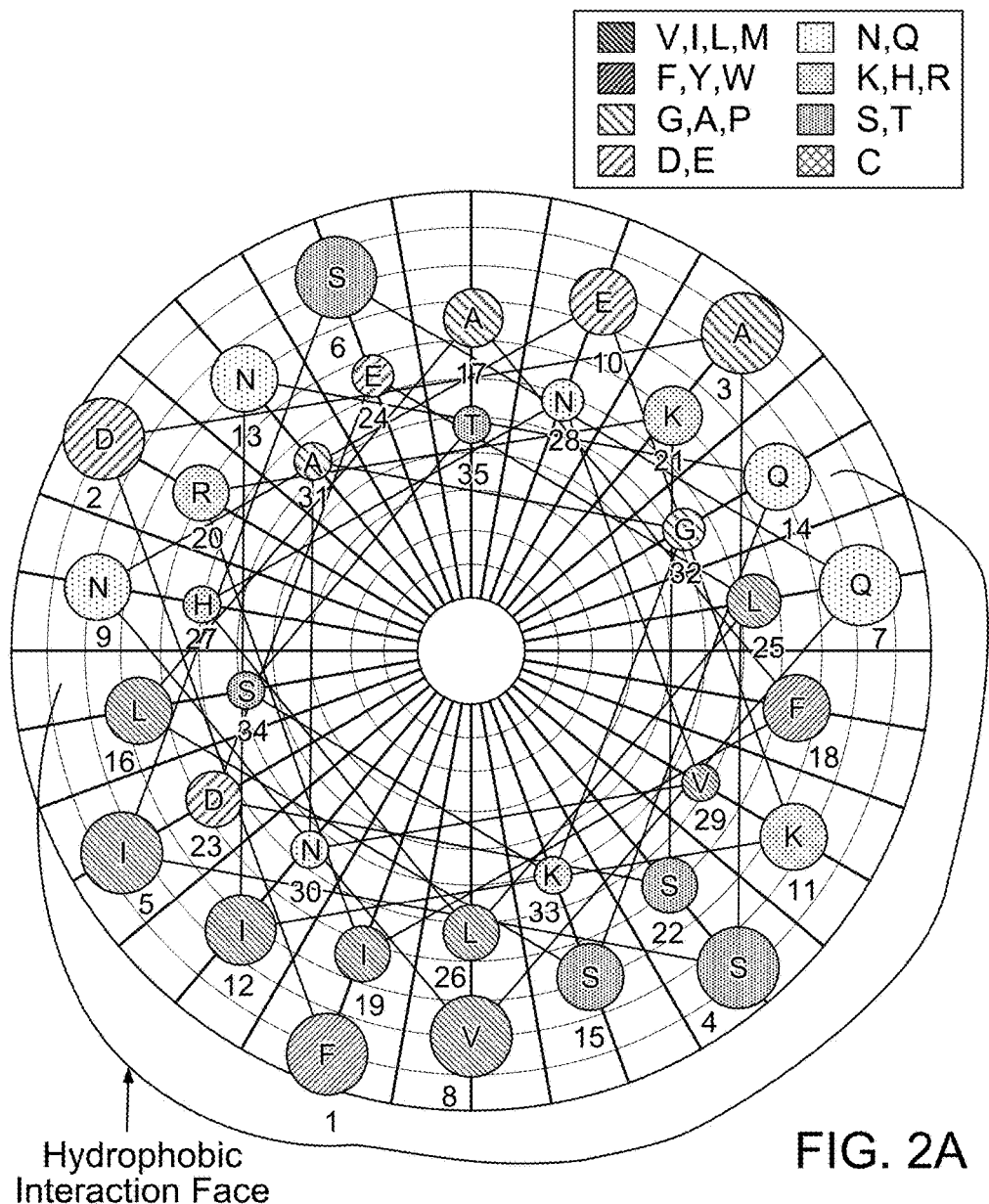
FIG. 2|(A) A helical wheel depiction of the RSV-F HR2 domain amphipathic alpha-helix (SEQ ID NO: 1), highlighting the predominantly hydrophobic binding interface, with flanking charged residues at the perimeter of the binding interface and at the non-interacting face. Charged residues are shown on the non-interacting face and predominantly hydrophobic residues are shown on the interacting face. (B) The RSV-F HR2 sequence depicted in (A) wherein amino acids shown in the interacting face are highlighted and identified by arrows.

Respiratory Syncytial Virus (RSV) infection is mediated at the cell surface by the RSV fusion protein (RSV-F). RSV most often begins as an infection in the nasal epithelial cells. Cellular infection begins with attachment of the RSV G protein to the epithelial cell. RSV deploys discrete heptad repeat domains of its fusion protein (RSV-F) to form the RSV-SFB, whose structure enables the virus to penetrate the host cell membrane. Furin-like protease cleaves the RSV-F precursor, resulting in the formation of two subunits stabilized by a disulfide bridge (Gonzalez-Reyes et al., Proc. Natl. Acad. Sci., USA, 98:9859-9864, 2003; Sugrue et al., Gen. Virol., 82:1375-1386, 2001). This cleavage also unveils an otherwise hidden peptidic fusion motif located at the N-terminus of the F1 subunit leading to formation of the FSV-F lollipop structure (Matthews et al., J. Virol., 74:5911-5920, 2000; Smith et al., Protein Eng., 15:365-371, 2002). Once the fusion peptide inserts into the host cell membrane, the F protein refolds itself to form a trimeric hairpin or "6-helix bundle." The trimeric hairpin derives from a poorly characterized conformational change that brings the C-terminal heptad repeat (HR2) region into anti-parallel assembly with the N-terminal hepad repeat (HR1), which is juxtaposed to the fusion peptide (Clanci et al., Proc. Natl. Acad. Sci., USA, 101:15046-15051, 2004). After pore opening, the HR-induced conformational change achieves a new equilibrium state believed to be essential to stabilizing and enlarging the pore (Clanci, supra, Melikyan, Retrovirology, 5:111, 2008; Melikyan et al., Proc. Natl. Acad. Sci., USA, 102:8728-8733, 2005), and penetrating the host cell. The compositions and methods disclosed herein can be used to prevent or treat RSV infection by inhibiting this process.

Stabilized Peptides

The present disclosure provides structurally stabilized peptides related to portions or fragments of RSV-F (referred to at times as stabilized α-helices of RSV or SAH-RSV) comprising at least two modified amino acids joined by an internal (intramolecular) cross-link (or staple), wherein the at least two amino acids are separated by 2, 3, or, 6 amino acids. Stabilized peptides herein include stapled and/or stitched peptides.

Amino acids are the building blocks of the peptides herein. The term "amino acid" refers to a molecule containing both an amino group and a carboxyl group. Amino acids include alpha-amino acids and beta-amino acids.

Amino acids suitable for inclusion in the peptides disclosed herein include, without limitation, natural alpha-amino acids such as D- and L-isomers of the 20 common naturally occurring alpha-amino acids found in peptides (e.g., Ala (A), Arg (R), Asn (N), Cys (C), Asp (D), Gln (O), Glu (E), Gly (G), His (H), Ile (I), leu (L), Lys (K), Met (M), Phe (F), Pro (P), Ser (S), Thr (T), Trp (W), Tyr (Y), and Val (V), unnatural alpha-amino acids (including, but not limited to α,α-disubstituted and N-alkylated amino acids), natural beta-amino acids (e.g., beta-alanine), and unnnatural beta-amino acids. Amino acids used in the construction of peptides of the present invention can be prepared by organic synthesis, or obtained by other routes, such as, for example, degradation of or isolation from a natural source.

There are many known unnatural amino acids any of which may be included in the peptides of the present invention. See for example, S. Hunt, The Non-Protein Amino Acids: In Chemistry and Biochemistry of the Amino Acids, edited by G. C. Barrett, Chapman and Hall, 1985. Some examples of unnatural amino acids are 4-hydroxyproline, desmosine, gamma-aminobutyric acid, beta-cyanoalanine, norvaline, 4-(E)-butenyl-4(R)-methyl-N-methyl-L-threonine, N-methyl-L-leucine, 1-aminocyclopropanecarboxylic acid, 1-amino-2-phenylcyclopropanecarboxylic acid, 1-aminocyclobutanecarboxylic acid, 4-aminocyclopentenecarboxylic acid, 3-aminocyclohexanecarboxylic acid, 4-piperidylacetic acid, 4-amino-1-methylpyrrole-2-carboxylic acid, 2,4-diaminobutyric acid, 2,3-diaminopropionic acid, 2,4-diaminobutyric acid, 2-aminoheptanedioic acid, 4-(aminomethyl)benzoic acid, 4-aminobenzoic acid, ortho-, meta- and para-substituted phenylalanines (e.g., substituted with —C(=O)C6H5; —CF3; —CN; -halo; —NO2; CH3), disubstituted phenylalanines, substituted tyrosines (e.g., further substituted with -Q=O)C6H5; —CF3; —CN; -halo; —NO2; CH3), and statine. Additionally, amino acids can be derivatized to include amino acid residues that are hydroxylated, phosphorylated, sulfonated, acylated, and glycosylated, to name a few.

A "peptide" or "polypeptide" comprises a polymer of amino acid residues linked together by peptide (amide) bonds. The term(s), as used herein, refers to proteins, polypeptides, and peptide of any size, structure, or function. Typically, a peptide or polypeptide will be at least three amino acids long. A peptide or polypeptide may refer to an individual protein or a collection of proteins. In some instances, peptides can include only natural amino acids, although non-natural amino acids (i.e., compounds that do not occur in nature but that can be incorporated into a polypeptide chain) and/or amino acid analogs as are known in the art may alternatively be employed. Also, one or more of the amino acids in a peptide or polypeptide may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A peptide or polypeptide may also be a single molecule or may be a multi-molecular complex, such as a protein. A peptide or polypeptide may be just a fragment of a naturally occurring protein or peptide. A peptide or polypeptide may be naturally occurring, recombinant, or synthetic, or any combination thereof "Dipeptide" refers to two covalently linked amino acids.

Peptides related to portions or fragments of RSV-F include peptides with homology to RSV-F that inherently possess or can be induced to have alpha helical secondary structure. Portions of RSV-F can include one or more heptad repeat (HR) domains, e.g., one or more RSV-F heptad repeat (HR)-1 or fragments thereof, one or more HR-2 or fragments thereof, and/or one or more HR-3 or fragments thereof.

In some instances, peptides can include (e.g., comprise, consist essentially of, or consist of) at least seven (e.g., 7, 8, 9, 10, 11, 12, 13, 14, 15, 16, 17, 18, 19, 20, 21, 22, 23, 24, 25, 26, 27, 28, 29, 30, 31, 32, 33, 34, or 35) contiguous amino acids of the following amino acid sequence:

$A_0B_0C_0D_0E_0F_0G_0$ $A_1B_1C_1D_1E_1F_1G_1A_2B_2C_2D_2E_2F_2G_2$ $A_3B_3C_3D_3E_3F_3G_3$ $A_4B_4C_4D_4E_4F_4G_4$ (SEQ ID NO:1) wherein:

$A_0$ is Phe, or a conservative amino acid substitution,
$B_0$ is Asp, or any amino acid (e.g., any of the 20 naturally occurring amino acids)
$C_0$ is Ala, or Ser, or any amino acid,
$D_0$ is Ser, or a conservative amino acid substitution,
$E_0$ is Ile, or a conservative amino acid substitution,
$F_0$ is Ser, or any amino acid,
$G_0$ is Gln, or any amino acid,
$A_1$ is Val or Ile, or a conservative amino acid substitution,
$B_1$ is Asn, or any amino acid,
$C_1$ is Glu, or any amino acid,
$D_1$ is Lys, or a conservative amino acid substitution,
$E_1$ is Ile, or a conservative amino acid substitution,
$F_1$ is Asn, or any amino acid,
$G_1$ is Gln, or any amino acid,
$A_2$ is Ser, or a conservative amino acid substitution,
$B_2$ is Leu, or a conservative amino acid substitution,
$C_2$ is Ala, or any amino acid,
$D_2$ is Phe, or a conservative amino acid substitution,
$E_2$ is Ile, or a conservative amino acid substitution,
$F_2$ is Arg, or any amino acid,
$G_2$ is Lys, or Arg, or any amino acid,
$A_3$ is Ser or a conservative amino acid substitution,
$B_3$ is Asp or Asn, or a conservative amino acid substitution,
$C_3$ is Glu, or any amino acid,
$D_3$ is Leu, or a conservative amino acid substitution,
$E_3$ is Leu, or a conservative amino acid substitution,
$F_3$ is His, or any amino acid,
$G_3$ is Asn or His, or any amino acid,
$A_4$ is Val or Ile, or a conservative amino acid substitution,
$B_4$ is Asn, or a conservative amino acid substitution,
$C_4$ is Ala, Val, or Thr, or any amino acid,
$D_4$ is Gly, or a conservative amino acid substitution,
$E_4$ is Lys, or a conservative amino acid substitution,
$F_4$ is Ser, or any amino acid, and
$G_4$ is Thr, or any amino acid,
wherein the peptide has a reinforced or stabilized alpha helical secondary structure (e.g., wherein the peptide includes at least one internal crosslink).

In some instances, the peptide has or can be induced to have alpha helical secondary structure. In some instances, $A_3$ is missing.

Peptides can also include at least seven (e.g., 7, 8, 9, 10, 11, 12, 13, 14, 15, 16, 17, 18, 19, 20, 21, 22, 23, 24, 25, 26, 27, 28, 29, 30, 31, 32, 33, 34, or 35) contiguous amino acids of the amino acid sequence $A_0B_0C_0D_0E_0F_0G_0$ $A_1B_1C_1D_1E_1F_1G_1$ $A_2B_2C_2D_2E_2F_2G_2$ $A_3B_3C_3D_3E_3F_3G_3$ $A_4B_4C_4D_4E_4F_4G_4$ (SEQ ID NO:1) wherein:

$A_0$ is Phe,
$B_0$ is Asp,
$C_0$ is Ala, or Ser,
$D_0$ is Ser,
$E_0$ is Ile,
$F_0$ is Ser,
$G_0$ is Gln,
$A_1$ is Val or Ile,
$B_1$ is Asn,
$C_1$ is Glu,
$D_1$ is Lys,
$E_1$ is Ile,
$F_1$ is Asn,
$G_1$ is Gln,
$A_2$ is Ser,
$B_2$ is Leu,
$C_2$ is Ala,
$D_2$ is Phe,
$E_2$ is Ile,
$F_2$ is Arg,
$G_2$ is Lys, or Arg, $A_3$ is Ser,
$B_3$ is Asp or Asn,
$C_3$ is Glu,
$D_3$ is Leu,
$E_3$ is Leu,
$F_3$ is His,
$G_3$ is Asn or His,
$A_4$ is Val or Ile,
$B_4$ is Asn,
$C_4$ is Ala, Val, or Thr,
$D_4$ is Gly,
$E_4$ is Lys,
$F_4$ is Ser,
$G_4$ is Thr, wherein: one or more (e.g., 1, 2, 3, 4, 5, 6, 7, 8, 9, 10, 11, 12, 13, 14, 15, 16, 17, 18) of $A_0$, $D_0$, $E_0$, $A_1$, $D_1$, $E_1$, $A_2$, $B_2$, $D_2$, $E_2$, $A_3$, $B_3$, $D_3$, $E_3$, $A_4$, $B_4$, $D_4$, $E_4$, or $A_0$, $D_0$, $E_0$, $A_1$, $D_1$, $E_1$, $A_2$, $D_2$, $E_2$, $A_3$, $D_3$, $E_3$, $A_4$, $D_4$, $E_4$ are replaced by a conservative amino acid substitution that does not alter the binding face of the peptide; and/or amino acids outside residues corresponding to $A_0$, $D_0$, $E_0$, $A_1$, $D_1$, $E_1$, $A_2$, $B_2$, $D_2$, $E_2$, $A_3$, $B_3$, $D_3$, $E_3$, $A_4$, $B_4$, $D_4$, $E_4$, or $A_0$, $D_0$, $E_0$, $A_1$, $D_1$, $E_1$, $A_2$, $D_2$, $E_2$, $A_3$, $D_3$, $E_3$, $A_4$, $D_4$, $E_4$ are at least 80% (e.g., 80%, 85%, 90%, 95%, 98%, 99%, 99.5%, or 100%) identical to the sequence of SEQ ID NO:1; and/or wherein the peptide has a reinforced or stabilized alpha helical secondary structure (e.g., wherein the peptide includes at least one internal crosslink). In some instances, A3 is missing.

In some instances, SEQ ID NO:1 corresponds to or is FDASISQVNEKINQSLAFIRKSDELLHNVNAGKST (SEQ ID NO:2). In some instances, peptides can have at least 80% (e.g., 80%, 85%, 90%, 95%, 98%, 99%, 99.5%, or 100%) identity to SEQ ID NO: 2 or can include SEQ ID NO:1 or SEQ ID NO:2 with one or more (e.g., 1, 2, 3, 4, 5, 6, 7, 8, 9, 10, 11, 12, 13, 14, 15, 16, 17, 18) conservative amino acid substitutions. In some cases, the stabilized peptide has the sequence of SEQ ID NO:1 with one or two staples (e.g., one staple between two amino acids separated by 6 amino acids or two staples each between two amino acids that are separated by 6 amino acids). In addition, 1, 2, 3, 4 or 5 of the amino acids (whose side chains are not replaced with a staple) can in this stabilized peptide can be replaced by a conservative substitution.

The "interacting face" of the peptides herein includes those amino acid residues of the alpha helix that interact (e.g., interact specifically or bind specifically) with the RSV 5-helix bundle (e.g., amino acid residues in the RSV 5-helix bundle). In some embodiments, the interacting face of SEQ ID NO:1 and/or SEQ ID NO:2 is the hydrophobic interacting face shown in FIG. 2A, and can sometimes include reinforcing interactions with charged residues found at the border between the hydrophobic and hydrophilic alpha-helical faces. Alternatively or in addition, amino acids of the hydrophobic interacting face include the residues highlighted in FIG. 2B (e.g., amino acids corresponding to $A_0$, $D_0$, $E_0$, $A_1$, $D_1$, $E_1$, $A_2$, $B_2$, $D_2$, $E_2$, $A_3$, $B_3$, $D_3$, $E_3$, $A_4$, $B_4$, $D_4$, $E_4$, or $A_0$, $D_0$, $E_0$, $A_1$, $D_1$, $E_1$, $A_2$, $D_2$, $E_2$, $A_3$, $D_3$, $E_3$, $A_4$, $D_4$, $E_4$ of SEQ ID NO:1). In the context of these amino acids (i.e., amino acids in the interacting face of the peptides disclosed herein (e.g., SEQ ID NO:1-SEQ ID NO:26, see, e.g., Table 2), a conservative amino acid substitution is an amino acid substitution that does not alter the chemical makeup of the interacting face of the peptide. Likewise, a conservative amino acid substitution is an amino acid substitution that does not reduce (e.g., substantially reduce) binding of the peptide to the RSV 5-helix bundle and may, in some circumstances, improve binding activity. Methods for detecting any reduction in binding can include comparing binding affinity following conservative amino acid substitution, wherein any amino acid substitution that reduces (e.g., substantially reduces) binding are not conservative amino acid substitutions. In some embodiments, substantially reduced binding can include binding that is 10%, 20%, 30%, 40%, 50%, 60%, 70%, 80%, 90%, 95%, 98%, 99%, or 100% less than binding of the unmodified peptide to the RSV 5-helix bundle. Methods for assessing interaction between a peptide and RSV 5 helix bundle are disclosed herein. Methods for identifying the interactive face of a peptide are known in the art (see, e.g., Broglia et al., Protein sci., 14(10):2668-81, 2005; Hammond et al., J. Pharm. Sci., 98(1):4589-603, 2009; Ng and Yang, J. Phys. Chem. B., 111(50):13886-93, 2007; and Bird et al., PNAS USA, 197: 14093, 2010).

In some instances, a "conservative amino acid substitution" can include substitutions in which one amino acid residue is replaced with another amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Methods for determining percent identity between amino acid sequences are known in the art. For example, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, or 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The determination of percent identity between two amino acid sequences is accomplished using the BLAST 2.0 program. Sequence comparison is performed using an ungapped alignment and using the default parameters (Blossom 62 matrix, gap existence cost of 11, per residue gapped cost of 1, and a lambda ratio of 0.85). The mathematical algorithm used in BLAST programs is described in Altschul et al. (Nucleic Acids Res. 25:3389-3402, 1997).

In some instances, amino acid sequences of any peptide disclosed herein can be varied as long as the residues of the interacting face are identical to those shown for $A_0$, $D_0$, $E_0$, $A_1$, $D_1$, $E_1$, $A_2$, $B_2$, $D_2$, $E_2$, $A_3$, $B_3$, $D_3$, $E_3$, $A_4$, $B_4$, $D_4$, $E_4$, or $A_0$, $D_0$, $E_0$, $A_1$, $D_1$, $E_1$, $A_2$, $D_2$, $E_2$, $A_3$, $D_3$, $E_3$, $A_4$, $D_4$, $E_4$ of SEQ ID NO:1, or are conservative substitutions thereof.

As disclosed above, peptides herein include at least two modified amino acids that together form an internal (intra-molecular) cross-link (or staple), wherein the at least two modified amino acids are separated by 2 (i.e., i, i+3, shown in Table 1 (FIG. 22) as ☐), 3 (i.e., i, i+4, shown in Table 1 (FIG. 22) as ○), or, 6 (i.e., i, i+7, shown in Table 1 (FIG. 22) as ▲) amino acids.

In the case of a cross-link between i and i+3 the cross-link can be a C7 alkylene or alkenylene. In the case of a cross-link between i and i+4 the cross-link can be a C8 alkylene or alkenylene. In the case of a cross-link between i and i+7 the cross-link can be a C11, C12 or C13 alkylene or alkenylene. When the cross-link is an alkenylene there can one or more double bonds.

In the case of a cross-link between i and i+3 the cross-link can be a C6, C7, or C8 alkyl or alkene (e.g., a C6 alkene having a single double bond). In the case of a cross-link between i and i+4 the cross-link can be a C8 alkyl or alkene. In the case of a cross-link between i and i+7 the cross-link can be a C11, C12 or C13 alkyl or alkene (e.g., a C11 alkene having a single double bond). When the cross-link is an alkene there can be one or more double bonds.

"Peptide stapling" is a term coined from a synthetic methodology wherein two olefin-containing side-chains (e.g., cross-linkable side chains) present in a polypeptide chain are covalently joined (e.g., "stapled together") using a ring-closing metathesis (RCM) reaction to form a cross-linked ring (Blackwell et al., J. Org. Chem., 66: 5291-5302, 2001; Angew et al., Chem. Int. Ed. 37:3281, 1994). As used herein, the term "peptide stapling," includes the joining of two (e.g., at least one pair of) double bond-containing side-chains, triple bond-containing side-chains, or double bond-containing and triple bond-containing side chain, which may be present in a polypeptide chain, using any number of reaction conditions and/or catalysts to facilitate such a reaction, to provide a singly "stapled" polypeptide. The term "multiply stapled" polypeptides refers to those polypeptides containing more than one individual staple, and may contain two, three, or more independent staples of various spacings and compositions. Additionally, the term "peptide stitching," as used herein, refers to multiple and tandem "stapling" events in a single polypeptide chain to provide a "stitched" (e.g., tandem or multiply stapled) polypeptide, in which two staples, for example, are linked to a common residue. Peptide stitching is disclosed in WO 2008121767 and in WO 2010/068684, which are both hereby incorporated by reference. In some instances, staples, as used herein, can retain the unsaturated bond or can be reduced (e.g., as mentioned below in the stitching paragraph description).

While many peptide staples have all hydrocarbon cross-links, other type of cross-links or staples can be used. For example, triazole-containing (e.g, 1, 4 triazole or 1, 5 triazole) crosslinks can be used (Kawamoto et al. 2012 Journal of Medicinal Chemistry 55:1137; WO 2010/060112).

Stapling of a peptide using all-hydrocarbon cross-link has been shown to help maintain its native conformation and/or secondary structure, particularly under physiologically relevant conditions (Schafmiester et al., J. Am. Chem. Soc., 122:5891-5892, 2000; Walensky et al., Science, 305:1466-1470, 2004).

Stapling the polypeptide herein by an all-hydrocarbon crosslink predisposed to have an alpha-helical secondary structure can constrain the polypeptide to its native alpha-helical conformation. The constrained secondary structure may, for example, increase the peptide's resistance to proteolytic cleavage, may increase the peptide's thermal stability, may increase the peptide's hydrophobicity, may allow for better penetration of the peptide into the target cell's membrane (e.g., through an energy-dependent transport mechanism such as pinocytosis), and/or may lead to an improvement in the peptide's biological activity relative to the corresponding uncrosslinked (e.g., "unstitched" or "unstapled") peptide. Such constraints have been applied to the apoptosis-inducing BID-BH3 alpha-helix, resulting in a higher suppression of malignant growth of leukemia in an animal model compared to the unstitched polypeptide (Walensky et al., Science, 305:1466-1470, 2004; U.S. 2005/02506890; and U.S. 2006/0008848, each of which is incorporated herein by reference). Such constraints have also been introduced into (1) pro-apoptotic MCL-1 BH3 helix (see, e.g., Stewart et al, Nature Chemical Biology, 2010) resulting in sensitization of apoptosis by selective inhibition of the chemoresistance protein MCL-1, (2) pro-apoptotic BIM BH3 (see, e.g., Walensky et al. Molecular Cell, 2006; Gavathiotis et al, Nature, 2008; Gavathiotis et al, Molecular Cell, 2010) resulting in activating apoptosis through inhibition of anti-apoptotic proteins and direct activation of pro-apoptotic proteins, (3) HIV gp41 domains (see, e.g., Bird et al, PNAS, 2010; WO 2010/148335) resulting in optimized anti-HIV fusion inhibitors with enhanced pharmacologic properties and stabilization of HIV epitopes for vaccine development).

Peptides herein include at least two internally cross-linked or stapled amino acids, wherein the at least two amino acids are separated by 2 (i.e., i, i+3, shown in Table 1 (FIG. 22) as ☐), 3 (i.e., i, i+4, shown in Table 1 as ○), or, 6 (i.e., i, i+7, shown in Table 1 (FIG. 22) as ▲) amino acids. While at least two amino acids are required to support an internal cross-link (e.g., a staple), additional pairs of internally cross-linked amino acids can be included in a peptide, e.g., to support additional internal cross-links (e.g., staples). For example peptides can include 1, 2, 3, 4, 5, or more staples. Examples of peptide staples are illustrated in the figures. Cross-linked peptides (e.g., stapled and/or stitched peptides) are generally referred to herein as SAHF peptides.

Figure 10A:
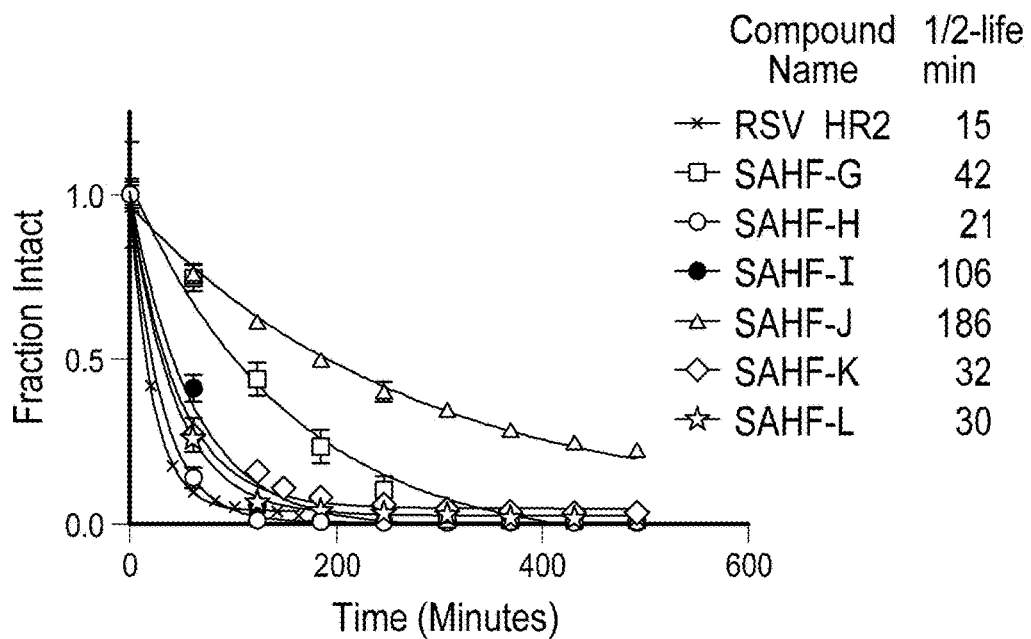
FIGS. 10A-B|Line graphs (A and B) and accompanying peptide half-life tables (Ai and Bi) showing that insertion of single and double staples, respectively, consistently enhances peptide protease (chemotrypsin) resistance compared to the unmodified peptide, with the doubly-stapled derivatives (B) exhibiting the most dramatic proteolytic stability.
Figure 10B:
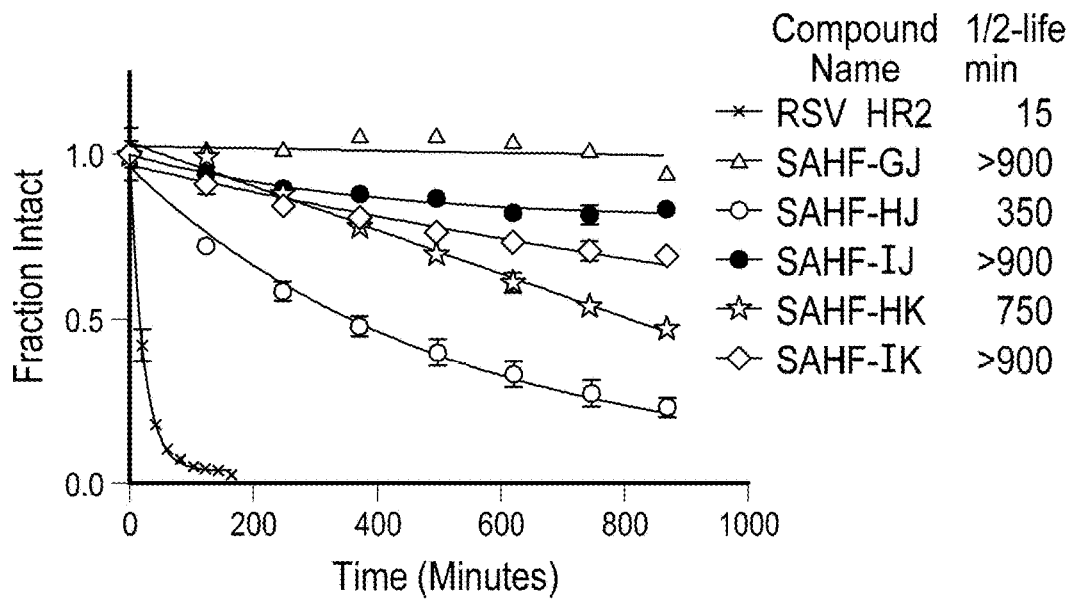

Alternatively or in addition, peptides can include three internally cross-linked or stitched amino acids, e.g., yielding two staples arising from a common origin. A peptide stitch includes at least three internally cross-linked amino acids, wherein the middle of the three amino acids (referred to here as the core or central amino acid and shown in Table 1 (FIG. 22) as "i") forms an internal cross-link (between alpha carbons) with each of the two flanking modified amino acids. The alpha carbon of the core amino acid has side chains that are internal cross-links to the alpha carbons of other amino acids in the peptide, which can be saturated or not saturated. Amino acids cross-linked to the core amino acid can be separated from the core amino acid in either direction by 2, 3, or 6 amino acids (e.g., i, i−3, i, i−4, i, i−7 (shown in Table 1 (FIG. 22) as ■, ●, and ▼, respectively), i, i+3, i, i+4, i, i+7 (shown in Table 1 (FIG. 22) as ☐, ○, and ▲, respectively), where "i" is the core amino acid). The number of amino acids on either side of the core (e.g., between the core amino acid and an amino acid cross-linked to the core) can be the same or different. Examples of such three amino acid containing peptide stitches are illustrated in FIG. 10. In some instances, a stitch can include 3, 4, 5, or more internally cross-linked amino acids. In some instances, peptides can include 1, 2, 3, 4, 5, or more stitches.

In some embodiments, peptides herein can include a combination of at least one (e.g., 1, 2, 3, 4, or 5) staple and at least one (e.g., 1, 2, 3, 4, or 5) stitch.

Cross-linked peptides (e.g., stapled and/or stitched peptides) are generally referred to herein as SAHF peptides.

Peptides can include cross-linked amino acids at one or more of the positions illustrated in Table 1.

Figures 12A, 12B:
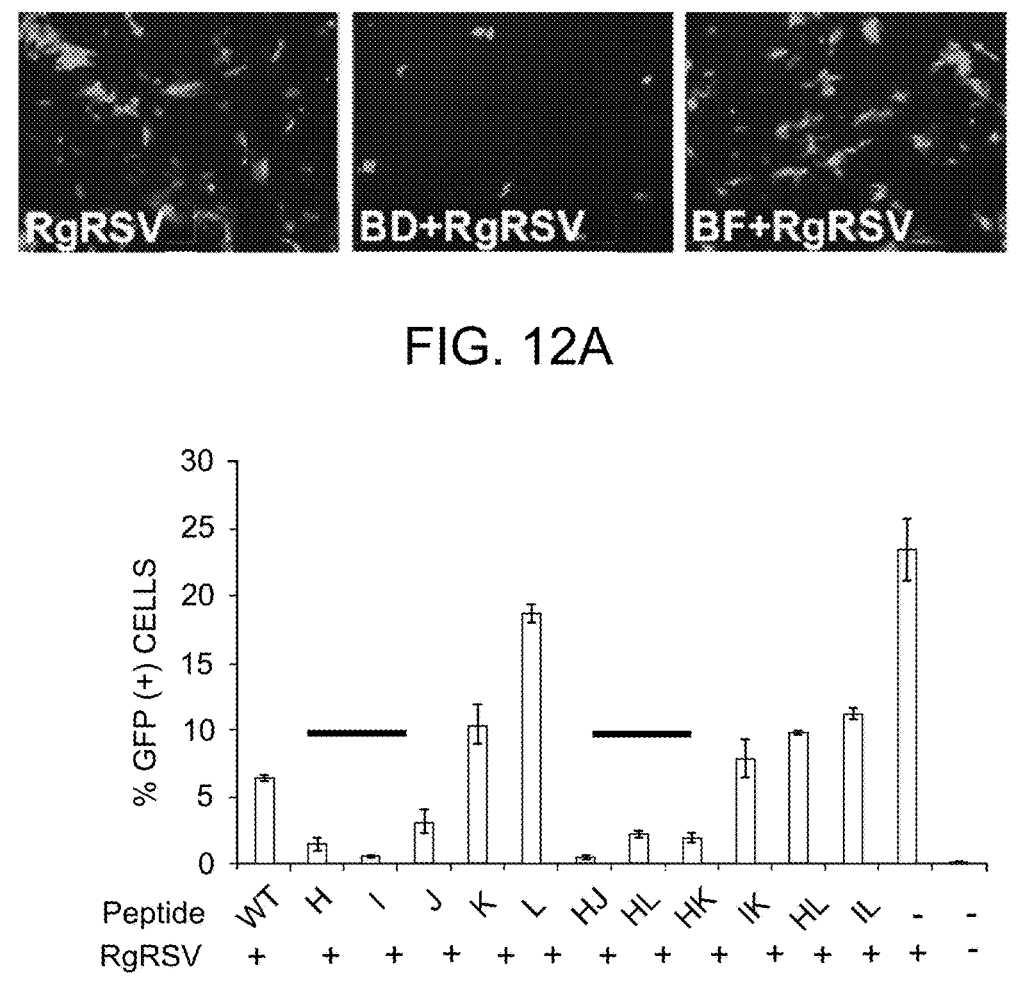
Figure 22:
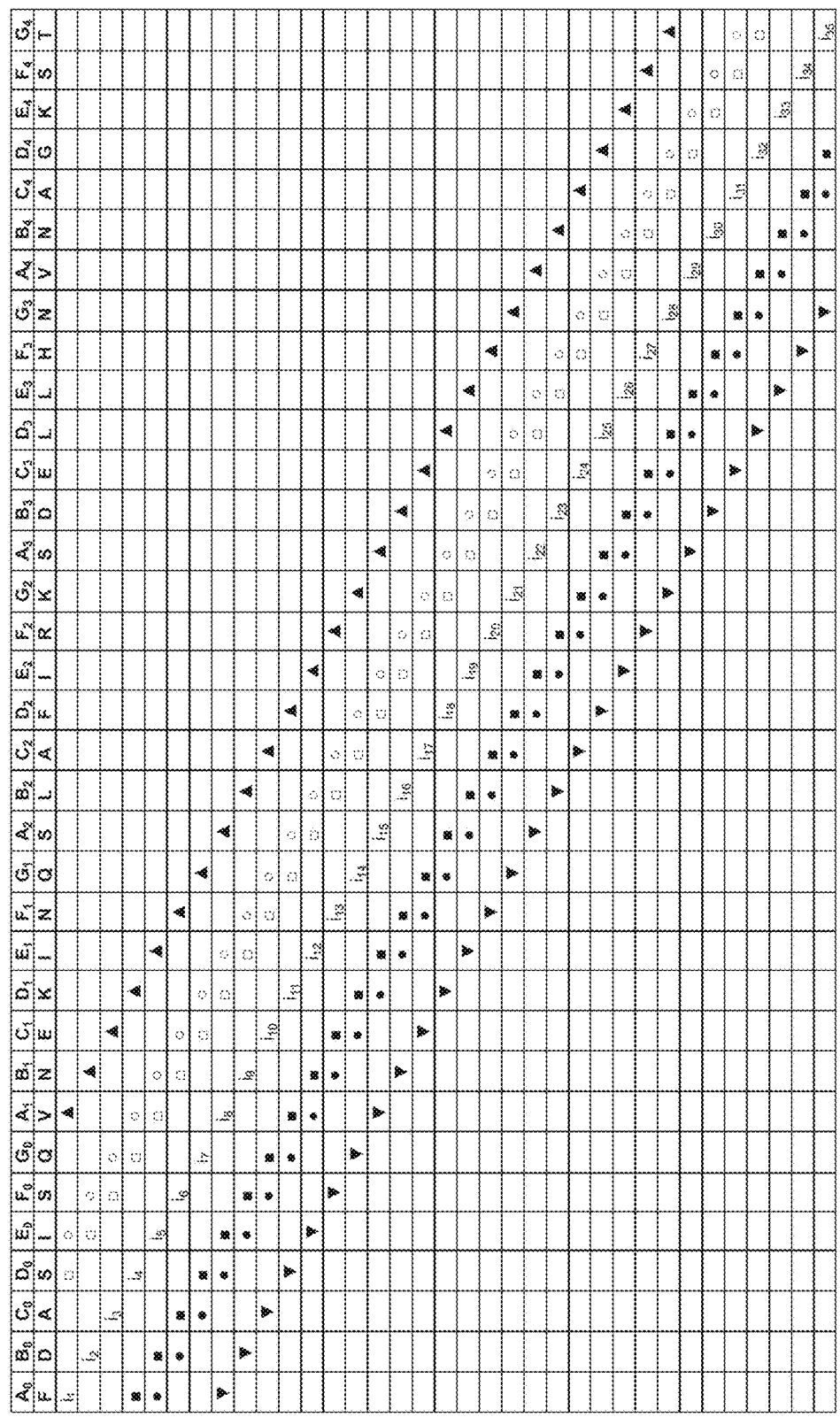
FIG. 22|A table depicting various stapled peptides (Table 1).

In FIG. 22 (Table 1) positions of cross-links are indicated by symbols and the letter "i". For example, $i_{10}$ (C1) can be linked via a i+3 staple to $F_1$ or $G_0$ (also called i–3) or a i+4 staple to G1 or $F_0$ (also called i–4) or a i+7 staple to $C_2$ or $C_0$ (also called i–7). Of course, $i_{10}$ (C1) could be stitched to, for example $F_1$ (i+3) and C0 (i–7). In Table 1 (FIG. 12), the first row shows SEQ ID NO:1 and the second row shows an exemplary embodiment of SEQ ID NO: 1, SEQ ID NO:2.

Internal cross-links (e.g., staples and/or stitches) can be positioned on amino acids within a peptide to conserve the structural relationship of amino acids in the binding or interacting face of the peptide (e.g., to preserve the binding interface of a peptide). Alternatively, staples can placed on the interacting face as long as binding affinity or activity is not altered. In some embodiments, the staple or staples can be placed such that they partially or completely engage the target and enhance binding activity, as exemplified for the stapled MCL-1 BH3 helix (Stewart et al, Nature Chemical Biology, 2010). For example, one or more of $i_1$-$i_{35}$ can be stapled or stitched to at least one other amino acids to conserve the structural relationship of amino acids in the hydrophobic interaction face shown in FIG. 2A (amino acids in the interacting face are highlighted in FIG. 2B). Such internal cross-links can include: one or more staples; one or more stitches; and/or a combination of one or more staples with one or more stitches. In some instances, two or more amino acids located between amino acids $B_0$ and $D_1$ and/or $F_2$ and $D_4$ can be cross-linked (e.g., stapled or stitched). Exemplary cross-linked peptides include SEQ ID NOs: 3-18. In some instances, cross-linked peptides can include SEQ ID NO: 10, SEQ ID NO: 11, SEQ ID NO: 12, SEQ ID NO: 13, SEQ ID NO: 14, or SEQ ID NO: 17.

In some instances, SEQ ID NO:1 does not include (e.g., does not include only): an internal cross-link between amino acid $B_0$ and amino acid $F_0$; an internal cross-link between amino acid $C_0$ and amino acid $G_0$; an internal cross-link between amino acid $D_0$ and amino acid $A_1$; an internal cross-link between amino acid $B_3$ and amino acid $F_3$; an internal cross-link between amino acid $C_3$ and amino acid $G_3$; an internal cross-link between amino acid $D_3$ and amino acid $A_4$. In some instances, peptides herein do not include an internal cross-link that disrupts the binding interface of SEQ ID NO:2. For examples, in some instances, peptides do not include an internal cross-link between two or more (e.g., 2, 3, 4, 5, 6, 7, 8, 9, 10, or more) amino acids on the interacting face of SEQ ID NO:2 (see, e.g., FIG. 2).

In some instances, peptides can include two or more of: an internal cross-link between amino acid $B_0$ and amino acid $F_0$; an internal cross-link between amino acid $C_0$ and amino acid $G_0$; an internal cross-link between amino acid $D_0$ and amino acid $A_1$; an internal cross-link between amino acid $B_3$ and amino acid $F_3$; an internal cross-link between amino acid $C_3$ and amino acid $G_3$; and an internal cross-link between amino acid $D_3$ and amino acid $A_4$; and/or peptides that include an internal cross-link between amino acid $B_0$ and amino acid $F_0$; an internal cross-link between amino acid $C_0$ and amino acid $G_0$; an internal cross-link between amino acid $D_0$ and amino acid $A_1$; an internal cross-link between amino acid $B_3$ and amino acid $F_3$; an internal cross-link between amino acid $C_3$ and amino acid $G_3$; and/or an internal cross-link between amino acid $D_3$ and amino acid $A_4$ and at least one additional cross-link (wherein the positions recited refer to positions in SEQ ID NO:1)

Selection of amino acids for modification (e.g., to support an internal cross-link) can also be facilitated by staple scanning. The term "staple scan" refers to the synthesis of a library of stapled peptides whereby the location of the i and i+3; i and i+4; and i and i+7 single and multiple staple, or stitches, are positioned sequentially down the length of the peptide sequence, sampling all possible positions, to identify desired or optimal properties and activities for the stapled or stitched constructs. Examples of staple scanning methods are illustrated in the figures.

In some embodiments, the tethers, e.g., hydrocarbon staples are used to stabilize structures other than helices. In such cases, the ends of the tethers can be placed at intervals other than at i, i+3, i+4, and i+7.

Structurally constrained peptides and the like are understood to include modified peptides having any (i.e., at least one) chemical modification, e.g., mutation of the original or native sequence with a natural or non-natural amino acid; chemical modification to incorporate a molecular tether; chemical modification to promote the formation of a disulfide bridge; etc. such that the structurally constrained peptide adopts a more limited number of structures than the unmodified peptide. A structurally constrained peptide can include 1, 2, 3, 4, 5, 6, 7, 8, 9, 10, 11, 12, or more mutations as compared to the native, wild-type sequence. For example, molecular tethers can include hydrocarbon staples to promote the formation of stable helical structures, especially alpha-helical and $3_{10}$ structures, or kinks depending on the positions of the ends of the tethers and the lengths of the tethers. Natural or non-natural amino acids can be employed to promote kinks (e.g. bends in the structure as defined by the variable angles between the two adjoining structures) or other preferred confirmations. For example, the natural amino acid proline can induce a kink in a peptide due to the structure of the amino acid R group and the lack of a hydrogen-bond donor. Non-natural amino acids, particularly those having large and/or charged R groups, or N-methylated amides, N-substituted glycines, cyclic alpha, alpha-disubstitution, cyclic N,N-disubstitution, and beta-amino acids can promote specific, desired confirmations. It is understood that a population of "structurally constrained" peptides in solution may not all have the desired confirmation all of the time. Instead, in a population of structurally constrained peptides in solution, the desired confirmation is present at least about 30%, 40%, 50%, 60%, 70%, 80%, 90%, 100%, or more of the time than the native or original peptide sequence in solution prior to chemical modification. The structure of a population of peptides in solution can be determined by various methods known to those of skill in the art including, but not limited to, circular dichroism and NMR spectroscopy. X-ray crystallography can be applied to determine the structure of a constrained peptide when packed in the form of a crystal.

Suitable tethers are described herein and in U.S. Patent Publication No. 2005/0250680, PCT/US2008/058575, U.S. Ser. No. 12/864,375 (WO 2009/108261), and WO 2010/148335.

Amino acid side chains suitable for use in the peptides disclosed herein are known in the art. For example, suitable amino acid side chains include methyl (as the alpha-amino acid side chain for alanine is methyl), 4-hydroxyphenylmethyl (as the alpha-amino acid side chain for tyrosine is 4-hydroxyphenylmethyl) and thiomethyl (as the alpha-amino acid side chain for cysteine is thiomethyl), etc. A "terminally unsaturated amino acid side chain" refers to an amino acid side chain bearing a terminal unsaturated moiety, such as a substituted or unsubstituted, double bond (e.g., olefinic) or a triple bond (e.g., acetylenic), that participates in crosslinking reaction with other terminal unsaturated moieties in the polypeptide chain. In certain embodiments, a "terminally unsaturated amino acid side chain" is a terminal olefinic amino acid side chain. In certain embodiments, a "terminally unsaturated amino acid side chain" is a terminal acetylenic amino acid side chain. In certain embodiments, the terminal moiety of a "terminally unsaturated amino acid side chain" is not further substituted.

As noted above an internal tether or cross-link can extend across the length of one helical turn (i.e., about 3.4 amino acids (i.e., i, i+3, or i, i+4) or two helical turns (i.e., about 7 amino acids (i.e., i, i+7). Accordingly, amino acids positioned at i and i+3; i and i+4; or i and i+7 are ideal candidates for chemical modification and cross-linking (see Table 1). Thus, for example, where a peptide has the sequence . . . $Xaa_1$, $Xaa_2$, $Xaa_3$, $Xaa_4$, $Xaa_5$, $Xaa_6$, $Xaa_7$, $Xaa_8$, $Xaa_9$ . . . (wherein, " . . . " indicates the optional presence of additional amino acids), cross-links between $Xaa_1$ and $Xaa_4$, or between $Xaa_1$ and $Xaa_5$, or between $Xaa_1$ and $Xaa_8$ are useful as are cross-links between $Xaa_2$ and $Xaa_5$, or between $Xaa_2$ and $Xaa_6$, or between $Xaa_2$ and $Xaa_9$, etc.

Polypeptides can include more than one crosslink within the polypeptide sequence to either further stabilize the sequence or facilitate the stabilization of longer polypeptide stretches. If the polypeptides are too long to be readily synthesized in one part, independently synthesized, cross-linked peptides can be conjoined by a technique called native chemical ligation (Bang, et al., J. Am. Chem. Soc. 126:1377). Alternately, large peptides are routinely synthesized using a convergent approach whereby fully protected fragments are specifically and sequentially reacted to form the full length desired product, after final deprotection, such as in the industrial synthesis of Fuzeon.

The invention features a modified polypeptide of Formula (I),

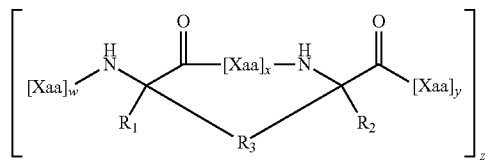

Formula (I)

or a pharmaceutically acceptable salt thereof, wherein;

each $R_1$ and $R_2$ are independently H or a $C_1$ to $C_{10}$ alkyl, alkenyl, alkynyl, arylalkyl, cycloalkylalkyl, heteroarylalkyl, or heterocyclylalkyl;

$R_3$ is alkylene, alkenylene or alkynylene (e.g., a $C_6$, $C_7$, $C_8$, $C_{11}$, $C_{12}$ or $C_{13}$ alkylene), or $[R_4'-K-R_4]_n$; each of which is substituted with 0-6 $R_5$;

$R_4$ and $R_4'$ are independently alkylene, alkenylene or alkynylene (e.g., each are independently a $C_1$, $C_2$, $C_3$, $C_4$, $C_5$, $C_6$, $C_7$, $C_8$, $C_9$ or $C_{10}$ alkylene, alkenylene or alkynylene);

$R_5$ is halo, alkyl, $OR_6$, $N(R_6)_2$, $SR_6$, $SOR_6$, $SO_2R_6$, $CO_2R_6$, $R_6$, a fluorescent moiety, or a radioisotope;

K is O, S, SO, $SO_2$, CO, $CO_2$, $CONR_6$, or

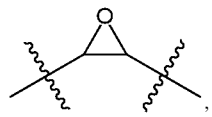 [SMILES: *C1CC1*]

aziridine, episulfide, diol, amino alcohol;

$R_6$ is H, alkyl, or a therapeutic agent;

n is 2, 3, 4 or 6;

x is an integer from 2-10;

w and y are independently an integer from 0-100;

z is an integer from 1-10 (e.g., 1, 2, 3, 4, 5, 6, 7, 8, 9, 10); and each Xaa is independently an amino acid (e.g., one of the 20 naturally occurring amino acids or any naturally occurring non-naturally occurring amino acid);

wherein the polypeptide comprises at least 8 contiguous amino acids of SEQ ID NO:1 or 2 or a variant thereof, or another polypeptide sequence described herein except that: (a) within the 8 contiguous (e.g., 9, 10, 11, 12, 13, 14, 15, 16, 17, 18, 19, 20, 21, 22, 23, 24, 24, 25, 26, 27, 28, 29, 30, 31, 32, 33, 34 or 35) amino acids of SEQ ID NO:1 or 2 the side chains of at least onepair (e.g., one or two pairs) of amino acids separated by 2, 3 or 6 amino acids is replaced by the linking group, $R_3$, which connects the alpha carbons of the pair of amino acids as depicted in Formula I; and (b) the alpha carbon of the first of the pair of amino acids is substituted with $R_1$ as depicted in formula I and the alpha carbon of the second of the pair of amino acids is substituted with $R_2$ as depicted in Formula I.

In another aspect, the invention features a modified polypeptide of Formula (II),

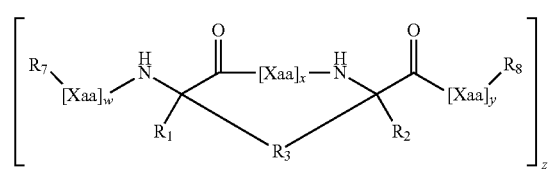

Formula (II)

or a pharmaceutically acceptable salt thereof, wherein;

each $R_1$ and $R_2$ are independently H or a $C_1$ to $C_{10}$ alkyl, alkenyl, alkynyl, arylalkyl, cycloalkylalkyl, heteroarylalkyl, or heterocyclylalkyl;

$R_3$ is alkylene, alkenylene or alkynylene (e.g., a $C_6$, $C_7$, $C_8$, $C_{11}$, $C_{12}$ or $C_{13}$ alkylene) or $[R_4'-K-R_4]_n$; each of which is substituted with 0-6 $R_5$;

$R_4$ and $R_4'$ are independently alkylene, alkenylene or alkynylene (e.g., each are independently a $C_1$, $C_2$, $C_3$, $C_4$, $C_5$, $C_6$, $C_7$, $C_8$, $C_9$ or $C_{10}$ alkylene, alkenylene or alkynylene);

$R_5$ is halo, alkyl, $OR_6$, $NHR_6$, $N(R_6)_2$, $SR_6$, $SOR_E$, $SO_2R_6$, $CO_2R_6$, $R_6$, a fluorescent moiety, or a radioisotope;

K is O, S, SO, $SO_2$, CO, $CO_2$, $CONR_6$, or

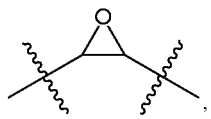

aziridine, episulfide, diol, amino alcohol, diamine;

$R_6$ is H, alkyl, or a therapeutic agent;

n is 2, 3, 4, 5, or 6;

x is an integer from 2-10;

w and y are independently an integer from 0-100;

z is an integer from 1-10 (e.g., 1, 2, 3, 4, 5, 6, 7, 8, 9, 10); and each Xaa is independently an amino acid (e.g., one of the 20 naturally occurring amino acids or any naturally occurring non-naturally occurring amino acid);

$R_7$ is PEG, a tat protein, an affinity label, a targeting moiety, a fatty acid-derived acyl group, a biotin moiety, a fluorescent probe (e.g. fluorescein or rhodamine) linked via, e.g., a thiocarbamate or carbamate linkage;

$R_8$ is H, OH, $NH_2$, $NHR_{8a}$, $NR_{8a}R_{8b}$;

wherein the polypeptide comprises at least 8 contiguous amino acids (e.g., 9, 10, 11, 12, 13, 14, 15, 16, 17, 18, 19, 20, 21, 22, 23, 24, 24, 25, 26, 27, 28, 29, 30, 31, 32, 33, 34 or 35) of SEQ ID NO:1 or 2, or another polypeptide sequence described herein except that: (a) within the 8 contiguous amino acids of SEQ ID NO:1 or 2 the side chains of at least one pair of amino acids separated by 2, 4 or 6 amino acids is replaced by the linking group, $R_3$, which connects the alpha carbons of the pair of amino acids as depicted in formula I; and (b) the alpha carbon of the first of the pair of amino acids is substituted with $R_1$ as depicted in Formula II and the alpha carbon of the second of the pair of amino acids is substituted with $R_2$ as depicted in Formula II.

In the case of Formula I or Formula II, the following embodiments are among those disclosed.

In cases where x=2 (i.e., i+3 linkage), R3 can be a C7 alkylene, alkenylene. Where it is an alkenylene there can one or more double bonds. In cases where x=6 (i.e., i+4 linkage), $R_3$ can be a C11, C12 or C13 alkylene or alkenylene. Where it is an alkenylene there can one or more double bonds. In cases where x=3 (i.e., i+4 linkage), $R_3$ can be a C8 alkylene, alkenylene. Where it is an alkenylene there can one or more double bonds.

In certain instances, the two alpha, alpha disubstituted stereocenters (alpha carbons) are both in the R configuration or S configuration (e.g., i, i+4 cross-link), or one stereocenter is R and the other is S (e.g., i, i+7 cross-link). Thus, where Formula I is depicted as

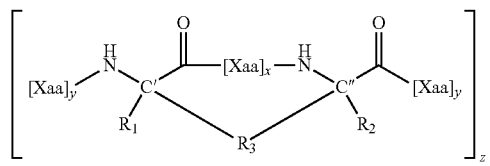

the C' and C" disubstituted stereocenters can both be in the R configuration or they can both be in the S configuration, for example when x is 3. When x is 6, the C' disubstituted stereocenter is in the R configuration and the C" disubstituted stereocenter is in the S configuration or the C' disubstituted stereocenter is in the S configuration and the C" disubstituted stereocenter is in the R configuration. The $R_3$ double bond may be in the E or Z stereochemical configuration. Similar configurations are possible for the carbons in Formula II corresponding to C' and C" in the formula depicted immediately above.

In some instances $R_3$ is $[R_4-K-R_4']_n$; and $R_4$ and $R_4'$ are independently alkylene, alkenylene or alkynylene (e.g., each are independently a C1, C2, C3, C4, C5, C6, C7, C8, C9 or $C_{10}$ alkylene, alkenylene or alkynylene In some instances, the polypeptide includes an amino acid sequence which, in addition to the amino acids side chains that are replaced by a cross-link, have 1, 2, 3, 4 or 5, 6, 7, 8, 9, 10, 11, 12 amino acid changes (e.g., conservative amino acid changes) in any of SEQ ID NOs:1 or 2.

The tether can include an alkyl, alkenyl, or alkynyl moiety (e.g., $C_6$, $C_8$ or $C_{11}$ alkyl or a $C_6$, $C_8$ or $C_{11}$ alkenyl, or $C_5$, $C_8$ or $C_{11}$ alkynyl). The tethered amino acid can be alpha disubstituted (e.g., $C_1$-$C_3$ or methyl). $[Xaa]_y$ and $[Xaa]_w$ are peptides that can independently comprise at least 1, 2, 3, 4, 5, 6, 7, 8, 9, 10, 11, 12, 13, 14, 15, 16, 17, 18, 19, 20, 25, 26, 27, 28, 29, 30, 31, 32, 33, 34, or 35 contiguous amino acids of SEQ ID NOs: 1 or 2 and $[Xaa]_x$ is a peptide that can comprise 2, 3 or 6 contiguous amino acids of acids of SEQ ID NO: 1 or 2.

Peptides can contain one or more asymmetric centers and thus occur as racemates and racemic mixtures, single enantiomers, individual diastereomers and diastereomeric mixtures and geometric isomers (e.g. Z or cis and E or trans) of any olefins present. For example, peptides disclosed herein can exist in particular geometric or stereoisomeric forms, including, for example, cis- and trans-isomers, R- and S-enantiomers, diastereomers, (D)-isomers, (L)-isomers, the racemic mixtures thereof, and other mixtures thereof. Enantiomers can be free (e.g., substantially free) of their corresponding enantiomer, and/or may also be optically enriched. "Optically enriched," as used herein, means that the compound is made up of a significantly greater proportion of one enantiomer. In certain embodiments substantially free means that a composition contains at least about 90% by weight of a preferred enantiomer. In other embodiments the compound is made up of at least about 95%, 98%, or 99% by weight of a preferred enantiomer. Preferred enantiomers may be isolated from racemic mixtures using techniques known in the art, including, but not limited to, for example, chiral high pressure liquid chromatography (HPLC) and the formation and crystallization of chiral salts or prepared by asymmetric syntheses (see, e.g., Jacques, et al, Enantiomers, Racemates and Resolutions (Wiley Interscience, New York, 1981); Wilen, S. H., et al., Tetrahedron 33:2725 (1977); Eliel, EX. Stereochemistry of Carbon Compounds (McGraw-Hill, N.Y., 1962); Wilen, S. H. Tables of Resolving Agents and Optical Resolutions p. 268 (EX. Eliel, Ed., Univ. of Notre Dame Press, Notre Dame, Ind. 1972). All such isomeric forms of these compounds are expressly included in the present invention.

Peptides can also be represented in multiple tautomeric forms, in such instances, the invention expressly includes all tautomeric forms of the compounds described herein (e.g., isomers in equilibrium (e.g., keto-enol), wherein alkylation at multiple sites can yield regioisomers), regioisomers, and oxidation products of the compounds disclosed herein (the invention expressly includes all such reaction products). All such isomeric forms of such compounds are included as are all crystal forms.

The symbol " ⫽ " when used as part of a molecular structure refers to a single bond or a trans or cis double bond.

The term "halo" refers to any radical of fluorine, chlorine, bromine or iodine. The term "alkyl" refers to a hydrocarbon chain that may be a straight chain or branched chain, containing the indicated number of carbon atoms. For example, $C_1$-$C_{10}$ indicates that the group may have from 1 to 10 (inclusive) carbon atoms in it. In the absence of any numerical designation, "alkyl" is a chain (straight or branched) having 1 to 20 (inclusive) carbon atoms in it. The term "alkylene" refers to a divalent alkyl (i.e., —R—).

The term "alkenyl" refers to a hydrocarbon chain that may be a straight chain or branched chain having one or more carbon-carbon double bonds in either Z or E geometric configurations. The alkenyl moiety contains the indicated number of carbon atoms. For example, $C_2$-$C_{10}$ indicates that the group may have from 2 to 10 (inclusive) carbon atoms in it. The term "lower alkenyl" refers to a $C_2$-$C_8$ alkenyl chain. In the absence of any numerical designation, "alkenyl" is a chain (straight or branched) having 2 to 20 (inclusive) carbon atoms in it.

The term "alkynyl" refers to a hydrocarbon chain that may be a straight chain or branched chain having one or more carbon-carbon triple bonds. The alkynyl moiety contains the indicated number of carbon atoms. For example, $C_2$-$C_{10}$ indicates that the group may have from 2 to 10 (inclusive) carbon atoms in it. The term "lower alkynyl" refers to a $C_2$-$C_8$ alkynyl chain. In the absence of any numerical designation, "alkynyl" is a chain (straight or branched) having 2 to 20 (inclusive) carbon atoms in it.

The term "aryl" refers to a 6-carbon monocyclic or 10-carbon bicyclic aromatic ring system wherein 0, 1, 2, 3, 4, or 5 atoms of each ring may be substituted by a substituent. Examples of aryl groups include phenyl, naphthyl and the like. The term "arylalkyl" or the term "aralkyl" refers to alkyl substituted with an aryl. The term "arylalkoxy" refers to an alkoxy substituted with aryl.

The term "cycloalkyl" as employed herein includes saturated and partially unsaturated cyclic hydrocarbon groups having 3 to 12 carbons, preferably 3 to 8 carbons, and more preferably 3 to 6 carbons, wherein the cycloalkyl group additionally may be optionally substituted. Preferred cycloalkyl groups include, without limitation, cyclopropyl, cyclobutyl, cyclopentyl, cyclopentenyl, cyclohexyl, cyclohexenyl, cyclohexadienyl, cycloheptyl, cycloheptadienyl, cycloheptatrienyl, cyclooctyl, cyclooctenyl, cyclooctadienyl, cyclooctatrienyl, and cyclooctynyl.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring may be substituted by a substituent. Examples of heteroaryl groups include pyrrolyl, pyridyl, furyl or furanyl, imidazolyl, 1,2,3-triazolyl, 1,2,4-triazolyl, benzimidazolyl, pyridazyl, pyrimidyl, thiophenyl, quinolinyl, indolyl, thiazolyl, oxazolyl, isoxazolyl and the like. The term "heteroarylalkyl" or the term "heteroaralkyl" refers to an alkyl substituted with a heteroaryl. The term "heteroarylalkoxy" refers to an alkoxy substituted with heteroaryl.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Examples of heterocyclyl groups include piperazinyl, pyrrolidinyl, dioxanyl, aziridinyl, oxiryl, thiiryl, morpholinyl, tetrahydrofuranyl, and the like.

The term "substituents" refers to a group "substituted" on an alkyl, cycloalkyl, aryl, heterocyclyl, or heteroaryl group at any atom of that group. Suitable substituents include, without limitation, halo, hydroxy, mercapto, oxo, nitro, haloalkyl, alkyl, alkaryl, aryl, aralkyl, alkoxy, thioalkoxy, aryloxy, amino, alkoxycarbonyl, amido, carboxy, alkanesulfonyl, alkylcarbonyl, azido, and cyano groups.

In some instances, the hydrocarbon tethers (i.e., cross links) described herein can be further manipulated. In one instance, a double bond of a hydrocarbon alkenyl tether, (e.g., as synthesized using a ruthenium-catalyzed ring closing metathesis (RCM)) can be oxidized (e.g., via epoxidation or dihydroxylation) to provide one of compounds below.

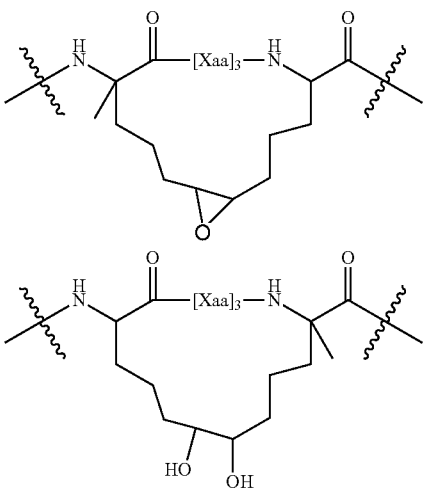

Either the epoxide moiety or one of the free hydroxyl moieties can be further functionalized. For example, the epoxide can be treated with a nucleophile, which provides additional functionality that can be used, for example, to attach a tag (e.g., a radioisotope or fluorescent tag). The tag can be used to help direct the compound to a desired location in the body or track the location of the compound in the body. Alternatively, an additional therapeutic agent can be chemically attached to the functionalized tether (e.g., an anti-cancer agent such as rapamycin, vinblastine, taxol, etc.). Such derivatization can alternatively be achieved by synthetic manipulation of the amino or carboxy-terminus of the polypeptide or via the amino acid side chain. Other agents can be attached to the functionalized tether, e.g., an agent that facilitates entry of the polypeptide into cells.

While hydrocarbon tethers have been described, other tethers are also envisioned. For example, the tether can include one or more of an ether, thioether, ester, amine, or amide moiety. In some cases, a naturally occurring amino acid side chain can be incorporated into the tether. For example, a tether can be coupled with a functional group such as the hydroxyl in serine, the thiol in cysteine, the primary amine in lysine, the acid in aspartate or glutamate, or the amide in asparagine or glutamine. Accordingly, it is possible to create a tether using naturally occurring amino acids rather than using a tether that is made by coupling two non-naturally occurring amino acids. It is also possible to use a single non-naturally occurring amino acid together with a naturally occurring amino acid.

It is further envisioned that the length of the tether can be varied. For instance, a shorter length of tether can be used where it is desirable to provide a relatively high degree of constraint on the secondary alpha-helical structure, whereas, in some instances, it is desirable to provide less constraint on the secondary alpha-helical structure, and thus a longer tether may be desired.

Additionally, while examples of tethers spanning from amino acids i to i+3, i to i+4; and i to i+7 have been described in order to provide a tether that is primarily on a single face of the alpha helix, the tethers can be synthesized to span any combinations of numbers of amino acids.

In some instances, alpha disubstituted amino acids are used in the polypeptide to improve the stability of the alpha helical secondary structure. However, alpha disubstituted amino acids are not required, and instances using mono-alpha substituents (e.g., in the tethered amino acids) are also envisioned.

In some instances it can be useful to create an inactive stapled peptide by replacing one or more (e.g., all three) of $Ser_{22}$ and/or $Val_{29}$ of SEQ ID NO:2 (e.g., $A_3$ and/or $A_4$ of SEQ ID NO:1) with another amino acid, e.g., Ala. In some instances, it can be useful to replace an amino acid on the interacting face of SEQ ID NO:2 (see, e.g., FIG. 2) with another amino acid, e.g., Ala. Such inactive stapled peptides can be useful, for example, as negative controls.

The stapled polypeptides can include a drug, a toxin, a derivative of polyethylene glycol; a second polypeptide; a carbohydrate, etc. Where a polymer or other agent is linked to the stapled polypeptide is can be desirable for the composition to be substantially homogeneous.

The addition of polyethelene glycol (PEG) molecules can improve the pharmacokinetic and pharmacodynamic properties of the polypeptide. For example, PEGylation can reduce renal clearance and can result in a more stable plasma concentration. PEG is a water soluble polymer and can be represented as linked to the polypeptide as formula:

$XO-(CH_2CH_2O)_n-CH_2CH_2-Y$ where n is 2 to 10,000 and X is H or a terminal modification, e.g., a $C_{1-4}$ alkyl; and Y is an amide, carbamate or urea linkage to an amine group (including but not limited to, the epsilon amine of lysine or the N-terminus) of the polypeptide. Y may also be a maleimide linkage to a thiol group (including but not limited to, the thiol group of cysteine). Other methods for linking PEG to a polypeptide, directly or indirectly, are known to those of ordinary skill in the art. The PEG can be linear or branched. Various forms of PEG including various functionalized derivatives are commercially available.

PEG having degradable linkages in the backbone can be used. For example, PEG can be prepared with ester linkages that are subject to hydrolysis. Conjugates having degradable PEG linkages are described in WO 99/34833; WO 99/14259, and U.S. Pat. No. 6,348,558.

In certain embodiments, macromolecular polymer (e.g., PEG) is attached to an agent described herein through an intermediate linker. In certain embodiments, the linker is made up of from 1 to 20 amino acids linked by peptide bonds, wherein the amino acids are selected from the 20 naturally occurring amino acids. Some of these amino acids may be glycosylated, as is well understood by those in the art. In other embodiments, the 1 to 20 amino acids are selected from glycine, alanine, proline, asparagine, glutamine, and lysine. In other embodiments, a linker is made up of a majority of amino acids that are sterically unhindered, such as glycine and alanine Non-peptide linkers are also possible. For example, alkyl linkers such as $-NH(CH_2)_nC(O)-$, wherein n=2-20 can be used. These alkyl linkers may further be substituted by any non-sterically hindering group such as lower alkyl (e.g., $C_1$-$C_6$) lower acyl, halogen (e.g., Cl, Br), CN, $NH_2$, phenyl, etc. U.S. Pat. No. 5,446,090 describes a bifunctional PEG linker and its use in forming conjugates having a peptide at each of the PEG linker termini.

The stapled peptides can also be modified, e.g., to further facilitate cellular uptake or increase in vivo stability, in some embodiments. For example, acylating or PEGylating a peptidomimetic macrocycle facilitates cellular uptake, increases bioavailability, increases blood circulation, alters pharmacokinetics, decreases immunogenicity and/or decreases the needed frequency of administration.

In some embodiments, the stapled peptides disclosed herein have an enhanced ability to penetrate cell membranes (e.g., relative to non-stapled peptides).

Methods of synthesizing the compounds of the described herein are known in the art. Nevertheless, the following exemplary method may be used. It will be appreciated that the various steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and P. G. M. Wuts, Protective Groups in Organic Synthesis, 3d. Ed., John Wiley and Sons (1999); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

The peptides of this invention can be made by chemical synthesis methods, which are well known to the ordinarily skilled artisan. See, for example, Fields et al., Chapter 3 in Synthetic Peptides: A User's Guide, ed. Grant, W.H. Freeman & Co., New York, N.Y., 1992, p. 77. Hence, peptides can be synthesized using the automated Merrifield techniques of solid phase synthesis with the $\alpha$-$NH_2$ protected by either t-Boc or Fmoc chemistry using side chain protected amino acids on, for example, an Applied Biosystems Peptide Synthesizer Model 430A or 431.

One manner of making of the peptides described herein is using solid phase peptide synthesis (SPPS). The C-terminal amino acid is attached to a cross-linked polystyrene resin via an acid labile bond with a linker molecule. This resin is insoluble in the solvents used for synthesis, making it relatively simple and fast to wash away excess reagents and by-products. The N-terminus is protected with the Fmoc group, which is stable in acid, but removable by base. Any side chain functional groups are protected with base stable, acid labile groups.

Longer peptides could be made by conjoining individual synthetic peptides using native chemical ligation. Alternatively, the longer synthetic peptides can be synthesized by well-known recombinant DNA techniques. Such techniques are provided in well-known standard manuals with detailed protocols. To construct a gene encoding a peptide of this invention, the amino acid sequence is reverse translated to obtain a nucleic acid sequence encoding the amino acid sequence, preferably with codons that are optimum for the organism in which the gene is to be expressed. Next, a synthetic gene is made, typically by synthesizing oligonucleotides which encode the peptide and any regulatory elements, if necessary. The synthetic gene is inserted in a suitable cloning vector and transfected into a host cell. The peptide is then expressed under suitable conditions appropriate for the selected expression system and host. The peptide is purified and characterized by standard methods.

The peptides can be made in a high-throughput, combinatorial fashion, e.g., using a high-throughput multiple channel combinatorial synthesizer available from Advanced Chemtech.

Peptide bonds can be replaced, e.g., to increase physiological stability of the peptide, by: a retro-inverso bonds (C(O)—NH); a reduced amide bond (NH—$CH_2$); a thiomethylene bond (S—CH$_2$ or CH$_2$—S); an oxomethylene bond (O—CH$_2$ or CH$_2$—O); an ethylene bond (CH$_2$—CH$_2$); a thioamide bond (C(S)—NH); a trans-olefin bond (CH=CH); a fluoro substituted trans-olefin bond (CF=CH); a ketomethylene bond (C(O)—CHR) or CHR—C(O) wherein R is H or CH$_3$; and a fluoro-ketomethylene bond (C(O)—CFR or CFR—C(O) wherein R is H or F or CH$_3$.

The polypeptides can be further modified by: acetylation, amidation, biotinylation, cinnamoylation, farnesylation, fluoresceination, formylation, myristoylation, palmitoylation, phosphorylation (Ser, Tyr or Thr), stearoylation, succinylation and sulfurylation. As indicated above, peptides can be conjugated to, for example, polyethylene glycol (PEG); alkyl groups (e.g., C1-C20 straight or branched alkyl groups); fatty acid radicals; and combinations thereof.

α,α-Disubstituted non-natural amino acids containing olefinic side chains of varying length can be synthesized by known methods (Williams et al. J. Am. Chem. Soc., 113: 9276, 1991; Schafineister et al., J. Am. Chem. Soc., 122: 5891, 2000; and Bird et al., Methods Enzymol., 446:369, 2008; Bird et al, Current Protocols in Chemical Biology, 2011). For peptides where an i linked to i+7 staple is used (two turns of the helix stabilized) either one S5 amino acid and one R8 is used or one S8 amino acid and one R5 amino acid is used. R8 is synthesized using the same route, except that the starting chiral auxillary confers the R-alkyl-stereoisomer. Also, 8-iodooctene is used in place of 5-iodopentene Inhibitors are synthesized on a solid support using solid-phase peptide synthesis (SPPS) on MBHA resin (see, e.g., WO 2010/148335).

Fmoc-protected α-amino acids (other than the olefinic amino acids Fmoc-S$_5$—OH, Fmoc-R$_8$—OH, Fmoc-R$_8$—OH, Fmoc-S$_8$—OH and Fmoc-R$_5$—OH), 2-(6-chloro-1-H-benzotriazole-1-yl)-1,1,3,3-tetramethylaminium hexafluorophosphate (HCTU), and Rink Amide MBHA are commercially available from, e.g., Novabiochem (San Diego, Calif.). Dimethylformamide (DMF), N-methyl-2-pyrrolidinone (NMP), N,N-diisopropylethylamine (DIEA), trifluoroacetic acid (TFA), 1,2-dichloroethane (DCE), fluorescein isothiocyanate (FITC), and piperidine are commercially available from, e.g., Sigma-Aldrich. Olefinic amino acid synthesis is reported in the art (Williams et al., Org. Synth., 80:31, 2003).

In some instances, peptides can include a detectable label. As used herein, a "label" refers to a moiety that has at least one element, isotope, or functional group incorporated into the moiety which enables detection of the peptide to which the label is attached. Labels can be directly attached (ie, via a bond) or can be attached by a linker (e.g., such as, for example, a cyclic or acyclic, branched or unbranched, substituted or unsubstituted alkylene; cyclic or acyclic, branched or unbranched, substituted or unsubstituted alkenylene; cyclic or acyclic, branched or unbranched, substituted or unsubstituted alkynylene; cyclic or acyclic, branched or unbranched, substituted or unsubstituted heteroalkylene; cyclic or acyclic, branched or unbranched, substituted or unsubstituted heteroalkenylene; cyclic or acyclic, branched or unbranched, substituted or unsubstituted heteroalkynylene; substituted or unsubstituted arylene; substituted or unsubstituted heteroarylene; or substituted or unsubstituted acylene, or any combination thereof, which can make up a linker). Labels can be attached to a peptide at any position that does not interfere with the biological activity or characteristic of the inventive polypeptide that is being detected.

Labels can include: labels that contain isotopic moieties, which may be radioactive or heavy isotopes, including, but not limited to $^2$H, $^3$H, $^{13}$C, $^{14}$C, $^{15}$N, $^{31}$P, $^{32}$P, $^{35}$S, $^{67}$Ga, $^{99}$Tc (Tc-99m), $^{111}$In, $^{123}$I, $^{125}$I, $^{169}$Yb, and $^{186}$Re; labels that include immune or immunoreactive moieties, which may be antibodies or antigens, which may be bound to enzymes (e.g., such as horseradish peroxidase); labels that are colored, luminescent, phosphorescent, or include fluorescent moieties (e.g., such as the fluorescent label FITC); labels that have one or more photoaffinity moieties; labels that have ligand moieties with one or more known binding partners (such as biotin-streptavidin, FK506-FKBP, etc.).

In some instances, labels can include one or more photoaffinity moieties for the direct elucidation of intermolecular interactions in biological systems. A variety of known photophores can be employed, most relying on photoconversion of diazo compounds, azides, or diazirines to nitrenes or carbenes (see, e.g., Bayley, H., Photogenerated Reagents in Biochemistry and Molecular Biology (1983), Elsevier, Amsterdam, the entire contents of which are incorporated herein by reference). In certain embodiments of the invention, the photoaffinity labels employed are o-, m- and p-azidobenzoyls, substituted with one or more halogen moieties, including, but not limited to 4-azido-2,3,5,6-tetrafluorobenzoic acid.

Labels can also be or can serve as imaging agents. Exemplary imaging agents include, but are not limited to, those used in positron emissions tomography (PET), computer assisted tomography (CAT), single photon emission computerized tomography, x-ray, fluoroscopy, and magnetic resonance imaging (MRI); anti-emetics; and contrast agents. Exemplary diagnostic agents include but are not limited to, fluorescent moieties, luminescent moieties, magnetic moieties; gadolinium chelates (e.g., gadolinium chelates with DTPA, DTPA-BMA, DOTA and HP-DO3A), iron chelates, magnesium chelates, manganese chelates, copper chelates, chromium chelates, iodine-based materials useful for CAT and x-ray imaging, and radionuclides. Suitable radionuclides include, but are not limited to $^{123}$I, $^{125}$I, $^{130}$I, $^{131}$I, $^{133}$I, $^{135}$I, $^{47}$Sc, $^{72}$As, $^{72}$Se, $^{90}$Y, $^{88}$Y, $^{97}$Ru, $^{100}$Pd, $^{101}$mRh, $^{119}$Sb, $^{128}$Ba, $^{197}$Hg, $^{211}$At, $^{212}$Bi, $^{212}$Pb, $^{109}$Pd, $^{111}$In, $^{67}$Ga, $^{68}$Ga, $^{67}$Cu, $^{75}$Br, $^{77}$Br, $^{99}$mTc, $^{14}$C, $^{13}$N, $^{15}$O, $^{32}$P, $^{33}$P, and $^{18}$F.

Fluorescent and luminescent moieties include, but are not limited to, a variety of different organic or inorganic small molecules commonly referred to as "dyes," "labels," or "indicators." Examples include, but are not limited to, fluorescein, rhodamine, acridine dyes, Alexa dyes, cyanine dyes, etc. Fluorescent and luminescent moieties may include a variety of naturally occurring proteins and derivatives thereof, e.g., genetically engineered variants. For example, fluorescent proteins include green fluorescent protein (GFP), enhanced GFP, red, blue, yellow, cyan, and sapphire fluorescent proteins, reef coral fluorescent protein, etc. Luminescent proteins include luciferase, aequorin and derivatives thereof. Numerous fluorescent and luminescent dyes and proteins are known in the art (see, e.g., U.S. Patent Publication 2004/0067503; Valeur, B., "Molecular Fluorescence: Principles and Applications," John Wiley and Sons, 2002; and Handbook of Fluorescent Probes and Research Products, Molecular Probes, 9th edition, 2002).

Again, methods suitable for obtaining (e.g., synthesizing), stapling, and purifying the peptides disclosed herein are also known in the art (see, e.g., Bird et. al., Methods in Enzymol., 446:369-386 (2008); Bird et al, Current Protocols in Chemical Biology, 2011; Walensky et al., Science, 305:1466-1470 (2004); Schafineister et al., J. Am. Chem. Soc., 122:5891-5892 (2000); U.S. patent application Ser. No. 12/525,123, filed Mar. 18, 2010; and U.S. Pat. No. 7,723,468, issued May 25, 2010, each of which are hereby incorporated by reference in their entirety) and are described herein (see, e.g., Example 1).

In some embodiments, the peptides are substantially free of non-stapled peptide contaminants or are isolated. Methods for purifying peptides include, for example, synthesizing the peptide on a solid-phase support. Following cyclization, the solid-phase support may be isolated and suspended in a solution of a solvent such as DMSO, DMSO/dichloromethane mixture, or DMSO/NMP mixture. The DMSO/dichloromethane or DMSO/NMP mixture may comprise about 30%, 40%, 50% or 60% DMSO. In a specific embodiment, a 50%/50% DMSO/NMP solution is used. The solution may be incubated for a period of 1, 6, 12 or 24 hours, following which the resin may be washed, for example with dichloromethane or NMP. In one embodiment, the resin is washed with NMP. Shaking and bubbling an inert gas into the solution may be performed.

Properties of the cross-linked polypeptides of the invention can be assayed, for example, using the methods described below.

Assays to Determine α-Helicity:

Compounds are dissolved in an aqueous solution (e.g. 5 mM potassium phosphate solution at pH 7, or distilled $H_2O$, to concentrations of 25-50 μM). Circular dichroism (CD) spectra are obtained on a spectropolarimeter (e.g., Jasco J-710, Aviv) using standard measurement parameters (e.g. temperature, 20° C.; wavelength, 190-260 nm; step resolution, 0.5 nm; speed, 20 nm/sec; accumulations, 10; response, 1 sec; bandwidth, 1 nm; path length, 0.1 cm). The α-helical content of each peptide is calculated by dividing the mean residue ellipticity by the reported value for a model helical decapeptide (Yang et al., Methods Enzymol. 130:208 (1986)).

Assays to Determine Melting Temperature (Tm):

Cross-linked or the unmodified template peptides are dissolved in distilled $H_2O$ or other buffer or solvent (e.g. at a final concentration of 50 μM) and Tm is determined by measuring the change in ellipticity over a temperature range (e.g. 4 to 95° C.) on a spectropolarimeter (e.g., Jasco J-710, Aviv) using standard parameters (e.g. wavelength 222 nm; step resolution, 0.5 nm; speed, 20 nm/sec; accumulations, 10; response, 1 sec; bandwidth, 1 nm; temperature increase rate: 1° C./min; path length, 0.1 cm).

In Vitro Protease Resistance Assays:

The amide bond of the peptide backbone is susceptible to hydrolysis by proteases, thereby rendering peptidic compounds vulnerable to rapid degradation in vivo. Peptide helix formation, however, typically buries and/or twists and/or shields the amide backbone and therefore may prevent or substantially retard proteolytic cleavage. The peptidomimetic macrocycles of the present invention may be subjected to in vitro enzymatic proteolysis (e.g. trypsin, chymotrypsin, pepsin) to assess for any change in degradation rate compared to a corresponding uncrosslinked or alternatively stapled polypeptide. For example, the peptidomimetic macrocycle and a corresponding uncrosslinked polypeptide are incubated with trypsin agarose and the reactions quenched at various time points by centrifugation and subsequent HPLC injection to quantitate the residual substrate by ultraviolet absorption at 280 nm. Briefly, the peptidomimetic macrocycle and peptidomimetic precursor (5 mcg) are incubated with trypsin agarose (Pierce) (S/E~125) for 0, 10, 20, 90, and 180 minutes. Reactions are quenched by tabletop centrifugation at high speed; remaining substrate in the isolated supernatant is quantified by HPLC-based peak detection at 280 nm. The proteolytic reaction displays first order kinetics and the rate constant, k, is determined from a plot of ln [S] versus time.

Peptidomimetic macrocycles and/or a corresponding uncrosslinked polypeptide can be each incubated with fresh mouse, rat and/or human serum (e.g. 1-2 mL) at 37° C. for, e.g., 0, 1, 2, 4, 8, and 24 hours. Samples of differing macrocycle concentration may be prepared by serial dilution with serum. To determine the level of intact compound, the following procedure may be used: The samples are extracted, for example, by transferring 100 μL of sera to 2 ml centrifuge tubes followed by the addition of 10 μL of 50% formic acid and 500 μL acetonitrile and centrifugation at 14,000 RPM for 10 min at 4+/−2° C. The supernatants are then transferred to fresh 2 ml tubes and evaporated on Turbovap under $N_2$<10 psi, 37° C. The samples are reconstituted in 100 μL of 50:50 acetonitrile:water and submitted to LC-MS/MS analysis. Equivalent or similar procedures for testing ex vivo stability are known and may be used to determine stability of macrocycles in serum.

In Vivo Protease Resistance Assays:

A key benefit of peptide stapling is the translation of in vitro protease resistance into markedly improved pharmacokinetics in vivo.

Liquid chromatography/mass spectrometry-based analytical assays are used to detect and quantitate SAH-RSV levels in plasma. For pharmacokinetic analysis, peptides are dissolved in sterile aqueous 5% dextrose (1 mg/mL) and administered to C57BL/6 mice (Jackson Laboratory) by bolus tail vein or intraperitoneal injection (e.g. 5, 10, 25, 50 mg/kg). Blood is collected by retro-orbital puncture at 5, 30, 60, 120, and 240 minutes after dosing 5 animals at each time point. Plasma is harvested after centrifugation (2,500×g, 5 minutes, 4° C.) and stored at −70° C. until assayed. Peptide concentrations in plasma are determined by reversed-phase high performance liquid chromatography with electrospray ionization mass spectrometric detection (Aristoteli et al., Journal of Proteome Res., 6:571-581, 2007; Walden et al., Analytical and Bioanalytical Chem., 378:883-897, 2004). Study samples are assayed together with a series of 7 calibration standards of peptide in plasma at concentrations ranging from 1.0 to 50.0 μg/mL, drug-free plasma assayed with and without addition of an internal standard, and 3 quality control samples (e.g. 3.75, 15.0, and 45.0 μg/mL). Standard curves are constructed by plotting the analyte/internal standard chromatographic peak area ratio against the known drug concentration in each calibration standard. Linear least squares regression is performed with weighting in proportion to the reciprocal of the analyte concentration normalized to the number of calibration standards. Values of the slope and y-intercept of the best-fit line are used to calculate the drug concentration in study samples. Plasma concentration-time curves are analyzed by standard non-compartmental methods using WinNonlin Professional 5.0 software (Pharsight Corp., Cary, N.C.), yielding pharmacokinetic parameters such as initial and terminal phase plasma half-life, peak plasma levels, total plasma clearance, and apparent volume of distribution.

Persistence of stabilized RSV (SAH-RSV) peptides in the nasal mucosa after topical administration (i.e. nose drops) and in the respiratory mucosa after nebulization is examined in the context of pre- and post-infection blockade of viral fusion and dissemination. Mice are exposed to single SAHF treatment by nose drop or nebulizer at a series of intervals preceding intransal infection with rgRSV, and the duration of protection from mucosal infection (assessed histologically as described above) used to measure the relative mucosal stability and prophylactic efficacy of SAHF constructs.

In vitro Binding Assays:

To assess the binding and affinity of peptidomimetic macrocycles and peptidomimetic precursors to acceptor proteins, a fluorescence polarization assay (FPA) can be used, for example. The FPA technique measures the molecular orientation and mobility using polarized light and fluorescent tracer. When excited with polarized light, fluorescent tracers (e.g., FITC) attached to molecules with high apparent molecular weights (e.g. FITC-labeled peptides bound to a large protein) emit higher levels of polarized fluorescence due to their slower rates of rotation as compared to fluorescent tracers attached to smaller molecules (e.g. FITC-labeled peptides that are free in solution).

In Vitro Displacement Assays to Characterize Antagonists of Peptide-Protein Interactions:

To assess the binding and affinity of compounds that antagonize the interaction between a peptide and an acceptor protein, a fluorescence polarization assay (FPA) utilizing a fluoresceinated peptidomimetic macrocycle derived from a peptidomimetic precursor sequence is used, for example. The FPA technique measures the molecular orientation and mobility using polarized light and fluorescent tracer. When excited with polarized light, fluorescent tracers (e.g., FITC) attached to molecules with high apparent molecular weights (e.g. FITC-labeled peptides bound to a large protein) emit higher levels of polarized fluorescence due to their slower rates of rotation as compared to fluorescent tracers attached to smaller molecules (e.g. FITC-labeled peptides that are free in solution). A compound that antagonizes the interaction between the fluoresceinated peptidomimetic macrocycle and an acceptor protein will be detected in a competitive binding FPA experiment.

Binding Assays in Intact Cells:

It is possible to measure binding of peptides or crosslinked polypeptides to their natural acceptors on or in intact cells by immunoprecipation experiments, e.g., as described herein.

Cellular Penetrability Assays:

To measure the cell penetrability of peptides or crosslinked polypeptides, intact cells are incubated with fluoresceinated crosslinked polypeptides (10 μM) for 4 hrs in serum-free media or in media supplemented with human serum at 37° C., washed twice with media and incubated with trypsin (0.25%) for 10 min at 37° C. The cells are washed again and resuspended in PBS. Cellular fluorescence is analyzed, for example, by using either a FACSCalibur flow cytometer or Cellomics' KineticScan® HCS Reader.

Antiviral Efficacy Assays:

The efficiency of SAHF peptides in preventing and treating RSV infection are evaluated in monolayer cultures of Vero and NHBE cells. The concentrations of SAHF peptides that cause a 50% reduction in infection when cell cultures are exposed to an infectious dose of rgRSV of 1 pfu per cell (1 MOI of an engineered version of RSV encoding a GFP reporter) are determined. SAHF peptides are also tested in 3D air-liquid interface cell cultures, as described[71]. 3D cells are infected with an estimated dose of 5-10 MOI and the efficiency of SAHF inhibition of rgRSV infection examined at days 1, 3 and 5 post-infection. Cultures are mounted on OCT and frozen sections examined for inhibition of GFP expression. The characteristic inflammatory markers induced by RSV infection are also examined. For in vivo efficacy testing, the intranasal rgRSV infection model of immunocompromised BALB/c mice is employed, as described[72,73]. The inhibitory effects of SAHF peptides, when administered either before, during, or after RSV infection are examined by fluorescence microscopy and quantified using image J (NIH). The effect of SAHF treatment on pulmonary spread of infection is also examined by microscopic evaluation of lung tissue.

Additional RSV infectivity assays employ Hep-G2 cells, plated at 40,000 cells/per well in a 24-well plate, and treated with stapled peptides 15 min prior to infection with 0.1 MOI wild-type RSV. The Hep-2 cells are infected for 2 hr at 37 C and the medium replaced with fresh 5% DMEM along with 5 uM of the respective stapled peptides. The cells are then fixed in 4% paraformaldehyde for 15 min, washed and treated with 1:100 dilution of F-antibody conjugated with Alexa 488 for 2 h at room temperature. Cells are washed and treated with DAPI and Alexa 488-positive (F-positive cells) are counted. The percentage of F-positive cells is determined from the total cells counted in one field. Four different fields are counted and the average taken and plotted with SE as error bars. To measure the effect of SAHF treatment on RSV titers, supernatants from Vero cells treated with 5 uM peptides and infected with 0.1 MO RSV are collected and applied to Hep-2 cells by serial dilution (e.g. 1:1, 1:10, 1:100, etc). Cellular plaques are then counted 4 days post-infection as a measure of RSV titers in the supernatants of SAHF-peptide treated Vero cells vs. control.

Clinical Trials:

To determine the suitability of the cross-linked polypeptides of the invention for treatment of humans, clinical trials can be performed. For example, patients exposed to RSV infection or diagnosed with RSV infection are selected and separated in treatment and one or more control groups, wherein the treatment group is administered a crosslinked polypeptide of the invention, while the control groups receive a placebo or a known antiviral drug. The treatment safety and efficacy of the cross-linked polypeptides of the invention can thus be evaluated by performing comparisons of the patient groups with respect to factors such as prevention of symptoms, time to resolution of symptoms, and/or overall infection severity. In this example, the RSV-exposed patient group treated with a cross-linked polypeptide would avoid the development of infection, or a patient group with RSV infection would show resolution of or relief from symptoms compared to a patient control group treated with a placebo.

Pharmaceutical Compositions

One or more of the stabilized peptides disclosed herein (e.g., one or more of SEQ ID NOs: 1-26) can be formulated for use as or in pharmaceutical compositions. Such compositions can be formulated or adapted for administration to a subject via any route, e.g., any route approved by the Food and Drug Administration (FDA). Exemplary methods are described in the FDA's CDER Data Standards Manual, version number 004 (which is available at fda.give/cder/dsm/DRG/drg00301.htm). For example, compositions can be formulated or adapted for administration by inhalation (e.g., oral and/or nasal inhalation (e.g., via nebulizer or spray)), injection (e.g., intravenously, intra-arterial, subdermally, intraperitoneally, intramuscularly, and/or subcutaneously); and/or for oral administration, transmucosal administration, and/or topical administration (including topical (e.g., nasal) sprays and/or solutions).

In some instances, pharmaceutical compositions can include an effective amount of one or more stabilized peptides. The terms "effective amount" and "effective to treat," as used herein, refer to an amount or a concentration of one or more compounds or a pharmaceutical composition described herein utilized for a period of time (including acute or chronic administration and periodic or continuous administration) that is effective within the context of its administration for causing an intended effect or physiological outcome (e.g., prophylaxis or treatment of RSV infection).

Pharmaceutical compositions of this invention can include one or more peptides and any pharmaceutically acceptable carrier, adjuvant and/or vehicle. In some instances, pharmaceuticals can further include one or more additional therapeutic agents in amounts effective for achieving a modulation of disease or disease symptoms.

In some instances, pharmaceuticals of the present disclosure can include one or more medicaments for the treatment of RSV or the alleviation of symptoms associated with RSV (e.g., one or more medicaments approved or awaiting approval by the Federal Drug Administration). Exemplary medicaments can include, for example, antivirals (e.g., Ribavirin), antibodies, including monoclonal antibodies (e.g., palivizumab, Motavizumab), small molecules, steroids and corticosteroids, antibiotics, bronchodilators, acetaminophen (e.g., Tylenol™ and others), and ibuprofen (e.g., Advil™, Motrin™, and others). Other medicaments suitable for use in the present disclosure are known in the art (see, e.g., Maggon and Barik, Rev. Med. Virol., 14(3):149-168 (2004)).

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, may also be advantageously used to enhance delivery of compounds of the formulae described herein.

The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intra-cutaneous, intra-venous, intra-muscular, intra-articular, intra-arterial, intra-synovial, intra-sternal, intra-thecal, intra-lesional and intra-cranial injection or infusion techniques.

Pharmaceutical compositions can be in the form of a solution or powder for inhalation and/or nasal administration. Such compositions may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

Pharmaceutical compositions can be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

Alternatively or in addition, pharmaceutical compositions can be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

In some embodiments, the present disclosure provides methods for using any one or more of the peptides or pharmaceutical compositions (indicated below as 'X') disclosed herein in the following methods:

Substance X for use as a medicament in the treatment of one or more diseases or conditions disclosed herein (e.g., cancer, referred to in the following examples as 'Y'). Use of substance X for the manufacture of a medicament for the treatment of Y; and substance X for use in the treatment of Y.

In some instances, one or more of the peptides herein can be formulated as an immunostimulatory composition (e.g., a vaccine), e.g., for vaccination or immunization of a subject.

Immunostimulatory compositions can include additional components tailored for a vaccine. Additional components tailored for vaccines can include adjuvants, preservatives, and additives. Exemplary adjuvants include agents that increase the immune response of a subject immunized with a vaccine to the vaccine, without promoting a specific immunologic response against itself. Adjuvants can include any substance that acts to accelerate, prolong, or enhance antigen-specific immune responses when used in combination with specific vaccine antigens. Specific examples can include aluminum gels, aluminum salts, Squalene, acylated and deacylated saponins (see, e.g., U.S. Pat. No. 7,858,098), oil-based adjuvants, virosomes, aluminum hydroxide, QS-21, TITERMAX™ (CytRx Corp., Norcross Ga.), Freund's complete adjuvant, Freund's incomplete adjuvant, interleukin-2, thymosin, and the like. Preservatives can be included to limit or prevent microbial growth or contamination in a vaccine (e.g., a packaged vaccine). Exemplary preservatives can include, but are not limited to, Thimerosal, Benzethonium chloride (Phemerol), Phenol, 2-phenoxyethanol. Exemplary additives can include formaldehyde, human serum albumin, gelatin, antibiotics and yeast proteins.

In some instances, one or more peptides disclosed herein can be conjugated, for example, to a carrier protein. Such conjugated compositions can be monovalent or multivalent. For example, conjugated compositions can include one peptide disclosed herein conjugated to a carrier protein. Alternatively, conjugated compositions can include two or more peptides disclosed herein conjugated to a carrier. In such instances, additional immunostimulatory components can also be coupled to the carrier protein.

As used herein, when two entities are "conjugated" to one another they are linked by a direct or indirect covalent or non-covalent interaction. In certain embodiments, the association is covalent. In other embodiments, the association is non-covalent. Non-covalent interactions include hydrogen bonding, van der Waals interactions, hydrophobic interactions, magnetic interactions, electrostatic interactions, etc. An indirect covalent interaction is when two entities are covalently connected, optionally through a linker group.

Carrier proteins can include any protein that increases or enhances immunogenicity in a subject. Exemplary carrier proteins are described in the art (see, e.g., Fattom et al., Infect. Immun., 58:2309-2312, 1990; Devi et al., Proc. Natl. Acad. Sci. USA 88:7175-7179, 1991; Li et al., Infect. Immun. 57:3823-3827, 1989; Szu et al., Infect. Immun. 59:4555-4561, 1991; Szu et al., J. Exp. Med. 166:1510-1524, 1987; and Szu et al., Infect. Immun. 62:4440-4444, 1994). Polymeric carriers can be a natural or a synthetic material containing one or more primary and/or secondary amino groups, azido groups, or carboxyl groups. Carriers can be water soluble.

For vaccines, effective amounts include a dose that promotes antibody production in an immunized subject. Antibody production can be assessed using an antibody titer assays.

In some instances, a vaccine composition can contain an effective, immunogenic amount of a vaccine. For example, the effective amount of a vaccine can be the amount of vaccine required to induce an immune response to RSV in a subject. Although effective amounts can depend, among other things, on the species of subject inoculated, the body weight of the subject and the chosen inoculation regimen, effective amounts can be readily determined. One or more peptides disclosed herein can be formulated for sale in the US, import into the US, and/or export from the US.

Methods of Treatment

The disclosure includes methods of using the peptides herein for the prophylaxis and/or treatment of RSV infection. The terms "treat" or "treating," as used herein, refers to partially or completely alleviating, inhibiting, ameliorating, and/or relieving the disease or condition from which the subject is suffering. In some instances, treatment can result in the continued absence of detectable RSV infection in a subject, or a reduction in the level of RSV infection in a subject.

In general, methods include selecting a subject and administering to the subject an effective amount of one or more of the peptides herein, e.g., in or as a pharmaceutical composition, and optionally repeating administration as required for the prophylaxis or treatment of RSV infection.

Selecting a subject can include selecting a subject at risk for RSV infection and/or exposed to RSV infection and/or those infected with RSV. The term "subject," as used herein, refers to any animal. In certain embodiments, the subject is a mammal. In certain embodiments, the term "subject", as used herein, refers to a human (e.g., a man, a woman, or a child). Subjects at risk for RSV infection include those that may come into contact with RSV and/or have contacted a subject with RSV. Contact with RSV can occur, for example, during an RSV outbreak (e.g., in a finite geographical location), in a healthcare facility (e.g., a community clinic, a vaccination center, a doctors' office), in an outpatient facility, in a hospital (e.g., in an inpatient facility, in an intensive care unit), in an assisted living facility. Subjects can also include those scheduled to attend a healthcare facility or geographical area where infection by RSV may occur. Subjects can be referred by a medical practitioner or can be self-referred. In some instances, a level of RSV can be detected in a subject. Such levels of RSV can be used during treatment to detect a change in the level of RSV.

The terms "administer," "administering," or "administration," as used herein refers to implanting, absorbing, ingesting, injecting, or inhaling, the inventive polypeptide or compound. In some instances, one or more of the peptides disclosed herein can be administered to a subject topically (e.g., nasally) and/or orally. For example, the methods herein include administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. In some embodiments, an effective dose of one or more of the peptides herein can include, but is not limited to, for example, about, 0.00001, 0.0001, 0.001, 0.01, 0.1, 1 or 10-10000; 0.00001, 0.0001, 0.001, 0.01, 0.1, 1 or 10-5000; 0.00001, 0.0001, 0.001, 0.01, 0.1, 1 or 10-2500; 0.00001, 0.0001, 0.001, 0.01, 0.1, 1 or 10-1000; 0.00001, 0.0001, 0.001, 0.01, 0.1, 1 or 10-900; 0.00001, 0.0001, 0.001, 0.01, 0.1, 1 or 10-800; 0.00001, 0.0001, 0.001, 0.01, 0.1, 1 or 10-700; 0.00001, 0.0001, 0.001, 0.01, 0.1, 1 or 10-600; 0.00001, 0.0001, 0.001, 0.01, 0.1, 1 or 10-500; 0.00001, 0.0001, 0.001, 0.01, 0.1, 1 or 10-400; 0.00001, 0.0001, 0.001, 0.01, 0.1, 1 or 10-300; 0.00001, 0.0001, 0.001, 0.01, 0.1, 1 or 10-200; 0.00001, 0.0001, 0.001, 0.01, 0.1, 1 or 10-100; 0.00001, 0.0001, 0.001, 0.01, 0.1, 1 or 10-90; 0.00001, 0.0001, 0.001, 0.01, 0.1, 1 or 10-80; 0.00001, 0.0001, 0.001, 0.01, 0.1, 1 or 10-70; 0.00001, 0.0001, 0.001, 0.01, 0.1, 1 or 10-60; 0.00001, 0.0001, 0.001, 0.01, 0.1, 1 or 10-50; 0.00001, 0.0001, 0.001, 0.01, 0.1, 1 or 10-40; 0.00001, 0.0001, 0.001, 0.01, 0.1, 1 or 10-30; 0.00001, 0.0001, 0.001, 0.01, 0.1, 1 or 10-20; 0.00001, 0.0001, 0.001, 0.01, 0.1, 1 or 10-30; 0.00001, 0.0001, 0.001, 0.01, 0.1, 1-15, 0.00001, 0.0001, 0.001, 0.01, 0.1, 1 or 10-30; 0.00001, 0.0001, 0.001, 0.01, 0.1, 1-10, 0.00001, 0.0001, 0.001, 0.01, 0.1, 1 or 10-30; or 0.00001, 0.0001, 0.001, 0.01, 0.1, 1-5 mg/kg/day.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Following administration, the subject can be evaluated to detect, assess, or determine the level of RSV infection in the subject. In some instances, treatment can continue until a change (e.g., reduction) in the level of RSV infection in the subject is detected.

Upon improvement of a patient's condition (e.g., a change (e.g., decrease) in the level of RSV infection in the subject), a maintenance dose of a compound, composition or combination of this invention may be administered, if necessary. Subsequently, the dosage or frequency of administration, or both, may be reduced, as a function of the symptoms, to a level at which the improved condition is retained. Patients may, however, require intermittent treatment on a long-term basis upon any recurrence of disease symptoms.

Vaccination Methods

Peptides and compositions can be administered as a prophylactic (e.g., as a vaccine). Methods include contacting a subject at risk for exposure to RSV with an effective amount of one or more of the peptides and/or pharmaceutical compositions disclosed herein (e.g., formulated as an immunostimulatory composition). Methods can also include determining whether a level of immunity (e.g., RSV) is present in the subject prior to, during, and following administration of the peptides or pharmaceutical composition.

An effective amount can be administered in one or more administrations, applications or dosages. A therapeutically effective amount of a therapeutic compound (I.e., an effective dosage) depends on the therapeutic compounds selected. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the therapeutic compounds described herein can include a single treatment or a series of treatments. For example, effective amounts can be administered at least once. In order to increase the antibody level, a second or booster (e.g., third, fourth, or more) dose may be administered, e.g., approximately 1, 2, 3, 4, 5, 6, 7, 8, 9, 10, or more weeks after the initial injection. Subsequent doses may be administered as indicated. The use of an immunoadjuvant may increase the responses magnitude and duration. Immunization could be parenteral transcutanous, or oral, or could part of a prime boost protocol, including orally priming with oral cholera vaccine, followed by parenteral or cutenous boosting of a cholera conjugate vaccine.

Screening Methods

Peptides disclosed herein can be used in screening methods to detect agents that bind to RSV-F.

In some instances, screening methods include competitive screening assays. For example, methods can include determining whether an agent alters (e.g., reduces) binding of one or more of the peptides disclosed herein to RSV-F (e.g., to RSV 5-helix bundle). In some instances, methods can include (i) determining a level of binding between one or more of the peptides disclosed herein and RSV-F (e.g., to RSV 5-helix bundle) (e.g., in the absence of an agent); and (ii) detecting the level of binding between one or more peptides (e.g., the one or more peptides of (i)) and RSV-F (e.g., to RSV 5-helix bundle) in the presence of an agent, wherein a change (e.g., reduction) in the level of binding between the one or more peptides and RSV-F (e.g., RSV 5-helix bundle) indicates that the agent is a candidate agent that binds to RSV-F; and (iii) selecting the candidate agent. In some instances, (i) can include contacting one or more peptides with RSV-F (e.g., to RSV 5-helix bundle) and detecting the level of binding between one or more peptides with RSV-F (e.g., to RSV 5-helix bundle). (ii) can include contacting the one or more peptides and the agent with RSV-F (e.g., to RSV 5-helix bundle) and detecting the level of binding between one or more peptides with RSV-F (e.g., to RSV 5-helix bundle). RSV-F (e.g., to RSV 5-helix bundle) can be contacted with the one or more peptides and the agent at the same time or at different times (e.g., the one or more peptides can be contacted with RSV-F (e.g., to RSV 5-helix bundle) before or after the agent). In some embodiments, candidate agents can be administered to a suitable animal model (e.g., an animal model of RSV) to determine if the agent reduces a level of RSV infection in the animal.

In some instances, one or both of the peptide and the RSV 5-helix bundle can include a label.

EXAMPLES

The invention is further described in the following examples, which do not limit the scope of the invention described in the claims.

Example 1: Construction of RSVF Stapled Peptides

Figure 3C:
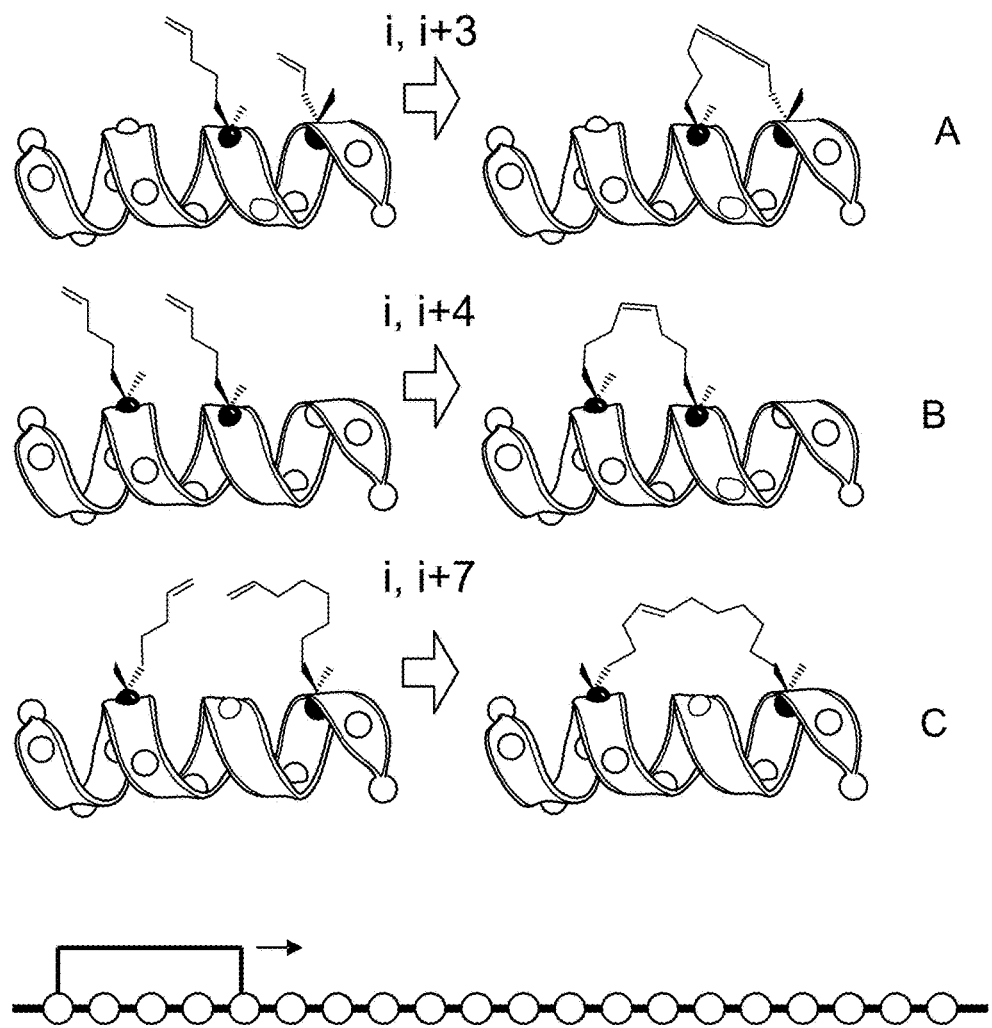
FIG. 3C|A variety of single staple compositions spanning i, i+3; i, i+4, and i, i+7 positions and single staple scanning to generated a library of singly stapled RSV-F peptides.
Figure 3D:
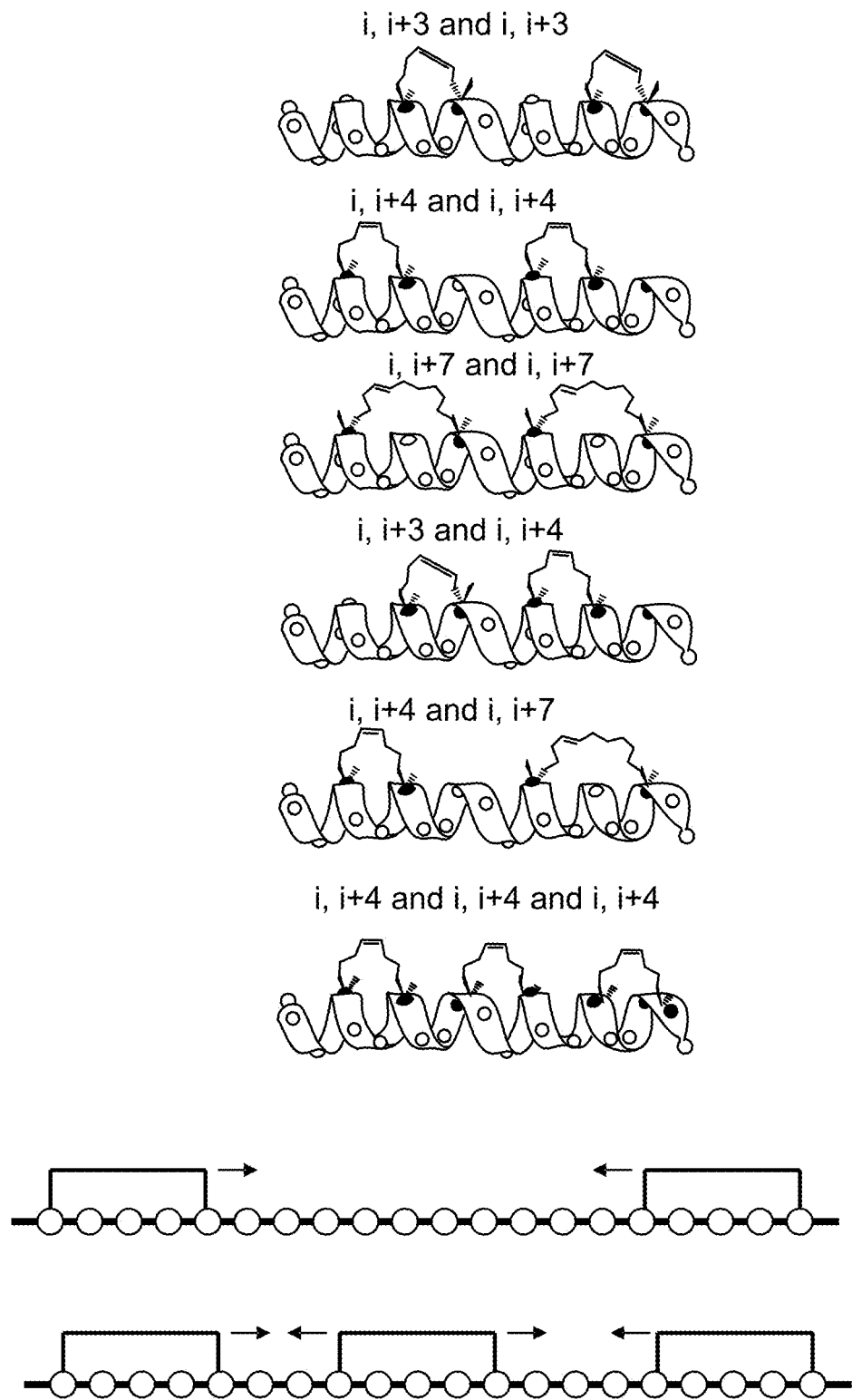
FIG. 3D|A variety of staple compositions in multiply stapled peptides and staple scanning to generated a library of multiply stapled RSV-F peptides.
Figure 3E:
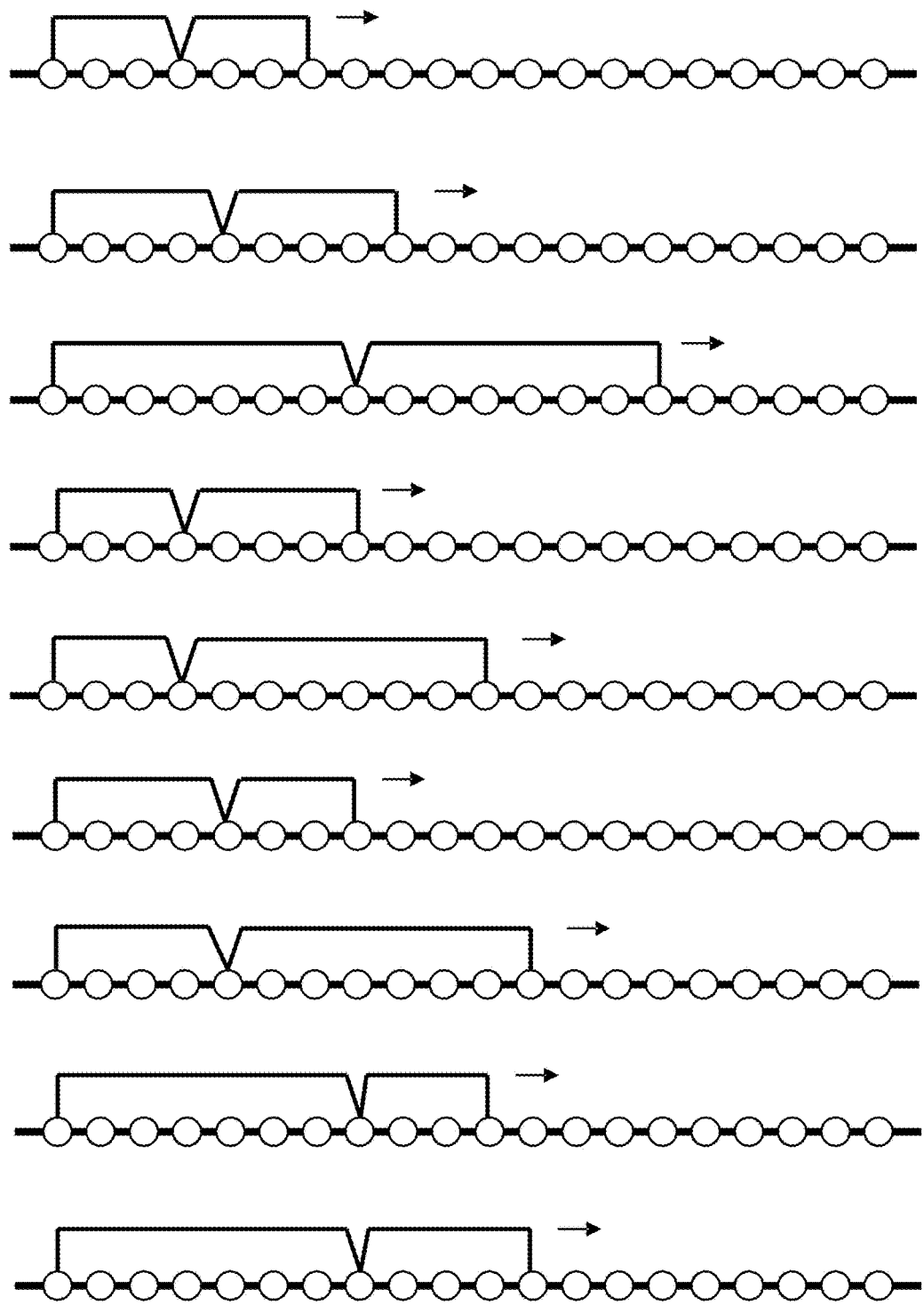
FIG. 3E shows a variety of staple compositions in tandem stapled peptides and staple scanning to generated a library of tandemly stapled RSV-F peptides.

A series of differentially localized chemical staples were located within the RSV-F HR2 domain (i.e., amino acids 488-522 of the sequence publically accessible in the National Center for Biotechnology Information (NCBI) database under ADZ95777 (e.g., version 1) by replacing native residues with non-natural olefinic residues ("X") at select (i, i+4) or (i, i+7) positions, followed by ruthenium-catalyzed olefin metathesis (see, e.g., Table 2 and FIG. 3). Optimal designs incorporate staples on the non-interacting amphiphilic face of the helix or at positions at the border of the hydrophobic interaction face with the amphiphilic face of the helix (FIGS. 2A and 2B).

SAHFs were designed by replacing two naturally occurring amino acids with the non-natural S5 amino acids at i, i+4 positions (i.e. flanking 3 amino acids) to generate a staple spanning one α-helical turn, or a combination of R8 and S5 at i, i+7 positions, respectively, to generate a staple spanning two α-helical turns.

Asymmetric syntheses of α,α-disubstituted amino acids were performed as previously described in detail (Schafmeister et al., J. Am. Chem. Soc., 122:5891-5892, 2000; Walensky et al., Science, 305:1466-1470, 2004; Bird et al. Current Protocols in Chemical Biology, 2011).

Alanine scanning and "staple scanning" was performed to respectively identify residues and binding surfaces critical for interaction, which dictates the design of optimized constructs and negative control mutants (see FIG. 3). The N-termini of SAHs are capped with acetyl or a fluorophore (e.g. FITC, rhodamine), depending upon the experimental application.

Doubly stapled peptides are generated by installing two-S5-S5, two-R8-S5, or other combinations of crosslinking non-natural amino acids (see FIG. 3). Multiply stapled or stitched peptides are generated using similar principles.

TABLE 2

Stapled RSV HR2 Peptides

| Name | Sequence (X, *, and/or 8 show amino acids with crosslinked side chains) | SEQ ID NO |
|---|---|---|
| RSV HR2 (488-522)$_{WT}$ | FDASISQVNEKINQSLAFIRKSDELLHNVNAGKST | 2 |
| SAHF-A | FXASIXQVNEKINQSLAFIRKSDELLHNVNAGKST | 3 |
| SAHF-B | FDXSISXVNEKINQSLAFIRKSDELLHNVNAGKST | 4 |
| SAHF-C | FDAXISQXNEKINQSLAFIRKSDELLHNVNAGKST | 5 |
| SAHF-D | FDASISQVNEKINQSLAFIRKSXELLXNVNAGKST | 6 |
| SAHF-C, D | FDAXISQXNEKINQSLAFIRKSXELLXNVNAGKST | 7 |
| SAHF-E | FDASISQVNEKINQSLAFIRKSDXLLHXVNAGKST | 8 |
| SAHF-F | FDASISQVNEKINQSLAFIRKSDEXLHNXNAGKST | 9 |
| SAHF-G | F8ASISQVXEKINQSLAFIRKSDELLHNVNAGKST | 10 |
| SAHF-H | FD8SISQVNXKINQSLAFIRKSDELLHNVNAGKST | 11 |
| SAHF-I | FDA8SQVVNEXINQSLAFIRKSDELLHNVNAGKST | 12 |
| SAHF-J | FDASISQVNEKINQSLAFI8KSDELLXNVNAGKST | 13 |
| SAHF-K | FDASISQVNEKINQSLAFIR8SDELLHXVNAGKST | 14 |
| SAHF-L | FDASISQVNEKINQSLAFIRK8DELLHNXNAGKST | 15 |
| SAHF-M | FDASISQVNEKINQSLAFIRKS8ELLHNVXAGKST | 16 |
| SAHF-N | FDASISQVNEKINQSLAFIRKSD8LLHNVNXGKST | 17 |
| SAHF-O | FDASISQVNEKINQSLAFIRKSDE8LHNVNAXKST | 18 |
| SAHF-G, J | F8ASISQVXEKINQSLAFI8KSDELLXNVNAGKST | 19 |
| SAHF-H, J | FD8SISQVNXKINQSLAFI8KSDELLXNVNAGKST | 20 |
| SAHF-I, J | FDA8ISQVNEXINQSLAFI8KSDELLXNVNAGKST | 21 |
| SAHF-G, K | F8ASISQVXEKINQSLAFIR8SDELLHXVNAGKST | 22 |
| SAHF-H, K | FD8SISQVNXKINQSLAFIR8SDELLHXVNAGKST | 23 |
| SAHF-I, K | FDA8ISQVNEXINQSLAFIR8SDELLHXVNAGKST | 24 |
| SAHF-H, L | FD8SISQVNXKINQSLAFIRK8DELLHNXNAGKST | 25 |
| SAHF-I, L | FDA8ISQVNEXINQSLAFIRK8DELLHXVNAGKST | 26 |

Synthesis of the SAHF peptides shown in Table 2 was performed using solid phase Fmoc chemistry and ruthenium-catalyzed olefin metathesis, followed by peptide deprotection and cleavage, purification by reverse phase high performance liquid chromatography/mass spectrometry (LC/MS), and quantification by amino acid analysis (AAA) (Bird et al., Methods Enzymol., 446:369-386, 2008).

Example 2: Alpha-Helical Stabilization of RSVF Stapled Peptides

Generally, short peptides do not exhibit significant α-helical structure in solution because the entropic cost of maintaining a conformationally restricted structure is not overcome by the enthalpic gain from hydrogen bonding of the peptide backbone. To document secondary structure improvements of hydrocarbon-stapled peptides, circular dichroism (CD) spectra was recorded and analyzed on a Model 410 Aviv Biomedical spectrometer (Walensky, supra; Bird, supra). A total of five scans from 190-260 nm in 0.5 nm increments with 0.5 sec averaging time are collectively averaged to obtain each spectrum using a 1 mm path length cell. The target peptide concentration for CD studies is 25-50 µM in 50 mM potassium phosphate (pH 7.5) or Milli-Q deionized water, and exact concentrations are confirmed by quantitative AAA of two CD sample dilutions. The CD spectra are initially plotted as wavelength versus millidegree. Once the precise peptide concentration is confirmed, the mean residue ellipticity [θ], in units of degree·cm2·dmol−1·residue−1, is derived from the equation, [θ]=millidegree/molar concentration/number of amino acid residues. After conversion to mean residue ellipticity, percent α-helicity can be calculated using the equation, % helicity=100×[θ]222/max[θ]222, where max[θ]222=−40,000×[1−(2.5/number of amino acid residues)]. SAHF constructs that reinforce α-helical structure can be advanced to protease-resistance testing and cellular uptake analyses.

As shown in FIG. 4B, whereas unmodified RSV HR2 domain was predominantly unstructured in aqueous solution (pH 7, 35° C.), exhibiting ~23% α-helicity, select stapled derivatives displayed greater than 2.5 fold enhancement in helical character, with percent α-helicities all over 55%. As is also apparent from FIG. 4B, insertion of hydrocarbon staples also consistently transformed the circular dichroism spectra from a random coil pattern with a predominant single minimum at 204 nm to an α-helical contour with double minima at 208 and 222 nm.

Example 3: Protease Resistance of SAHF Peptides

Linear peptides are susceptible to rapid proteolysis in vitro and in vivo, limiting the application of natural peptides for mechanistic analyses and therapeutic use. In contrast, amide bonds engaged in the hydrogen-bonding network of a structured peptide helix are poor enzymatic substrates, as are residues shielded by the hydrocarbon staple itself (Bird et al, PNAS, 2010). To evaluate the relative protease resistance conferred by hydrocarbon stapling, in vitro proteolytic degradation was measured by LC/MS (Agilent 1200) using the following parameters: 20 µL injection, 0.6 mL flow rate, 15 min run time consisting of a gradient of water (0.1% formic acid) to 20-80% acetonitrile (0.075% formic acid) over 10 min, 4 min wash to revert to starting gradient conditions, and 0.5 min post-time. The DAD signal is set to 280 nm with an 8 nm bandwidth and MSD set to scan mode with one channel at (M+2H)/2, +/−1 mass units and the other at (M+3H)/3, +/−1 mass units. Integration of each MSD signal yields areas under the curve of >$10^8$ counts. Reaction samples were composed of 5 µL peptide in DMSO (1 mM stock) and 195 µL of buffer consisting of 5 mM phosphate buffer pH 7.4 containing 2 mM $CaCl_2$. Upon injection of the 0 hr time point sample, 2 µL of 50 ng/µL chymotrypsin (Sigma) was added and the amount of intact peptide quantitated by serial injection over time. An internal control of acetylated tryptophan carboxamide at a concentration of 100 µM was used to normalize each MSD data point. A plot of MSD area versus time yields an exponential decay curve and half-lives are determined by nonlinear regression analysis using Prism software (GraphPad).

As shown in FIG. 10, SAHF peptides demonstrate markedly enhanced protease resistance compared to the unmodified peptide template. Doubly stapled peptides exhibit the most dramatic protease resistance.

Example 3: Improved RSV Binding Activity of SAHF Peptides

To assess binding activity toward the RSV fusogenic bundle, competition FPA was performed using recombinant five-helix bundle protein, fluorescent HR2 peptide (488-522), and serial dilutions of SAHF peptides shown in Table 2. More specifically, a 5-helix bundle protein was designed containing five of the six helices that comprise the core of the RSV-F trimer of hairpins, connected by short peptide linkers in accordance with the design of the gp41 5-helix bundle (Root et al., Science, 291:884-888, 2001). Because the 5-helix bundle lacks the third HR2 helix but is otherwise soluble, stable, and helical, incorporation of the sixth HR2 peptide in the form of FITC-RSV (488-522) yielded a stable complex, which can be competed with acetylated SAH-RSV peptides to gauge relative binding affinity.

FPA assays were used to measure and compare the relative binding activities of distinct SAHF constructs for the RSV fusion bundle. First, FITC-RSV HR2 peptide (488-522) is mixed with a serial dilution of recombinant 5-helix bundle protein to generate a binding isotherm. A fixed concentration of FITC-peptide and protein at ~EC75 was then incubated with a serial dilution of acetylated SAHF peptide to generate competition curves for comparative analysis. Fluorescence polarization (mP units) was measured on a SpectraMax fluorimeter and IC50 values calculated by nonlinear regression analysis of competition curves using Prism software (Graphpad).

Figures 4C, 4D:
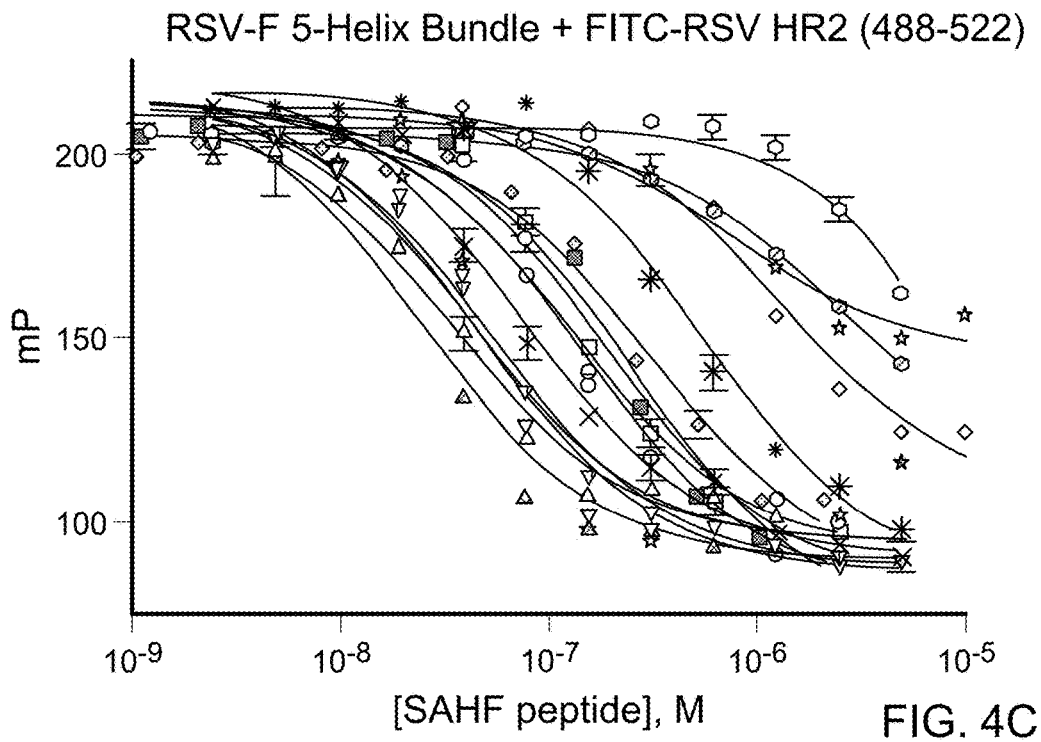
FIG. 4C|A graph of binding isotherms showing that a subgroup of SAHF peptide demonstrate markedly enhanced target (5-helix RSV bundle) binding activity compared to the unmodified template peptide.
FIG. 4D|A table showing IC50 and 95% confidence interval (CI) data for various peptides shown in FIG. 4A and Table 2.
Figures 9A, 9B, 9C:
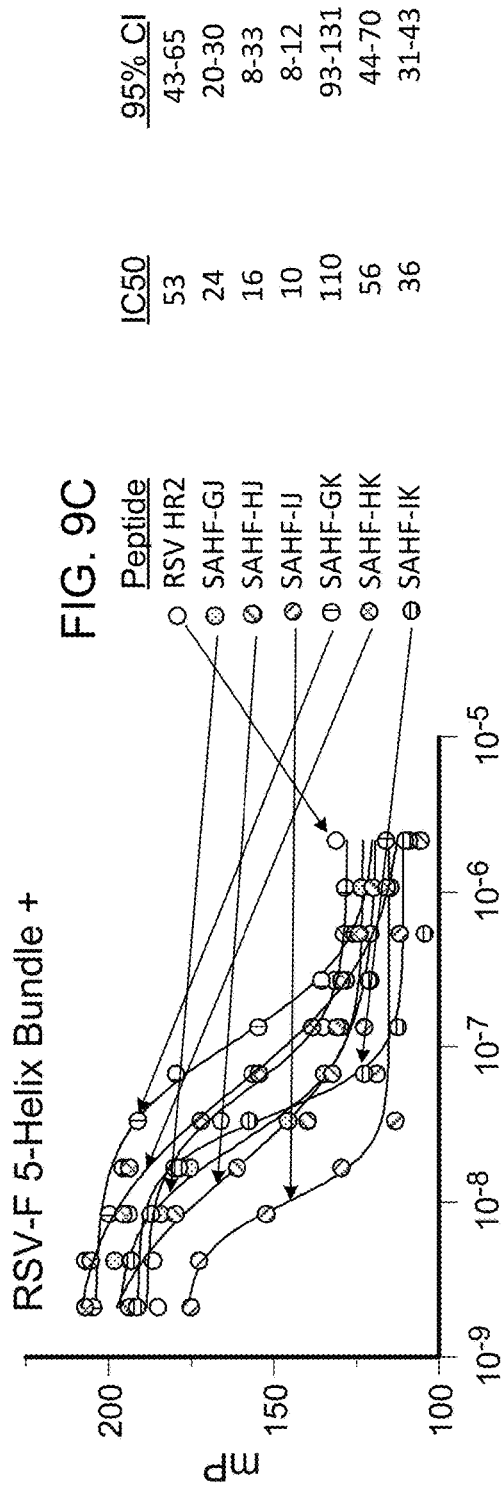
FIG. 9A|A table depicting exemplary doubly stapled i, i+7 peptides (SEQ ID NOs: 2 and 19-26).
FIG. 9B|A line graph showing that doubly stapled i, i+7 peptides target the 5-helix RSV bundle with enhanced affinity compared to the unmodified peptide.
FIG. 9C|A table showing IC50 and 95% CI data for SEQ ID NOs: 2 and 19-26.

As shown in FIGS. 4C and 9B, generating and screening a library of SAHF peptides containing single and double staples of distinct location and composition revealed a series of singly and doubly stapled i, i+7 peptides, SAH-RSV(G), (H), (I), (J), (K), (N), (G, J (SEQ ID NO:19)), (H, J SEQ ID NO:20)), (I, J SEQ ID NO:21)), (I, K SEQ ID NO:22)) (see Table 2), with up to 5-fold enhancement in competitive binding activity. Among the singly stapled i, i+7 constructs, SAH-RSV(L) exhibited poor binding activity, consistent with the location of its staple at the binding interface and the resultant disruption of key native interactions.

These data highlight the capacity of hydrocarbon stapling to both optimize binding activity and probe binding determinants.

In addition, inactive SAHF peptides are readily identified for use as ideal negative controls in biological experiments.

Example 4: Antiviral Activity of RSV F Stapled Peptides Correlates with RSV-SFB Binding To test the capacity of SAHF peptides to block RSV infection of culture cells, an in vitro infectivity assay was performed in the presence and absence of SAHF peptides. Briefly, Vero cells plated in 48-well format (60,000 cells/well) were exposed to rgRSV only (0.1 MOI) and SAHF peptides, followed by imaging 24 hour post-infection to quantitate infectivity by confocal microscopy and FACS analysis Annexin V staining was also performed on harvested Vero cells to distinguish live from dead cells when calculating percent GFP positive cells.

Figure 5:
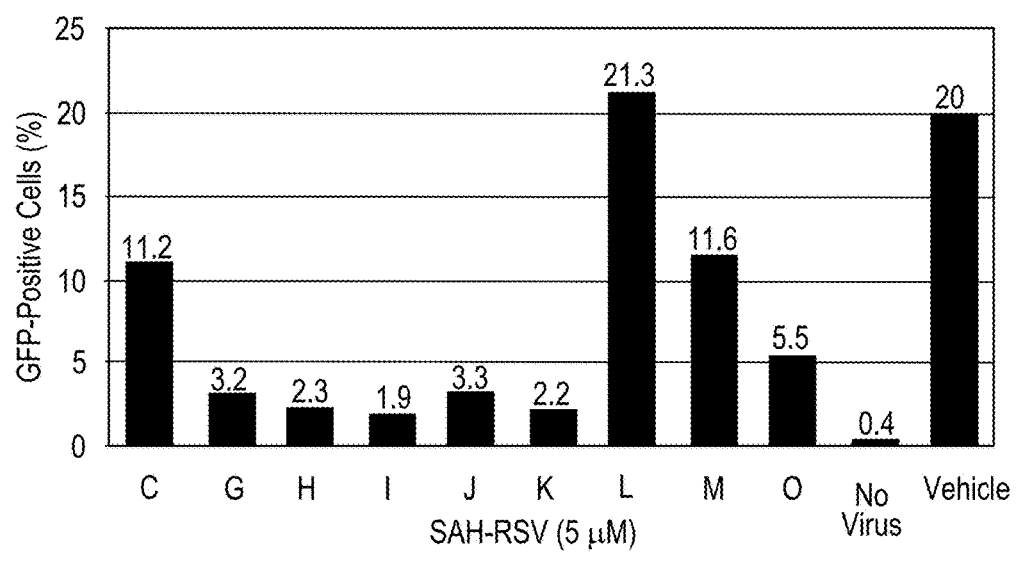
Figures 6C, 7:
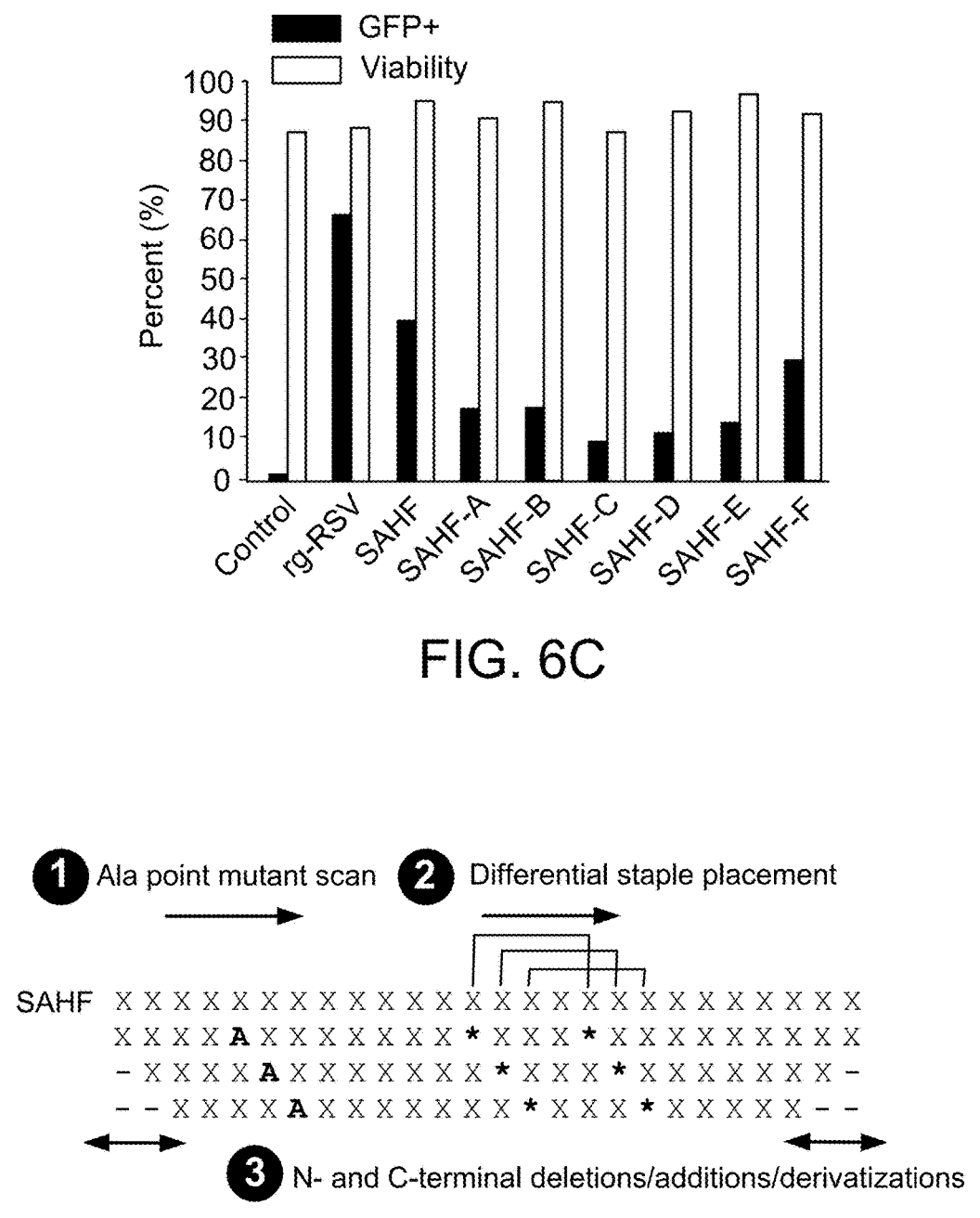

As shown in FIGS. 5 and 6C, SAHF treatment inhibited RSV infection in a manner that correlated with the in vitro RSV SFB binding efficacy (FIG. 4C). For example, SAH-RSV(G), (H), (I), (J), (K) constructs all exhibited superior 5-helix bundle binding and anti-RSV activity, whereas SAH-RSV(L), which is incapable of binding the 5-helix bundle due to placement of the staple at the binding interface, likewise showed no activity in the RSV infectivity assay.

Figure 11A:
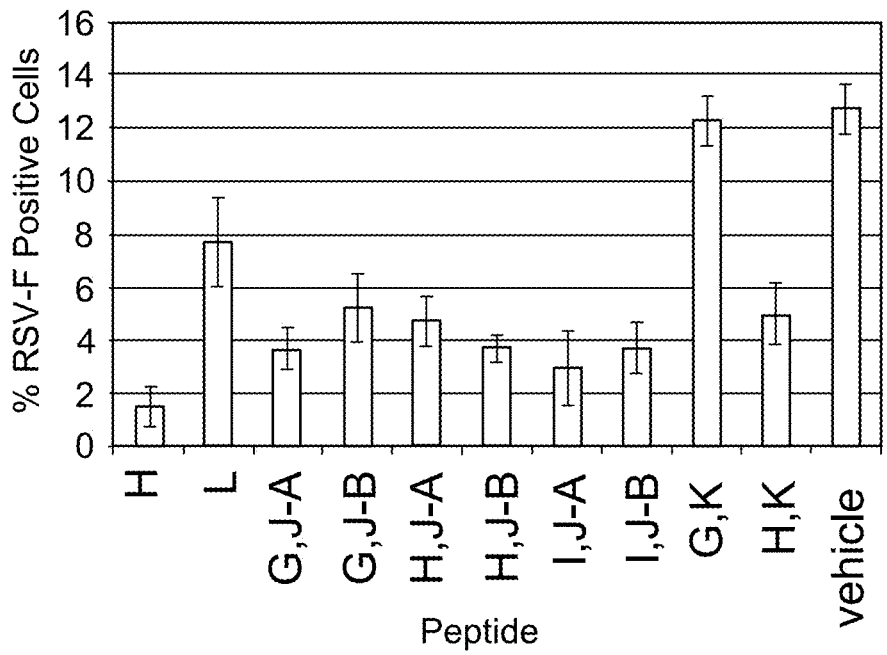
FIGS. 11A-11B|Bar graphs showing that select singly and doubly stapled SAHF peptides effectively suppress RSV infectivity as demonstrated by a decrease in (A) percent RSVF-positive cells and (B) wild-type RSV titers in Hep-2 cells exposed to 0.1 MOI wild-type RSV in the presence of 5 uM peptides.
Figure 11B:
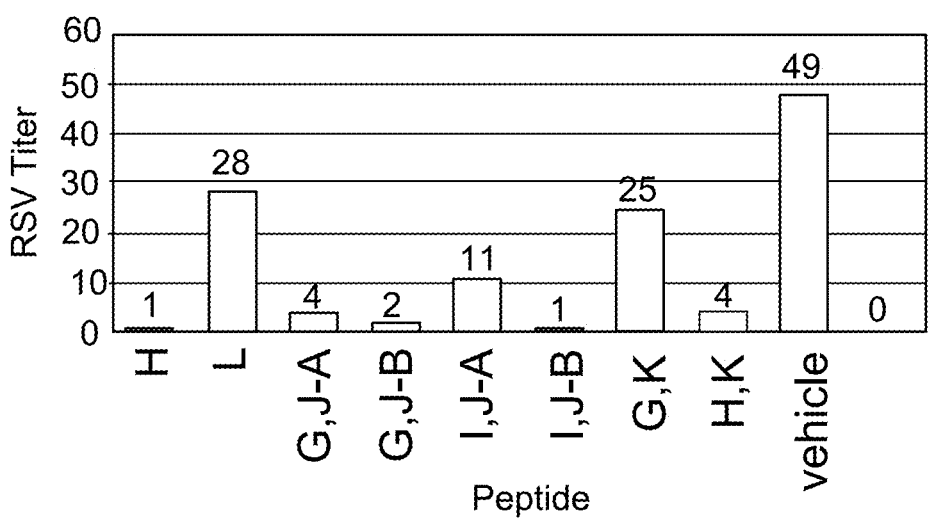
Figure 13:
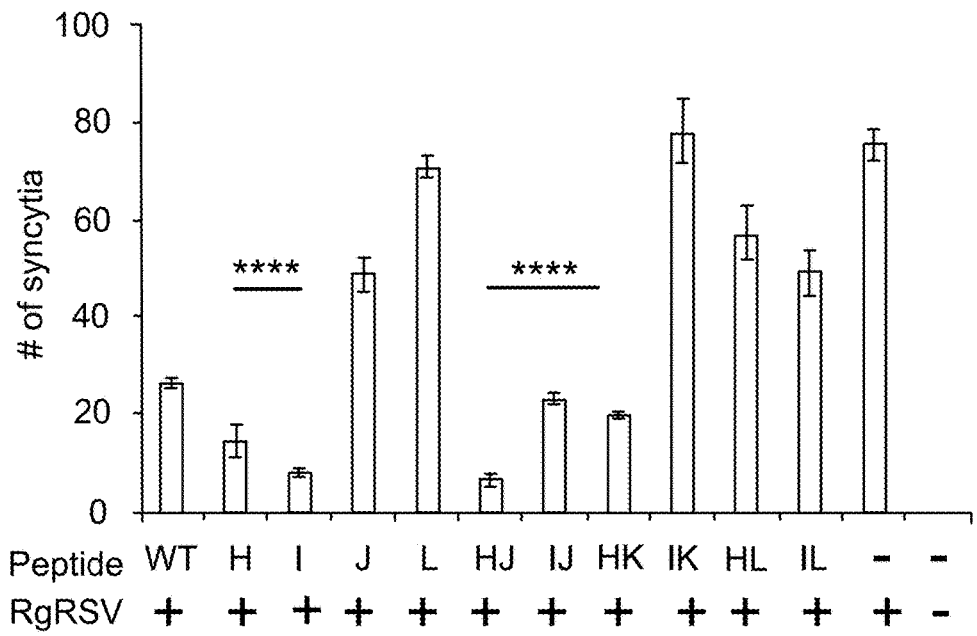
FIG. 13|Bar graph showing that stapled SAHF peptides inhibit RgRSV syncytia formation in A549 cells in a sequence-dependent manner.
Figure 14:
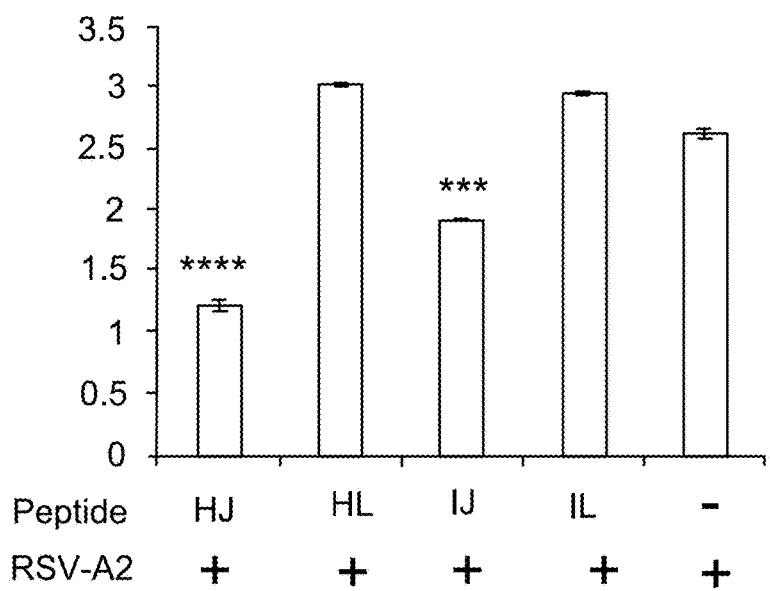
FIG. 14|Bar graph showing that stapled SAHF peptides H, J and I, J inhibit RSV-A2 infection of A549 cells.

In additional RSV infectivity assays, a series of doubly stapled SAHF peptides effectively suppressed RSV infectivity as demonstrated by a decrease in percent RSVF-positive Hep-2 cells, as detected by immunofluorescence analysis of cells subjected to 0.1 MOI wild-type RSV exposure after 15 min preincubation with the stapled peptides (see FIG. 11A), and a decrease in wild-type RSV titers as measured by Hep-2 cell plaque count after exposure to serial dilutions of viral supernatants from Vero cells infected with 0.1 MOT RSV in the presence of 5 uM peptides (see FIG. 11B).

Example 5: SAHF Peptides Engage the Plasma Membrane and Colocalize with RSV During Infection FITC-labeled SAHF peptides engage the plasma membrane of cultured Vero cells and are taken up via the pinosomal pathway, as evidenced by the gradual accumulation of FITC-SAHF-C in intracellular vesicles labeled with cytotracker red. Colocalization of FITC SAHF-C peptide and Rhodamine (R18)-labelled RSV was also evident during cellular contact and uptake, highlighting the capacity of SAHF peptides to target RSV during the infection process.

Example 6: SAHF Inhibits RSV Infection In Vivo

To examine the capacity of SAH-RSV peptides to inhibit RSV infection in vivo, vehicle or SAH-RSV peptide (250 μM, 25 μL) was administered to anesthetized mice intranasally followed by transnasal infection with rgRSV (5×10$^5$ PFU, 36 μL) four hours later. Mice were sacrificed 20 hours post-infection, and the nasal epithelium cryosectioned, stained with DAPI, and imaged using a fluorescent microscope. As shown in FIG. 6, whereas the nasal mucosa of rgRSV-infected mice demonstrated striking fluorescence of the nasal mucoas, SAHF-C, which bound the 5-helix bundle and suppressed RSV infection in vitro, markedly suppressed RSV infection, as reflected by a significant decrease in GFP-positive cells (FIG. 6D). In contrast, SAHF-L, which exhibited no binding activity nor suppressed RSV infection in vitro, had no in vivo activity, highlighting the specificity of action of SAHF-C (FIG. 6D). These studies demonstrate the utility of SAHF peptides in directly and specifically engaging RSV to block RSV infection, and highlight that SAHF may be applied topically by nose drop to prevent, suppress, and/or treat RSV infection in vivo.

Example 7: SAHF Peptides Both Prevent and Treat RSV Infection

Vero cells plated in 48-well format (60,000 cells/well) were exposed to (a) rgRSV only (0.1 MOI); (b) rgRSV for 1 hour followed by treatment with SAHF; and (c) SAHF for 1 hour followed by rgRSV infection, and then imaged 24 hour post-infection to quantitate infectivity by confocal microscopy and FACS analysis.

Figure 8A:
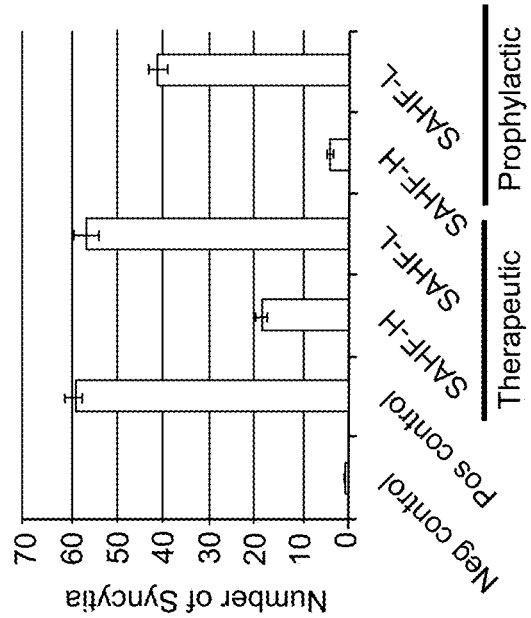
FIGS. 8A-B|Bar graphs showing that an exemplary SAHF peptide (SAHF-H), but not a negative control SAHF construct (SAHF-L), blocks RSV infection of Vero cells whether administered before or after viral exposure.
Figure 8B:
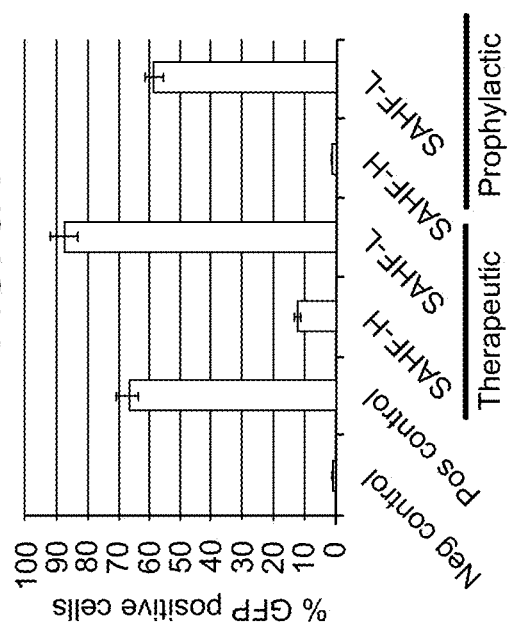
Figure 8C:
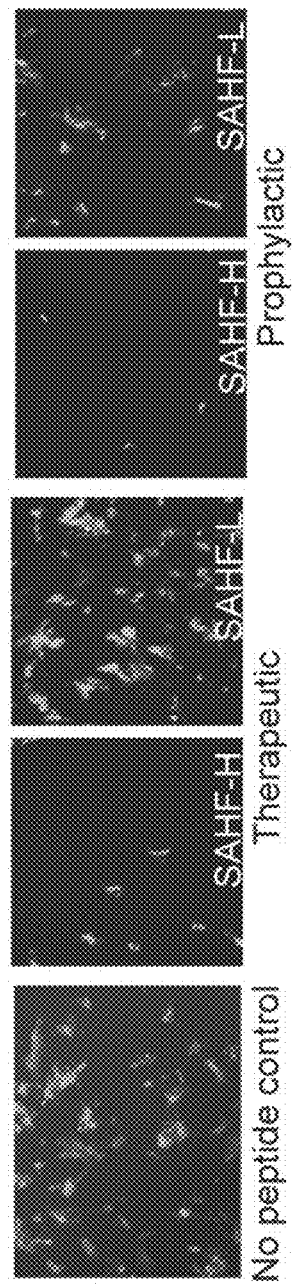
FIG. 8C|Image showing that SAHF-H, but not SAHF-L, inhibits virus-induced syncytia formation, whether administered before or after viral exposure.

As shown in FIGS. 8A and 8B, SAHF-H treatment inhibited RSV infection when administered prophylactically and even when administered after infection. SAHF-H (Fig. also blocked syncytial formation (FIG. 8C). As a measure of specificity, SAHF-L, which did not bind to the RSV 5-helix bundle (FIG. 4C), had little to no effect in these assays.

Example 8: Photoreactive SAHF Peptides for Protein Capture and Binding Site Analysis To identify and confirm SAHF targets in the context of cellular infection by RSV, stapled peptides derivatized for proteomic analyses are employed. First, photoreactive SAHF constructs are synthesized in which (1) a non-natural amino acid containing the photoreactive benzophenone functionality (Fmoc-Bpa) is substituted at discrete sites along the hydrophobic interaction surface of the HR domain and (2) the N-terminus of the peptide is capped with biotin for robust streptavidin-based target retrieval. Then, the photoreactive SAHF (pSAHF) is added to cultured cells exposed to RSV virus, and upon UV irradiation, the pSAHF intercalates into target protein(s). Infected cells are lysed, pelleted, and the isolated supernatant subjected to SA pulldown to retrieve pSAH-crosslinked proteins. The complexes are eluted by heating in load buffer and then trypsinized and subjected to MS-based identification using a reverse-phase nanoflow LC/MS/MS with an online LTQ-Orbitrap mass spectrometer (Thermo Scientific). MS data are processed using SEQUEST and Mascot software to catalogue protein targets.

Specific hits are defined as those proteins uniquely found in pSAHF-treated and irradiated samples, but not in the unirradiated controls or in pSAHF mutant-treated samples. This methodology allows identification of those amino acid residues in the target protein specifically modified by the pSAHF, thus revealing the explicit site(s) of SAHF peptide interaction.

Example 9: Structured Antigens for RSV Vaccination

Structurally constrained-RSV HR peptides are conjugated to protein carrier (e.g. KLH), followed by rabbit immunization, antisera collection, and ELISA-based immunogenicity testing. For a given structurally constrained RSVF construct, the unmodified template peptide and three alternatively conjugated stapled analogs are compared in a neutralizing immunogenicity study. Once prebled (~5 mL serum), two NZW female rabbits (6-8 weeks old) per immunogen receive a primary intramuscular (IM) injection (250 μg with Freund's complete, CpG-ODN, or Ribi adjuvant) on day 1, followed by IM boosts (100 μg with corresponding adjuvant) on days 21, 42, 63, 84, and 105, and production bleeds on days 52, 73, 94, and 112. Direct ELISA assays is performed for each production bleed to monitor and compare specific antibody production titers. Briefly, 96-well microtiter plates are coated with individual RSV HR immunogens (5 μg/mL) overnight at 4° C. The wells are washed twice with PBS containing 0.05% Tween 20 and blocked with 3% BSA for 45 min at 37° C. Serial dilutions of rabbit antisera are then added to the plate in triplicate and incubated at 37° C. for 2 hours. After washing three times, a 1:500 dilution of alkaline phosphatase-labeled goat anti-rabbit IgG in PBS/1% BSA is added, and the plate incubated for 40 min at room temperature. The wells are washed, exposed to alkaline phosphatase substrate for 30 minutes, and analyzed by microplate reader at 405 nm.

In addition to direct N-terminal conjugation of structured RSV HR peptides (e.g. via thiol of installed cysteine) or installation of a lysine for conjugation on the non-interacting face of SAHF peptides, olefin derivatization of hydrocarbon staples can also be performed so the proposed "neutralizing face" of the constructs can be directed outward, maintaining the non-neutralizing face buried against the protein or lipid conjugate (e.g. KLH14, bovine serum albumin, cholera toxin, micelle). Catalytic osmium tetroxide is used to first dihydroxylate the olefin, followed by cyclization with thionyl chloride or carbonyl diimidazole. The electrophilic cyclic sulfite or carbonate is then reacted with sodium azide, which is reduced to an amine using phosphines. Reaction with the bifunctional reagent 3-thiopropionic acid installs a thiol, which is then used to attach the carrier (e.g. maleimide-KLH). As an alternative approach, the peptides can be presented in the context of a lipid membrane, which may facilitate neutralizing antibody recognition. For example, the peptides can be differentially conjugated to 1,3-dipalmitoyl-glycero-2-phosphoethanolamine, which is then combined with dodecylphosphocholine (DPC) to generate immunogen-tethered micelles.

A DNA prime-protein boost immunization strategy has been shown to be more effective than protein-alone or DNA-alone vaccination to yield HIV-1 neutralization antibodies. An analogous approach for RSV can be tested with lead structured RSV HR conjugates replacing the timed protein boosts with structured peptide boosts according to the published immunization protocols.

Example 10: Stapled SAHF Peptides Inhibit RgRSV Infection

In this study A549 cells were plated in a 24 well plate at 30,000 cells/well. The following day, the cells were treated with 5 μM of the indicated stapled SAHF peptide or volume-equivalent DMSO vehicle, followed by RgRSV infection within 1 h at 0.1 MOI. The infection medium was removed at 1 h post-infection and the medium was replaced with 400 μl of DMEM containing 5% FBS with 5 μM of the indicated SAHF peptide. Cells were then incubated at 37° C. and 24 hours later harvested for determination of percent GFP-positive cells by flow cytometry. The results of this analysis are shown in FIGS. 12A and 12B. In the graph of FIG. 12B bars represent mean+/−SEM for experiments performed in triplicate and $p<0.0001$ for conditions with overlying horizontal bar.

Example 11: Stapled SAHF Peptides Inhibit RgRSV Syncytia Formation

In this study A549 cells were plated and treated as described in Example 10, except that the number of viral syncytia were counted at 48 hours post-infection. Syncytia were counted in three different wells at four discrete locations per well. The results of this analysis are shown in FIG. 13 in which error bars represent mean+/−SEM and $p<0.0001$ for conditions with overlying horizontal bar and asterisks.

Example 12: SAHF Peptides Inhibit RSV-A2 Infection

In this study A549 cells were plated in a 24 well plate at 30,000 cells/well. The following day, the cells were treated with 5 μM of the indicated stapled SAHF peptide or volume-equivalent DMSO vehicle, followed by RSV-A2 infection at 1 MOI. The cells were infected for 2 h, and the infection medium replaced with 400 μl of DMEM containing 5% FBS and 5 μM of the indicated stapled SAHF peptide. Cells were harvested along with the supernatant 24 h post infection, vortexed for 10 sec, and the supernatant collected, leaving the cell pellet behind. Hep-2 cells were plated on a 24 well plate at 60,000 cells/well the day before use. Plaque assay was performed on Hep-2 cells using the collected supernatant and titers determined at 5 days post infection of Hep-2 cells. The results of this analysis are shown in FIG. 14 in which titers are shown as log 10 pfu/ml and the values represent the mean+/−SEM for two independent experiments (*p<0.001; **p<0.0001).

Figure 15A:
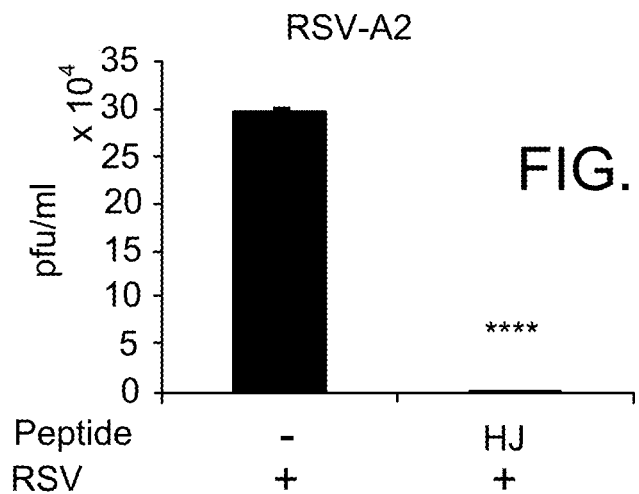
FIGS. 15A-15C|Bar graphs showing that stapled SAHF-H, J peptide prevents viral infection by RSV-A2 (A), RSV-2-20 (B) and RSV-rA2 Line 19F (C).
Figure 15B:
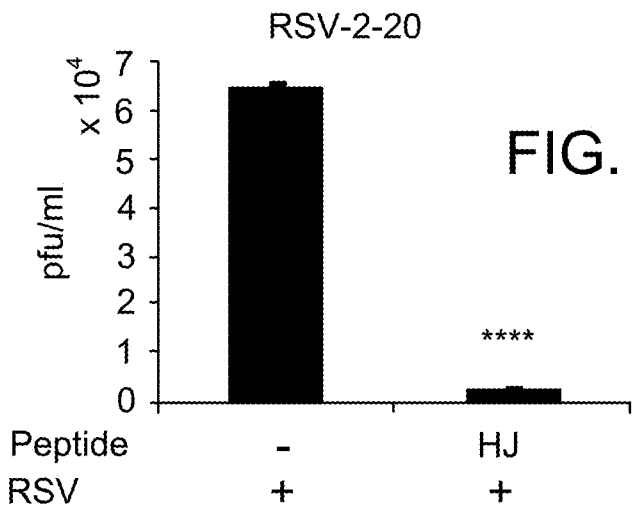
Figure 15C:
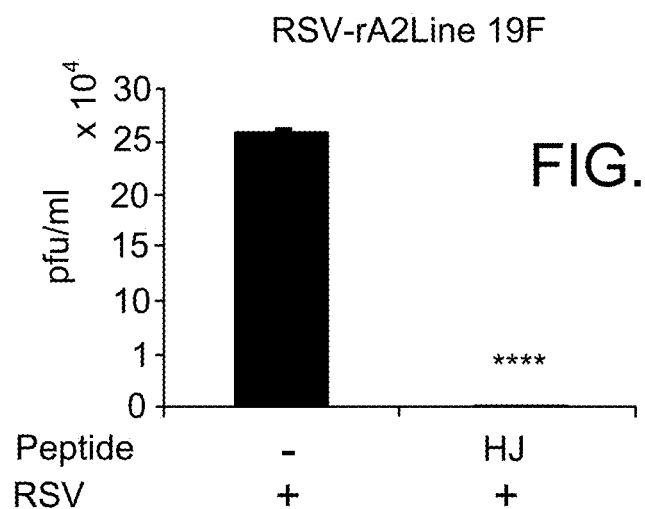

Example 13: Stapled SAHF-H, J Peptide Prevents Viral Infection by Three Different RSV Strains In this study A549 cells were plated in a 24 well plate at 30,000 cells/well. The following day, the cells were treated with 5 μM of the indicated stapled SAHF peptide or volume-equivalent DMSO vehicle, followed by infection with RSV-A2, RSV 2-20, or RSV-rA2Line19F within 30 minutes at 0.1 MOI. The supernatant was collected 24 h post infection, and applied to Hep-2 cells that were plated the day prior on a 24 well plate at 60,000 cells/well. Plaque assays were performed on Hep-2 cells using the collected supernatant and titers determined at 5 days post infection of Hep-2 cells. The results of this analysis are shown in FIGS. 15A, 15B and 15C in which titers are shown as pfu/ml and the values represent the mean+/−SEM for two independent experiments (*p<0.001; **p<0.0001).

Figure 16B:
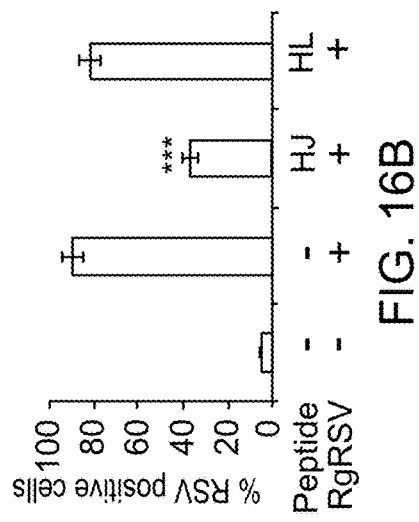
FIGS. 16A-16C|Photographs (A, C) and bar graph (B) showing that stapled SAHF-H, J peptide blocks intranasal RgRSV infection in a sequence-specific manner in mice.
Figure 16A:
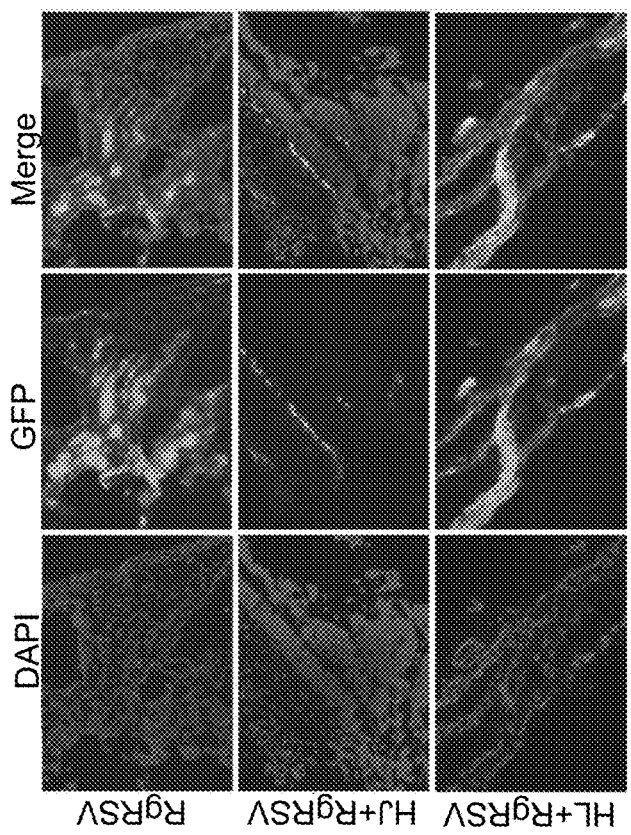
Figure 16C:
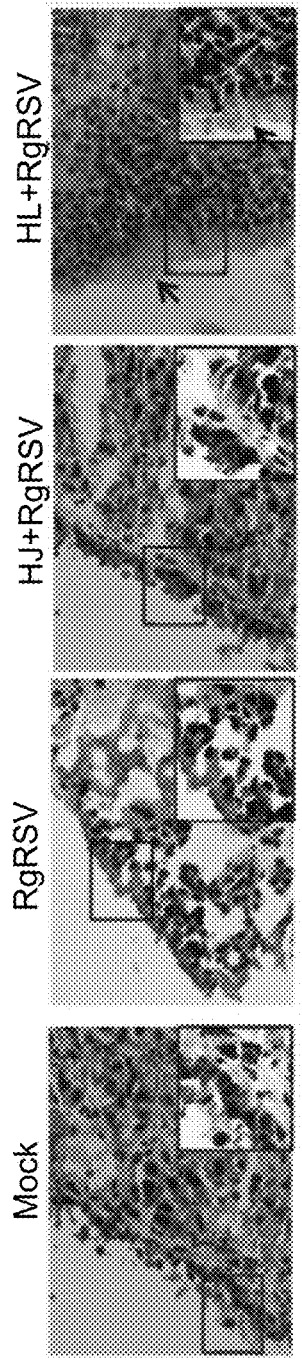

Example 14: Stapled SAHF-H, J Peptide Blocks Intranasal RgRSV Infection in a Sequence-Specific Manner In this study four groups (n=2 per group) of ten week old BALB/c mice were anesthetized and treated intransally with stapled SAHF-H, J or stapled SAHF H, L peptide (125 μM in 1.2% DMSO) or volume-equivalent vehicle. One hour post treatment, three groups of mice were inoculated with a single dose of RgRSV at $1\times10^6$ pfu/mouse, with the fourth group receiving a mock inoculation. Mice were sacrificed at 24 hours post infection and the noses harvested, sectioned, stained with DAPI and imaged with an Olympus fluorescent microscope (FIG. 16A; original magnification 20×). Image J analysis was performed on the acquired images (FIG. 16B) and average GFP positive (green) and DAPI positive (blue) cells were calculated from eight images (4 sections) per mouse (bars represent percent GFP positive of total DAPI-positive cells present in the images and error bars represent mean+/−SEM. *, p<0.001). FIG. 16C depicts the results of hematoxylin and eosin staining of the nose sections (original magnification 20×, insets 100×) In FIG. 16C black arrows highlight thickened mucosa. Inflammation is noted in RgRSV-infected sections treated with vehicle or HL peptide, whereas sections from mock infected and Rg-RSV-infected mice treated with HJ peptide demonstrate comparatively decreased inflammatory cells.

Example 15: Prophylactic Intranasal Treatment with Stapled SAHF-H, J Peptide Inhibits RSV-A2 Lung Infection In this study four groups (n=3 per group) of ten week old BALB/c mice were anesthetized and treated intranasally with stapled SAHF-H, J or stapled SAHF-H, L peptides (125 μM in 1.2% DMSO) or volume-equivalent vehicle. One hour post treatment, three groups of mice were inoculated with a single dose of RSV-A2 at $1\times10^6$ pfu/mouse. Peptide dosing and viral inoculation was repeated 16 hours post-infection. The fourth group was treated with volume-equivalent vehicle and mock-infected. Two mice from each group were sacrificed 4 days after the second infection and left lung lobes harvested after 1% paraformaldehyde perfusion, followed by cryopreservation in OCT. Sections (5 μm) were treated with 1:1000 dilution of rabbit anti-RSV polyclonal antibody (Millipore) overnight followed by anti-rabbit antibody conjugated to Alexa Fluor 555 (1:400) (red) (Molecular Probes) for 1 h. Sections were washed and mounted with medium containing DAPI (blue) and viewed with an Olympus fluorescent microscope (FIG. 17A; original magnification 20×). Image J analysis was performed on the acquired images and the percentage RSV-positive cells (red) of total DAPI-positive cells (blue) determined from 8 images (4 sections) per mice (FIG. 17B; .error bars represent mean+/−SEM; *, p<0.0001). Four days after the second infection, bronchoalveolar lavage (BAL) was performed on one mouse from each group and BAL supernatant used to determine the viral titers by plaque assay on Hep-2 cells (FIG. 17C; error bars represent mean+/−SEM of plaques counted per in vivo specimen; *, p<0.05). Also at four days after the second infection, cranial and caudal lobes of the right lung from two mice per group were snap frozen on dry ice. A lung homogenate was generated from the cranial lobe and supernatant subjected to viral titer determination (log 10 pfu/ml) (FIG. 17D; error bars represent mean+/−SEM; *, p<0.05). Total RNA was isolated from the caudal lobe of the right lung and quatitative RT-PCR was performed for the RSV-N gene. The results of this analysis are presented in FIG. 17E in which the bar graphs represent the RSV-N gene expression normalized to the mock-infected tissue. For this experiment, an additional treatment group received unmodified RSV-F peptide with no observed effect. By each measure, prophylactic intranasal treatment with stapled SAHF-H, J inhibited RSV infection, whereas the control stapled SAHF-H, L peptide had no effect.

Figure 18A:
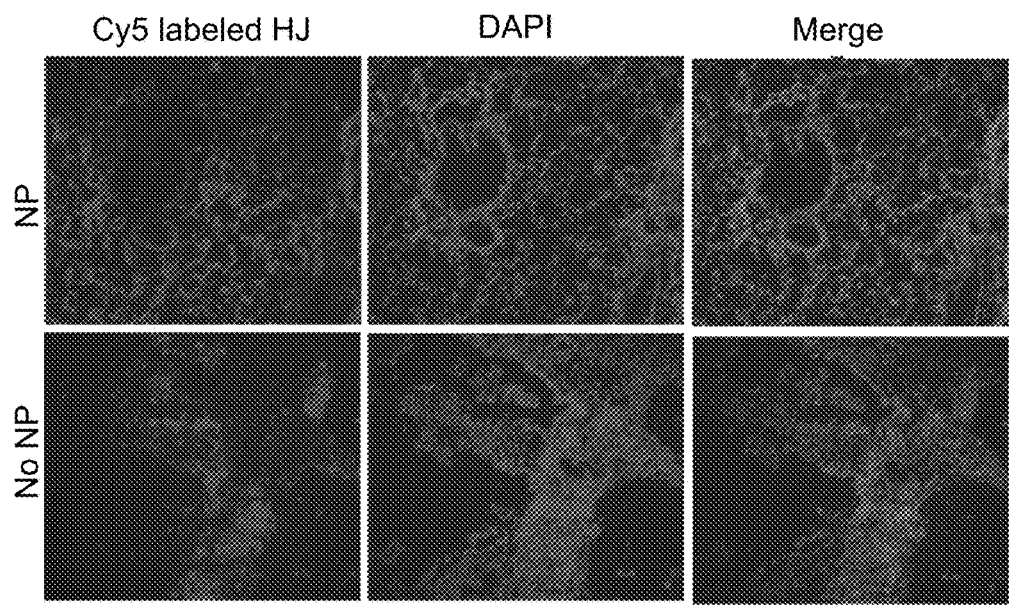
FIGS. 18A-18B|Photograph (A) and bar graph (B) showing that administration of stapled SAHF-H, J peptide as a nanoparticle preparation increases lung delivery in mice.
Figure 18B:
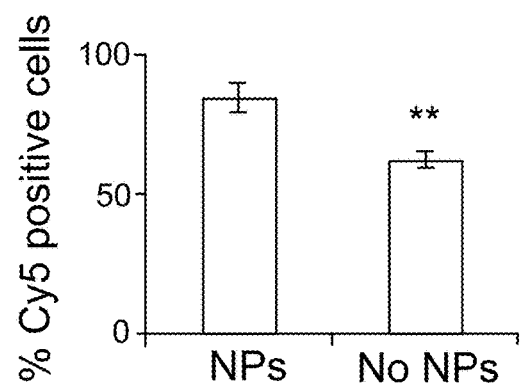

Example 16: Administration of Stapled SAHF-H, J Peptide as a Nanoparticle Preparation Increases Lung Delivery In this study three groups (n=2) of 10 week old mice were treated intratracheally with Cy5-labeled stapled SAHF-H, J administered alone (100 μM) or in combination with nanoparticles (NP) formed of nanochitosan polymer (Zhang et al. 2005 *Nature Medicine* 11:56) (1:2.5, peptide:NP) in a 50 μl volume. The control group received volume-equivalent vehicle. Mice were sacrificed at 24 hours post-treatment and lungs were harvested after 1% paraformaldehyde perfusion, followed by cryopreservation in OCT. Section (5 μm) were mounted in DAPI-containing medium and imaged with an Olympus fluorescent microscope (FIG. 18A; original magnification 20×). Image J analysis of the acquired images determined the percentage Cy5-positive cells of total DAPI-positive cells (FIG. 18B; error bars represent mean+/−SEM; *, p<0.01). A statistically significant increase in peptide delivery was observed for the stapled SAHF-H, J peptide delivered as an nanoparticle preparation.

Figure 19:
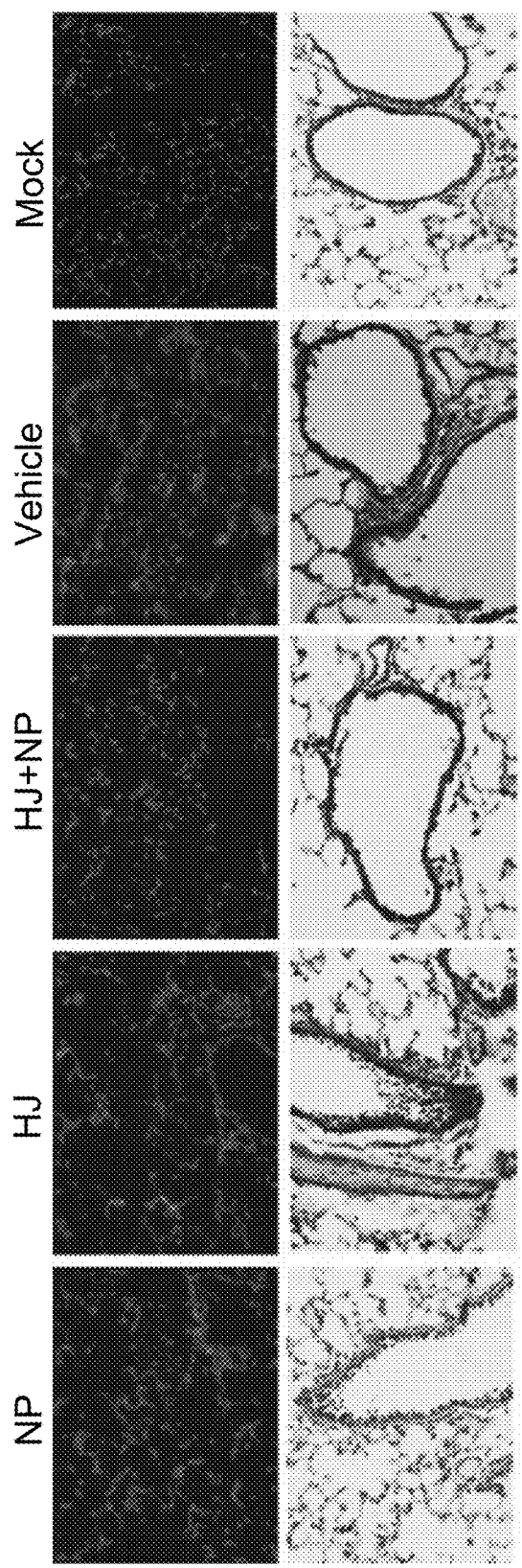
FIG. 19|Photographs showing that intratracheal administration of stapled SAHF-H, J peptide as a nanoparticle preparation at 48 hours pre-RSV inoculation markedly suppresses viral infection of the lung in mice.
Figure 20:
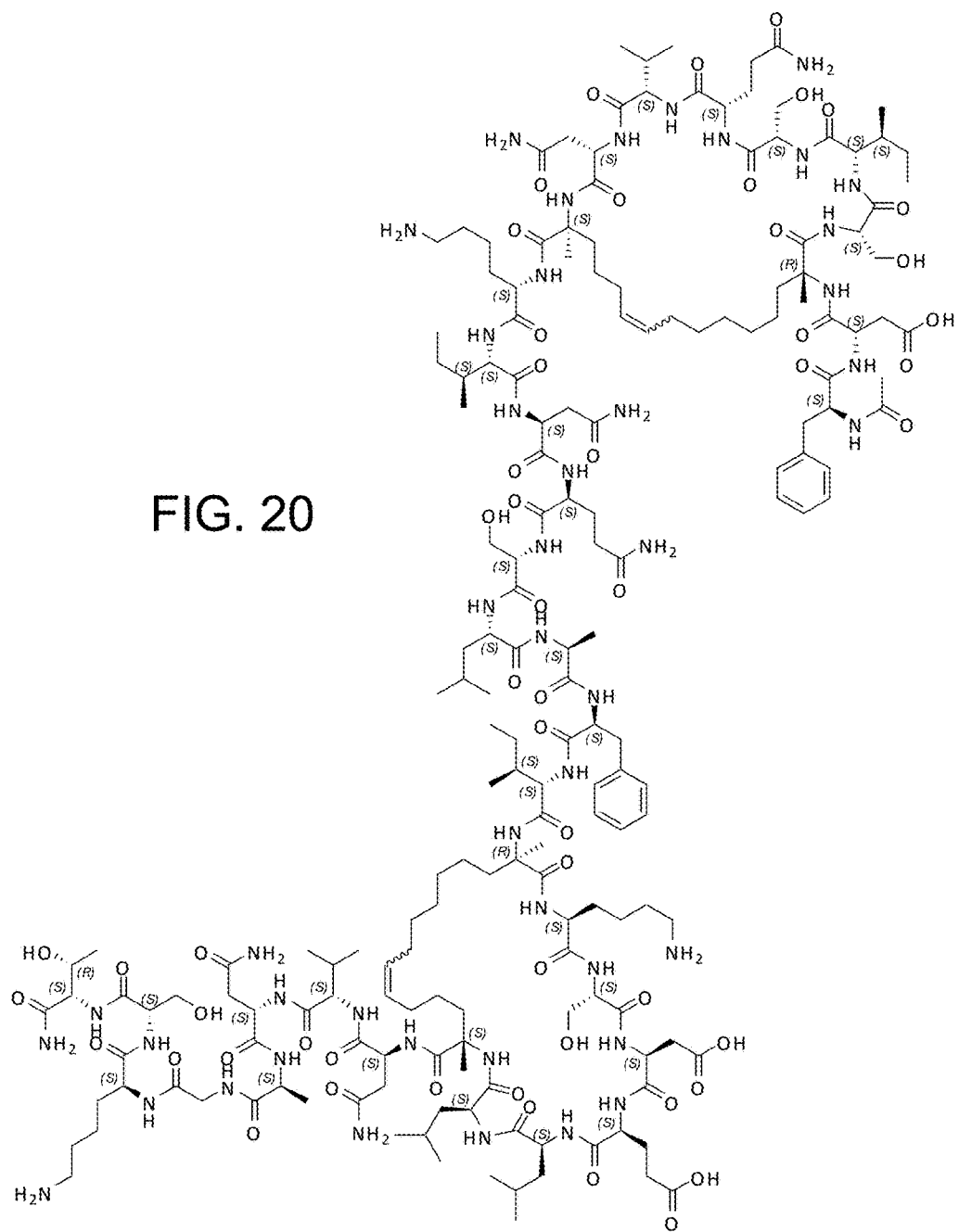
FIG. 20|A depiction of the structure of stapled SAHF-H, J peptide.

Example 17: Intratracheal Administration of Stapled SAHF-H, J Peptide as a Nanoparticle Preparation at 48 Hours Pre-RSV Inoculation Markedly Suppresses Viral Infection of the Lung In this study four groups (n=3 per group) of ten week old BALB/c mice were anesthetized and treated intratracheally with volume-equivalent vehicle with stapled nanoparticles (NP); stapled SAHF-H, J peptide alone (250 μM peptide in 1.2% DMSO), stapled SAHF-H, J peptide in combination with NP (1:2.5, peptide:NP), or volume-equivalent vehicle alone. Forty-eight hours after treatment, the four groups of mice were inoculated intranasally with a single dose of clinical isolate RSV-rA2Line19F at $1\times10^6$ pfu/mouse. A fifth treatment group (n=3) received volume-equivalent vehicle intratracheally followed by mock inoculation 48 hours later. Mice were sacrificed four days post-infection and left lung lobes were harvested after 1% paraformaldehyde perfusion, followed by cryopreservation with OCT. Sections (5 µm) were treated with 1:1000 dilution of rabbit anti-RSV polyclonal antibody (Millipore) overnight, followed by anti-rabbit antibody conjugated with Alexa Fluor 555 (1:400) (red) (Molecular Probes) for 1 h. Sections were washed and mounted in medium containing DAPI (blue) and images acquired using an Olympus fluorescent microscope (FIG. 19, top panel; original magnification 20×). Lung sections were also subjected to H&E staining (FIG. 19; bottom panel; original magnification 20×). Tissue specimens from stapled SAHF-H, J peptide/NP treated mice demonstrated a striking near-absence of RSV immunostaining, with H&E stained lung images mirroring those of mock-infected mice. Image J analysis, RSV-N expression, and viral titers from lung homogenates all corroborated the marked inhibition of viral lung infection by the stapled SAHF-H,J peptide/NP preparation, administered intratracheally 48 hours prior to infection with the clinical isolate RSV-rA2Line19F.

Example 18: CD Spectra of Stapled SAHF Peptides

Figure 21A:
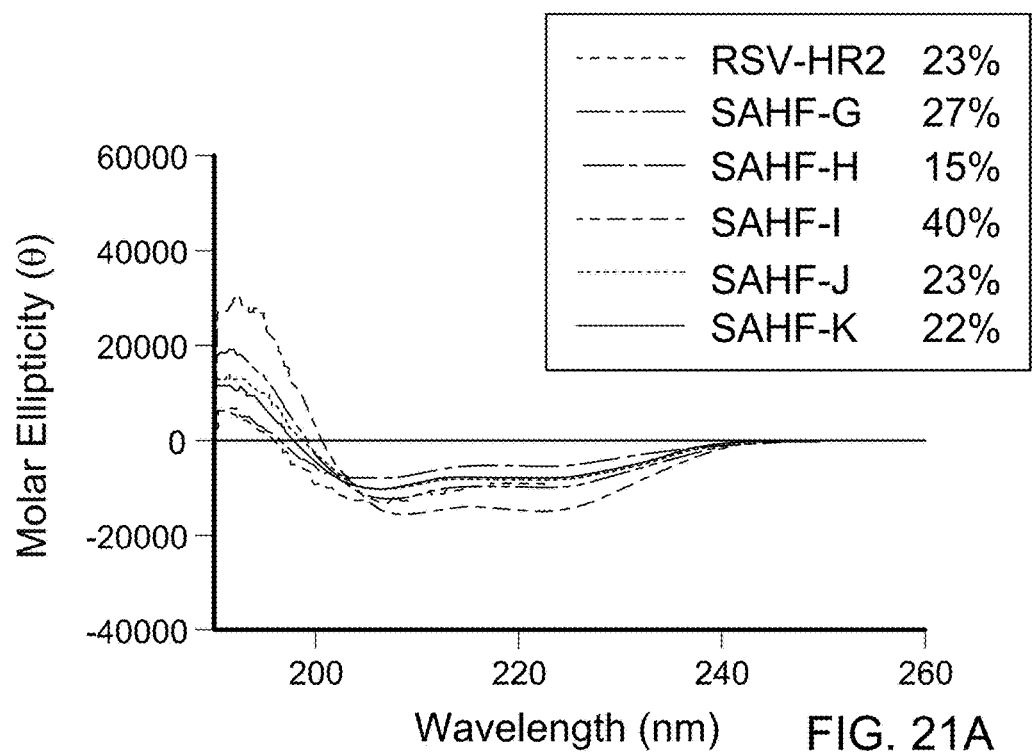
FIGS. 21A-21B|Graphs of the CD spectra of certain stapled SAHF peptides.
Figure 21B:
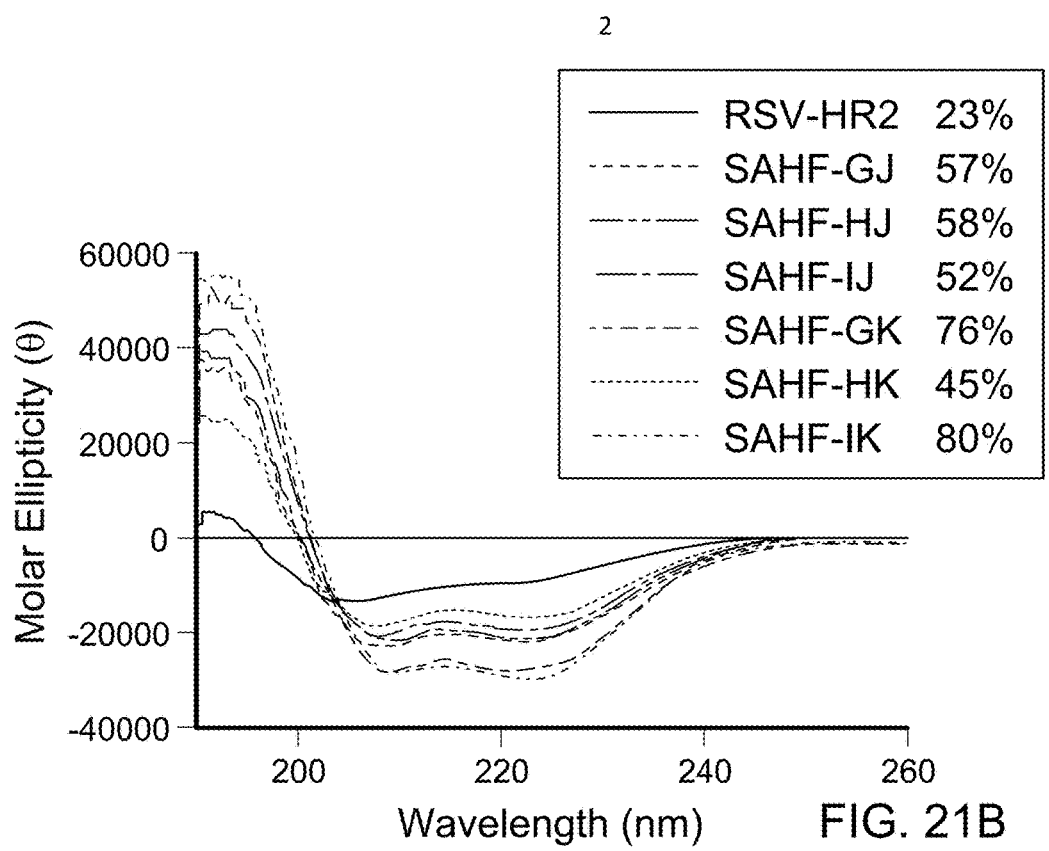

In this study the Circular dichroism spectra of single and double stapled SAHF peptides were examined. Certain single i, i+7 stapled peptides demonstrate enhanced alpha-helical content compared to the unmodified RSV-F template peptide (FIG. 21A).

Combinations of the single N-terminal (G, H, I) and C-terminal (J, K) i, i+7 stapled peptides consistently demonstrate marked enhancement in alpha-helicity compared to their single stapled counterparts (FIG. 21B).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An internally cross-linked polypeptide comprising the amino acid sequence $A_0B_0C_0D_0E_0F_0G_0A_1B_1C_1D_1E_1F_1G_1A_2B_2C_2D_2E_2F_2G_2A_3B_3C_3D_3E_3F_3G_3A_4B_4C_4D_4E_4F_4G_4$ (SEQ ID NO:1) wherein:

$A_0$ is Phe;
$B_0$ is Asp or Glu;
$C_0$ is Ala, Val, Ile, Leu, or Ser;
$D_0$ is Ser;
$E_0$ is Ile;
$F_0$ is Ser or Thr;
$G_0$ is Gln or Asn;
$A_1$ is Val;
$B_1$ is Asn or Gln;
$C_1$ is Glu or Asp;
$D_1$ is Lys;
$E_1$ is Ile;
$F_1$ is Asn or Gln;
$G_1$ is Gln or Asn;
$A_2$ is Ser;
$B_2$ is Leu;
$C_2$ is Ala, Val, Leu, Ser, or Ile;
$D_2$ is Phe;
$E_2$ is Ile;
$F_2$ is Arg or Lys;
$G_2$ is Lys;
$A_3$ is Ser;
$B_3$ is Asp;
$C_3$ is Glu or Asp;
$D_3$ is Leu;
$E_3$ is Leu;
$F_3$ is His, Arg, or Lys;
$G_3$ is Asn or Gln;
$A_4$ is Val;
$B_4$ is Asn;
$C_4$ is Ala, Leu, Ile, Ser, or Val;
$D_4$ is Gly;
$E_4$ is Lys;
$F_4$ is Ser or Thr; and
$G_4$ is Thr or Ser; wherein
zero to five amino acids at positions corresponding to $A_0$, $D_0$, $E_0$, $A_1$, $D_1$, $E_1$, $A_2$, $B_2$, $D_2$, $E_2$, $A_3$, $B_3$, $D_3$, $E_3$, $A_4$, $B_4$, $D_4$, and $E_4$ are substituted by a conservative amino acid;
two to four amino acids of SEQ ID NO:1 separated by two, three, or six amino acids are replaced with non-natural amino acids with olefinic side chains, and:
if two amino acids of SEQ ID NO:1 are replaced with non-natural amino acids, then the side chains of the two amino acids are joined by an internal staple;
if three amino acids of SEQ ID NO:1 are replaced with non-natural amino acids, then the side chains of the three amino acids are joined by internal staples and/or an internal stitch; or
if four amino acids of SEQ ID NO:1 are replaced with non-natural amino acids, then the side chains of the four amino acids are joined by internal staples, internal stiches, or a combination of internal staples and stiches.

2. The internally cross-linked peptide of claim 1, wherein:

$A_0$ is Phe,
$B_0$ is Asp,
$C_0$ is Ala or Ser,
$D_0$ is Ser,
$E_0$ is Ile,
$F_0$ is Ser,
$G_0$ is Gln,
$A_1$ is Val,
$B_1$ is Asn,
$C_1$ is Glu,
$D_1$ is Lys,
$E_1$ is Ile,
$F_1$ is Asn,
$G_1$ is Gln,
$A_2$ is Ser,
$B_2$ is Leu,
$C_2$ is Ala,
$D_2$ is Phe,
$E_2$ is Ile,
$F_2$ is Arg,
$G_2$ is Lys,
$A_3$ is Ser,
$B_3$ is Asp,
$C_3$ is Glu,
$D_3$ is Leu,
$E_3$ is Leu,
$F_3$ is His,
$G_3$ is Asn,
$A_4$ is Val,
$B_4$ is Asn,
$C_4$ is Ala or Val,
$D_4$ is Gly,
$E_4$ is Lys,
$F_4$ is Ser, and
$G_4$ is Thr,
wherein two to four amino acids of SEQ ID NO:1 separated by three or six amino acids are replaced with non-natural amino acids with olefinic side chains.

3. The cross-linked peptide of claim 1, wherein the amino acid sequence is FDASISQVNEKINQSLAFIRKSDELLH-NVNAGKST (SEQ ID NO:2), wherein two to four amino acids of SEQ ID NO:2 separated by three or six amino acids are replaced with non-natural amino acids with olefinic side chains.

4. The cross-linked peptide of claim 1, wherein the internal staple replacing the side chains of the two amino acids separated by two or six amino acids comprises an internal staple selected from Table 1.

5. The cross-linked peptide of claim 4, wherein the internally cross-linked peptide is selected from the group consisting of SEQ ID NOs: 10, 11, 12, 13, 14, 15, 16, 17, and 18.

6. The cross-linked peptide of claim 1, wherein the internal staples and/or the internal stitch replacing the side chains of the three amino acids comprise an internal stitch selected from Table 1.

7. The cross-linked peptide of claim 1, wherein the internal staples and/or the internal stitch replacing the side chains of the three amino acids comprises at least two internal staples.

8. The cross-linked peptide of claim 1, wherein the internal staples and/or the internal stitch replacing the side chains of the three amino acids comprises a combination of at least one internal staple and an internal stitch.

9. The cross-linked peptide of claim 6, wherein the internal stitch replaces the side chain of a first amino acid and a second and a third amino acid thereby cross-linking the first amino acid to the second and third amino acid via an internal cross-link, wherein the first and second amino acid are separated by two, three, or six amino acids, the first and the third amino acids are separated by two, three, or six amino acids, and the second and third amino acids are distinct amino acids.

10. The cross-linked peptide of claim 6, wherein the internal stitch replacing the side chains of the three amino acids cross-links a pair of amino acids separated by two, three, or six amino acids.

11. The cross-linked peptide of claim 1, wherein four amino acids of SEQ ID NO:1 are replaced with non-natural amino acids with olefinic side chains, each pair of the four amino acids are separated by three or six amino acids, and wherein the side chains of the four amino acids are joined by two distinct internal staples.

12. The cross-linked peptide of claim 11, wherein a first of the two distinct internal staples cross-links a first pair of amino acids separated by three or six amino acids, and a second of the at least two distinct internal staples cross-links a second pair of amino acids separated by three or six amino acids.

13. The cross-linked peptide of claim 1, wherein the internally cross-linked peptide is selected from the group consisting of SEQ ID NOs: 6, 19, 20, 21, 22, 23, 24, 25, and 26.

14. The cross-linked peptide of claim 13, wherein the peptide comprises FD8'SISQVNX'KINQSLAFI8"KSDELLX"NVNAGKST (SEQ ID NO:20), wherein there is a first internal crosslink between 8' and X' and a second internal crosslink between 8" and X".

15. The cross-linked peptide of claim 14, wherein the first cross-link is a C11 alkylene between the alpha carbons of 8' and X' and the second cross-link is a C11 alkylene between the alpha carbons of 8" and X".

16. The cross-linked peptide of claim 14, wherein the alpha carbons of 8', X', 8" and X" are substituted with a methyl group.

17. The cross-linked peptide of claim 1, wherein the internal staples, internal stiches, or the combination of internal staples and internal stitches replacing the side chains of the at least four amino acids comprises at least one staple and at least one stitch.

18. The cross-linked peptide of claim 17, wherein the at least one staple cross-links a pair of amino acids separated by two, three, or six amino acids and the at least one stitch cross-links a first amino acid to a second amino acid and a third amino acid, wherein the first and second amino acid are separated by two, three, or six amino acids, the first and the third amino acids are separated by two, three, or six amino acids, and the second and third amino acids are distinct amino acids.

19. The cross-linked peptide of claim 17, wherein the at least one staple is selected from Table 1.

20. A method of treating Respiratory Syncytial Virus (RSV) in a human subject, the method comprising:
selecting a human subject at risk of or with RSV infection; and
administering to the human subject an effective amount of the peptide of claim 1.

21. The method of claim 20, comprising:
assessing a level of RSV or a symptom associated with RSV in the human subject before and after treatment; and
continuing treatment until a decrease in the level of RSV or the symptom associated with RSV in the human subject.

22. A compound comprising the internally cross-linked polypeptide of claim 1.

23. The compound of claim 22, wherein the compound comprises polyethylene glycol or spermine.

24. The compound of claim 22, wherein the polyethylene glycol is linked to the cross-linked polypeptide through a biodegradable linker.

25. A peptide of 35 amino acids in length that is at least 80% identical to FDASISQVNEKINQSLAFIRKSDELLH-NVNAGKST (SEQ ID NO:2), wherein the peptide comprises a stabilized alpha-helix with non-natural amino acids comprising a hydrocarbon staple between relative positions: (1) i and i+3, (2) i' and i'+4, (3) i" and i"+7, or (4) i' and i'+4 and i" and i"+7 of SEQ ID NO:2, and wherein the peptide binds recombinant RSV 5-helix bundle protein.

26. The peptide of claim 25, wherein the amino acids at positions 1, 4, 5, 8, 11, 12, 15, 16, 18, 19, 21, 22, 23, 25, 26, and 29-33 of SEQ ID NO:2 are unaltered.

27. The peptide of claim 25, wherein the peptide comprises an amino acid sequence that is at least 90% identical to SEQ ID NO:2.

28. The peptide of claim 25, comprising the amino acid sequence set forth in any one of SEQ ID NOs.: 10-14, 17, or 19-24.

29. The peptide of claim 25, wherein the peptide binds recombinant RSV 5-helix bundle protein with greater affinity than a peptide of SEQ ID NO:2.

30. The peptide of claim 25, wherein the non-natural amino acid amino acids are: S5, R8, or S5 and R8.

31. A method of immunizing a human subject against RSV, the method comprising:
selecting a human subject at risk for RSV infection; and
administering to the human subject an effective amount of the peptide of claim 25.

32. A peptide comprising an amino acid sequence that is at least 80% identical to FDASISQVNEKINQSLAFIRKS-DELLHNVNAGKST (SEQ ID NO:2), wherein either one or both of the amino acids at positions 21 and 31 of SEQ ID NO: 2 is unaltered, the peptide comprises a stabilized alpha-helix with non-natural amino acids comprising a hydrocarbon staple between relative positions: (1) i and i+3, (2) i' and i'+4, (3) i" and i"+7, or (4) i' and i'+4 and i" and i"+7 of SEQ ID NO:2, and the peptide binds recombinant RSV 5-helix bundle protein.

33. The peptide of claim 32, wherein the amino acids at positions 1, 4, 5, 8, 11, 12, 15, 16, 18, 19, 21, 22, 23, 25, 26, and 29-33 of SEQ ID NO:2 are unaltered.

34. The peptide of claim 32, wherein the peptide comprises an amino acid sequence that is at least 90% identical to SEQ ID NO:2.

35. The peptide of claim 32, comprising the amino acid sequence set forth in any one of SEQ ID NOs.: 10-14, 17, or 19-24.

36. The peptide of claim 32, wherein the peptide binds recombinant RSV 5-helix bundle protein with greater affinity than a peptide of SEQ ID NO:2.

37. The peptide of claim 32, wherein the non-natural amino acid amino acids are: S5, R8, or S5 and R8.

* * * * *